United States Patent
Heath et al.

(10) Patent No.: US 12,201,679 B2
(45) Date of Patent: Jan. 21, 2025

(54) EPITOPE-TARGETED PEPTIDE IMMUNOSTIMULANTS

(71) Applicant: Institute for Systems Biology, Seattle, WA (US)

(72) Inventors: James R. Heath, Seattle, WA (US); Matthew N. Idso, Seattle, WA (US); Mario Arrieta-Ortiz, Seattle, WA (US); Ajay Akhade, Seattle, WA (US)

(73) Assignee: Institute for Systems Biology, Seattle, WA (US)

( * ) Notice: Subject to any disclaimer, the term of this patent is extended or adjusted under 35 U.S.C. 154(b) by 0 days.

(21) Appl. No.: 16/841,635

(22) Filed: Apr. 6, 2020

(65) Prior Publication Data

US 2020/0323973 A1 Oct. 15, 2020

Related U.S. Application Data

(60) Provisional application No. 62/830,193, filed on Apr. 5, 2019.

(51) Int. Cl.
| | | |
|---|---|---|
| *A61K 38/08* | (2019.01) | |
| *A61K 39/085* | (2006.01) | |
| *A61K 39/108* | (2006.01) | |
| *A61K 47/64* | (2017.01) | |
| *C07K 7/06* | (2006.01) | |
| *G01N 33/68* | (2006.01) | |

(52) U.S. Cl.
CPC ............ *A61K 39/085* (2013.01); *A61K 38/08* (2013.01); *A61K 39/0266* (2013.01); *A61K 47/64* (2017.08); *C07K 7/06* (2013.01); *G01N 33/68* (2013.01); *G01N 33/6878* (2013.01)

(58) Field of Classification Search
CPC ........ A61K 38/03; A61K 38/08; A61K 47/64; C07K 7/06; C07K 7/56
See application file for complete search history.

(56) References Cited

U.S. PATENT DOCUMENTS

| | | |
|---|---|---|
| 4,899,755 A | 2/1990 | Lauffer |
| 5,474,756 A | 12/1995 | Tweedle |
| 5,547,668 A | 8/1996 | Kranz |
| 5,846,519 A | 12/1998 | Tweedle |
| 6,143,274 A | 11/2000 | Tweedle |
| 6,566,088 B1 | 5/2003 | Mcknight |
| 8,710,180 B2 | 4/2014 | Pitram |
| 8,841,083 B2 | 9/2014 | Heath |
| 8,906,830 B2 | 12/2014 | Agnew |
| 9,188,584 B2 | 11/2015 | Agnew |
| 9,221,889 B2 | 12/2015 | Pitram |
| 9,239,332 B2 | 1/2016 | Heath |
| 9,913,875 B2 | 3/2018 | Farrow |
| 10,598,671 B2 | 3/2020 | Heath |
| 11,007,245 B2 | 5/2021 | Farrow |
| 2006/0153839 A1 | 7/2006 | Mohamed |
| 2010/0009896 A1 | 1/2010 | Agnew |
| 2011/0177109 A1 | 7/2011 | Smith, III |
| 2011/0263515 A1 | 10/2011 | Agnew |
| 2012/0202219 A1 | 8/2012 | Agnew |
| 2012/0252071 A1 | 10/2012 | Greif |
| 2014/0302998 A1 | 10/2014 | Heath |
| 2015/0099658 A1 | 4/2015 | Pfeilsticker |
| 2015/0132314 A1 | 5/2015 | Masternak |
| 2015/0344523 A1 | 12/2015 | Deyle |
| 2016/0331800 A1* | 11/2016 | Farrow .................. C07K 7/06 |
| 2018/0364253 A1 | 12/2018 | Agnew |
| 2020/0407712 A1 | 12/2020 | Boyd |
| 2022/0211648 A1 | 7/2022 | Agnew |

FOREIGN PATENT DOCUMENTS

| | | |
|---|---|---|
| EP | 2719706 | 4/2014 |
| WO | 1986006605 | 11/1986 |
| WO | 1991003200 | 3/1991 |
| WO | 1995028179 | 10/1995 |
| WO | 1995028967 | 11/1995 |
| WO | 1996023526 | 8/1996 |
| WO | 1997036619 | 10/1997 |
| WO | 1998018496 | 5/1998 |
| WO | 1998018497 | 5/1998 |

(Continued)

OTHER PUBLICATIONS

Lai et al. Epitope-Targeted Macrocyclic Peptide Ligand with Picomolar Cooperative Binding to Interleukin-17F. Chemistry—A European Journal. 2018, vol. 24, pp. 3760-3767. (Year: 2018).*

Agnew, et al., "Iterative In Situ Click Chemistry Creates Antibody-like Protein-Capture Agents", Angew. Chem. Int. Ed. Engl., 48:4944-4948 (2009).

Agnew, et al., "Protein-Catalyzed Capture Agents", Chem. Rev., 119:9950-70 (2019).

Alcántar-Curiel, et al., "Association of Antibiotic Resistance, Cell Adherence, and Biofilm Production with the Endemicity of Nosocomial Klebsiella pneumoniae", Biomed. Res. Int., 2018:7012958 (2018).

(Continued)

*Primary Examiner* — Jeffrey E. Russel
(74) *Attorney, Agent, or Firm* — Fenwick & West LLP; Carl A. Morales; Cara A. Mosley

(57) ABSTRACT

Disclosed are compounds, compositions, and methods relating to epitope-targeted immunostimulants (EPIs), which comprise a synthetic peptide ligand and an antibody-recruiting moiety. The peptide ligand binds an epitope on a target and the antibody-recruiting moiety recruits antibodies to the target when the EPI is bound to the epitope on the target. Also disclosed are compositions comprising any of the disclosed EPIs. Also disclosed are methods of stimulating an immune reaction to a microorganism or other pathogen in a subject where an EPI is administered to the subject. Also disclosed are methods of identifying the peptide ligand by using multi-omic analysis.

12 Claims, 15 Drawing Sheets

Specification includes a Sequence Listing.

(56) References Cited

FOREIGN PATENT DOCUMENTS

| | | | | |
|---|---|---|---|---|
| WO | 1998046612 | 10/1998 | | |
| WO | 1999017809 | 4/1999 | | |
| WO | 9921576 | 5/1999 | | |
| WO | 02083064 | 10/2002 | | |
| WO | 03006620 | 1/2003 | | |
| WO | 2005113762 | 12/2005 | | |
| WO | 2007050963 | 5/2007 | | |
| WO | 2009051555 | 4/2009 | | |
| WO | 2009105746 | 8/2009 | | |
| WO | 2009155420 | 12/2009 | | |
| WO | 2010135431 | 11/2010 | | |
| WO | 2011057347 | 5/2011 | | |
| WO | 2012106651 | 8/2012 | | |
| WO | 2012106671 | 8/2012 | | |
| WO | 2013009869 | 1/2013 | | |
| WO | 2013033561 | 3/2013 | | |
| WO | 2013034982 | 3/2013 | | |
| WO | WO-2014056813 A1 * | 4/2014 | ............ | C07K 14/47 |
| WO | 2014074907 | 5/2014 | | |
| WO | 2014205317 | 12/2014 | | |
| WO | 2016038565 | 3/2016 | | |
| WO | 2017011769 | 1/2017 | | |
| WO | 2017176769 | 10/2017 | | |
| WO | 2018064597 | 4/2018 | | |
| WO | WO-2018111580 A1 * | 6/2018 | ............ | A61K 45/06 |
| WO | 2018170096 | 9/2018 | | |
| WO | 2018200551 | 11/2018 | | |
| WO | 2020127227 | 6/2020 | | |

OTHER PUBLICATIONS

Alexander, et al., "Intracranial black-blood MR angiography with high-resolution 3D fast spin echo", Magn. Reson. Med., 40:298-310 (1998).
Altschul, et al., "Gapped BLAST and PSI-BLAST: a new generation of protein database search programs", Nucleic Acids Res., 25:3389-402 (1997).
Barnes, et al., "Smartphone-based pathogen diagnosis in urinary sepsis patients", EBioMedicine, 36:73-82 (2018).
Berry, et al., "Renal Sodium Gradient Orchestrates a Dynamic Antibacterial Defense Zone", Cell 170(5):860-3 (2017).
Brinkworth, et al., "Identification of Outer Membrane and Exoproteins of Carbapenem-Resistant Multilocus Sequence Type 258 Klebsiella pneumoniae", PLoS One, 10:e0123219 (2015).
Brown, et al., "Antibacterial drug discovery in the resistance era", Nature, 529:336-43 (2016).
Bunck, et al., "Modulating the Folding Landscape of Superoxide Dismutase 1 with Targeted Molecular Binders", Angew Chemie, 130:6320-3 (2018).
Cahill, et al., "Klebsiella pneumoniae O antigen loss alters the outer membrane protein composition and the selective packaging of proteins into secreted outer membrane vesicles", Microbiol Res., 180:1-10 (2015).
Claverie, "Information enhancement methods for large scale sequence analysis", Comput. Chem., 17:191-201 (1993).
Coppock, et al., "Protein Catalyzed Capture Agents with Tailored Performance for in Vitro and in Vivo Applications", Pept. Sci., 108(2):e22934 (2016).
Czaplewski, et al., "Alternatives to antibiotics—a pipeline portfolio review", Lancet. Infect. Dis., 16:239-51 (2016).
Das, et al., "A General Synthetic Approach for Designing Epitope Targeted Macrocyclic Peptide Ligands", Angew Chemie Int. Ed., 54:13219-24 (2015).
Digiandomenico, et al., "Identification of broadly protective human antibodies to Pseudomonas aeruginosa exopolysaccharide Psl by phenotypic screening", J. Exp. Med., 209(7):1273-87 (2012).
Dotiwala, et al., "Granzyme B Disrupts Central Metabolism and Protein Synthesis in Bacteria to Promote an Immune Cell Death Program", Cell, 171:1125-37 (2017).
Edelman, et al., "Extracranial carotid arteries: evaluation with "black blood" MR angiography", Radiology, 177:45-50 (1990).
Fair, et al., "Antibiotics and Bacterial Resistance in the 21st Century", Perspect. Medicin. Chem., 6:25-64. (2014).
Farrow, et al., "Epitope-Targeting of Tertiary Protein Structure Enables Target-Guided Synthesis of a Potent in Cell Inhibitor of Botulinum Neurotoxin", Angew. Chemie Int. Ed., 54(24):7114-9 (2015).
Fura, et al., "D-Amino Acid Mediated Recruitment of Endogenous Antibodies to Bacterial Surfaces", ACS Chem. Biol., 9:1480-9 (2014).
Fura, et al., "Dipeptide-Based Metabolic Labeling of Bacterial Cells for Endogenous Antibody Recruitment", ACS Infec. Dis., 2(4):302-309 (2016).
Giandomenico, et al., "A multifunctional bispecific antibody protects against Pseudomonas aeruginosa", Sci. Transl. Med., 6:262ra155 (2014).
Goodrich, et al., "A quantitative study of ramped radio frequency, magnetization transfer, and slab thickness in three-dimensional time-of-flight magnetic resonance angiography in a patient population", Invest. Radia., 31:323-32 (1996).
Guilhen, et al., "Transcriptional profiling of Klebsiella pneumoniae defines signatures for planktonic, sessile and biofilm-dispersed cells", BMC Genomics, 17:237(2016).
Hancock, et al., "Modulating Immunity as a Therapy for Bacterial Infections", Nat. Rev. Microbio., 10:243-54 (2012).
Kavvas, et al., "Machine Learning and Structural Analysis of Mycobacterium tuberculosis Pan-genome Identifies Genetic Signatures of Antibiotic Resistance", Nat. Commun., 29:4306 (2018).
Krishnamurthy, et al., "Promotion of opsonization by antibodies and phagocytosis of Gram-positive bacteria by a bifunctional polyacrylamide", Biomaterials, 27:3663-74 (2006).
Lai, et al., "Epitope Targeted Macrocyclic Peptide Ligand with Picomolar Cooperative Binding to Interleukin-17F", Chem—A Eur J., 24:3760-7 (2018).
Lee, et al., "Network Integrative Genomic and Transcriptomic Analysis of Carbapenem-Resistant Klebsiella pneumoniae Strains Identifies Genes for Antibiotic Resistance and Virulence", mSystems, 4:e00202-19 (2019).
Lorenz, et al., "Functional Antibodies Targeting IsaA of Staphylococcus aureus Augment Host Immune Response and Open New Perspectives for Antibacterial Therapy", Antimicrob. Agents Chemother., 55(1):165-73 (2011).
Lu, et al., "Beyond binding: antibody effector functions in infectious diseases", Nat. Rev. Immunol., 18:46-61 (2019).
Lu, et al., "Folate-targeted dinitrophenyl hapten immunotherapy: effect of linker chemistry on antitumor activity and allergic potential", Mol. Pharm., 4(5):2432-43 (2007).
Martin, et al., "Colonization, Infection, and the Accessory Genome of Klebsiella pneumoniae", Front Cell Infect. Microbiol., 8:4 (2018).
Mccarthy, et al., "Allosteric Inhibitor of KRas Identified Using a Barcoded Assay Microchip Platform", Anal Chem., 90:8824-30 (2018a).
Mccarthy, et al., "Phage Display of Dynamic Covalent Binding Motifs Enables Facile Development of Targeted Antibiotics", J. Am. Chem. Soc., 140:6137-45 (2018b).
Mcenaney, et al., "Antibody-Recruiting Molecules: An Emerging Paradigm for Engaging Immune Function in Treating Human Disease", ACS Chem. Biol., 7(7):1139-1151 (2012).
Meyers and Miller, "Optimal alignments in linear space", Comp. Applic. Biol. Sci., 4(1):11-17 (1988).
Murelli, et al., "Chemical Control over Immune Recognition: A Class of Antibody-Recruiting Small Molecules That Target Prostate Cancer", J. Am. Chem. Soc., 131:17090-2 (2009).
Paczosa, et al., "Klebsiella pneumoniae: Going on the Offense with a Strong Defense", Microbiol. Mol. Biol. Rev., 80:629-61 (2016).
Pelfrene, et al., "Monoclonal antibodies as anti-infective products: a promising future", Clin. Microbiol. Infect., 25:60-4 (2019).
Prevention C for DCA. Antibiotic Resistance Threats in the United States, 2013. Atlanta, Georgia; 2013.
Roope, et al., "The challenge of antimicrobial resistance: What economics can contribute", Science, 364:41 (2019).
Sabulski, et al., "Immuno-targeting of Staphylococcus aureus via surface remodeling complexes", Chem. Sci., 8:6804 (2017).

(56) References Cited

OTHER PUBLICATIONS

Saphire, et al., "Antibody-mediated protection against Ebola virus", Nat. Immunol., 19:1169-78 (2018).
Tacconelli, et al., "Discovery, research, and development of new antibiotics: the WHO priority list of antibiotic-resistant bacteria and tuberculosis", Lancet Infect. Dis., 18:318-27 (2018).
Tzouvelekis, et al., "Carbapenemases in Klebsiella pneumoniae and Other Enterobacteriaceae: an Evolving Crisis of Global Dimensions", Clin. Microbiol. Rev., 25:682-707 (2012).
Ventola, "The Antibiotic Resistance Crisis Part 1☐ Causes and Threats", Pharm. Ther., 40:277-83 (2015).
Wang, et al., "Anti-MrkA monoclonal antibodies reveal distinct structural and antigenic features of MrkA", PLoS One, 12:e017059 (2017).
Wen, et al., "G-protein-coupled formyl peptide receptors play a dual role in neutrophil chemotaxis and bacterial phagocytosis", Mol. Biol. Cell., 30:346-56 (2019).
Wootton, and Federhen, "Statistics of local complexity in amino acid sequences and sequences databases", Comput. Chem., 17(2):149-63 (1993).
Muller, et al., "Folic acid conjugates for nuclear imaging of folate receptor-positive cancer", J. Nucl. Med., 52(1): 1-4 (2011).
O'Shannessy, et al., "Characterization of the human folate receptor alpha via novel antibody-based probes", Oncotarget, 2(12):1227-1243 (2011).
Artali, et al., "A molecular dynamics study of human serum albumin binding sites", Il Farmaco, 60:485-495 (2005).
Bianchi et al., "Vaccination with peptide mimetics of the gp41 prehairpin fusion intermediate yields neutralizing antisera against HIV-1 isolates", PNAS, 107(23): 10655-10660 (2010).
Boersma, "Gaining knowledge of single carbon chains", Theory of condensed matter, Radboud Univ. Nijmegen, 18 pages (2011).
Chan, et al., "Dual-targeting anti-angiogenic cyclic peptides as potential drug leads for cancer therapy", Scientific Reports, 6:35247, 13 pages (2016).
Chattopadhyay, et al., "Techniques to improve the direct ex vivo detection of low frequency antigen-specific CD8+ T cells with peptide-major histocompatibility complex class I tetramers", Cytometry Part A, 73(11): 1001-1009 (2008).
Chauhan, et al. "The Taming of the Cell Penetrating Domain of the HIV Tat: Myths and Realities", J. Control Release, 117(2): 148-162 (2007).
Chen, et al., "Fusion protein linkers: property, design and functionality", Adv. Drug Deliv. Rev., 65(10): 1357-1369 (2013).
Cheong, et al., "A patent review of IDO1 inhibitors for cancer", Expert Opinion on Therapeutic Patents, 28(4):317-330 (2018).
Choksi, et al., "A CD8 DE loop peptide analog prevents graft-versus-host disease in a multiple minor histocompatibility antigen-mismatched bone marrow transplantation model", Biology Of Blood And Marrow Transplantation, 10(10):669-680 (2004).
Coppock, et al., "Peptide-based protein capture agents with high affinity, selectivity, and stability as antibody replacements in biodetection assays", Proc. of SPIE, 9107:910711-1 (2014).
Dieck, et al., "Development of bispecific molecules for the in situ detection of protein-protein interactions and protein phosphorylation", Cell & Biology, 21:357-368 (2014).
Eiber, et al., "Prostate-Specific Membrane Antigen Ligands for Imaging and Therapy", The Journal Of Nuclear Medicine, 58(Supplement 2):67S-76S (2017).
Fisher, et al., "Trivalent Gd-DOTA reagents for modification of proteins", RSC Adv., 5: 96194-96200 (2015).
Fitzer-Attas, et al., "Harnessing Syk family tyrosine kinases as signaling domains for chimeric single chain of the Variable Domain recept", J. Immunol., 160(1):145-154 (1998).
Gao, et al., "Crystal structure of the complex between human CD8alpha(alpha) and HLA-A2", Nature, 387:630-4 (1997).
Gen Bank: AAH25715.1, "CD8a molecule [*Homo sapiens*]" retrieved from the internet Jun. 17, 2022.
Handl, et al., "Hitting multiple targets with multimeric ligands", Expert Opin. Ther. Targets, 8(6):565-586 (2004).

Hill, et al., "Constraining Cyclic Peptides to Mimic Protein Structure Motifs", Angewandte Chemie, 53(48):13020-13041 (2014).
Hirai, et al., "MK-2206, an Allosteric Akt Inhibitor, Enhances Antitumor Efficacy by Standard Chemotherapeutic Agents or Molecular Targeted Drugs In vitro and In vivo", Molecular Cancer Therapeutics, 9(7): 1956-1967 (2010).
Hudson, et al., "Multiplex epitope mapping using bacterial surface display reveals both linear and conformational epitopes", Scientific Reports, 2(706):1-9 (2012).
Josan, et al., "Cell-specific targeting by heterobivalent ligands", Bioconjug Chem., 22(7): 1270-1278 (2011).
Lai, et al., "Epitope-Targeted Macrocyclic Peptide Ligand with Picomolar Cooperative Binding to Interleukin-17F", Chemistry, 24(15):3760-3767 (2018).
Li, et al., "Identification of the CD8 DE Loop as a Surface Functional Epitope", The J. of Biological Chem., 273(36):16422-16445 (1998).
Lin, et al., "Inhibition of HIV-1 Tat-mediated transcription by a coumarin derivative, BPRHIV001, through the Akt pathway", Journal of Virology, 85(17): 9114-9126 (2011).
Lindlsey, et al., "The P13K/Akt Pathway: Recent Progress in the Development of ATP-Competitive and Allosteric Akt Kinase Inhibitors", Current Cancer Drug Targets, 8: 7-18 (2008).
Ma, et al., "A cyclic peptide-polymer probe for the detection of Clostridium botulinum neurotoxin serotype A", Toxicon, 47(8):901-908 (2006).
Mabry, et al., "Engineering of stable bispecific antibodies targeting IL-17 A and IL-23", Protein Engineering, Design & Selection, 23(3):115-127 (2010).
Macraild et al., "Antibody Recognition of Disordered Antigens", Structure 24:148-157, (2016).
Macraild et al., "Conformational Dynamics and Antigenicity in the Disordered Malaria Antigen Merozoite Surface Protein 2", Plos One, 13 pages (2015).
Mamidyala et al., In situ click chemistry: probing the binding landscapes of biological molecules, Chemical Society Reviews, 39(4):1252-1261 (2010).
Manea, et al., "Antibody Recognition and Conformational Flexibility of a Plaque-Specific-Amyloid Epitope Modulated by Non-native Peptide Flanking Regions", J. Med. Chem., 51(5):1150-1161 (2008).
Matsuura, "Identification of conformational neutralizing epitopes on the capsid protein of canine calicivirus", Journal of General Virology, 82:1695-1702 (2001).
Melenhorst et el., "Detection of low avidity CD8(+) T cell populations with coreceptor-enhanced peptide-major histocompatibility complex class I tetramers", J Immunol Methods, 338(1-2): 31-39 (2008).
Merriam-Webster online definition of "correspond" downloaded Jun. 29, 2020 from internet, https://www.merriam-webster.com/dictionary/correspond (Year: 2020).
Millward, et al., "In situ click chemistry: from small molecule discovery to synthetic antibodies", Integr. Biol (Camb)., 5(1): 87-95 (2013).
Millward, et al., "Iterative in situ click chemistry assembles a branched capture agent and allosteric inhibitor for Akt1", JACS, 133(45):18280-18288 (2011).
Miossec, "Update on interleukin-17: a role in the pathogenesis of inflammatory arthritis and implication for clinical practice", RMD Open, 3(1): e000284 (2017).
Mor, et al., Mimicking the Structure of the V3 Epitope Bound to HIV-1 Neutralizing Antibodies, Biochemistry, 48(15):3288-3303 (2009).
Muller, et al., "DOTA Conjugate with an Albumin-Binding Entity Enables the First Folic Acid-Targeted 177Lu-Radionuclide Tumor Therapy in Mice", The Journal Of Nuclear Medicine, 54(1):124-131 (2013).
Nag et al., "A chemical epitope-targeting strategy for protein capture agents: the serine 474 epitope of the kinase Akt2", Angewandte Chemie International Edition, 52:13975-13979 (2013).
Pansca, et al., "Structural disorder in eukaryotes", PLoS One, www.plosone.org Apr. 1, 2012, 7(4): e34687, 10 pages (2012).

(56) References Cited

OTHER PUBLICATIONS

Pfeilsticker, et al., "A cocktail of thermally stable, chemically synthesized capture agents for the efficient detection of anti-gp41 antibodies from human sera", PloS One, 8(10):Article No. e76224, 5 pages (2013).
Saito, et al., "Identification of anti-CD98 antibody mimotopes for inducing antibodies with antitumor activity by mimotope immunization", Cancer Science, 105(4): 396-401 (2014).
Sarbassov, et al., "Phosphorylation and regulation of Akt/PKB by the rictor-mTOR complex", Science, American Association for The Advancement Of Science, 307(5712): 1098-1101 (2005).
Schweinsberg, et al., "Novel glycated [99mTc(CO)3]-labeled bombesin analogues for improved targeting of gastrin-releasing peptide receptor-positive tumors", Bioconjugate Chem., 19(12):2432-2439 (2008).
Son, et al., "New Cyclic Lipopeptides of the Iturin Class Produced by Saltern-Derived *Bacillus* sp. KCB14S006", Marine Drugs, 14(4): 72 (2016).
Subramanyam, et al., "Inhibition of Protein Kinase Akt1 by Apoptosis Signal-regulating Kinase-1 (ASK1) Is Involved in Apoptotic Inhibition of Regulatory Volume Increase", Journal Of Biological Chemistry, 285(9): 6109-6117(2010).
Tang et al., "Chimeric molecules facilitate the degradation of androgen receptors and repress the growth of LNCaP cells", Asian Journal of Andrology, 11(1): 119-126 (2009).
Tao, et al., "Expression, purification and identification of an immunogenic fragment in the ectodomain of prostate-specific membrane antigen", Experimental And Therapeutic Medicine, 11(3): 747-752 (2016).
Todorova, et al., "Biochemical nature and mapping of PSMA epitopes recognized by human antibodies induces after immunization with gene-based vaccines", Anticancer Research, 25: 4727-4732 (2005).
Torres, et al., "A revolutionary therapeutic approach for psoriasis: bi specific biological agents", Expert Opinion On Investigational Drugs, 25(7): 751-754 (2016).
Wang, et al., "Epitope Mapping Using Phage-Display Random Fragment Libraries", Epitope Mapping Protocols, Methods in Molecular Biology, 524: 315-332 (2009). Abstract Only.
Wang, et al., "Radioligand Therapy of Prostate Cancer with a Long-Lasting Prostate-Specific Membrane Antigen Targeting Agent 90 Y-DOTA-EB-MCG", Bioconjugate Chemistry, 29(7): 2309-2315 (2018).

Wooldridge, et al., "Tricks with tetramers: how to get the most from multimeric peptide-MHC", Immunology, 126:147-164 2009 (2009).
Zhang, et al., "Structure and function of interleukin-17 family cytokines", Protein & Cell, 2(1): 26-40 (2011).
Agalave, et al., "Click chemistry: 1,2,3-triazoles as pharmacophores", Chem. Asian J., 6:(10)2696-27018 (2011).
Almehdi, et al., "SARS-CoV-2 spike protein: pathogenesis, vaccines, and potential therapies", Infection, 49: 855-876 (2021).
BPS Bisoscience: INCB024360 Analog Data Sheet (2012).
Glaven, "Linking Single Domain Antibodies that Recognize Different Epitopes on the Same Target", Biosensors, 2:43-56 (2012).
He, et al., "Vaccine design based on 16 epitopes of SARS-CoV-2 spike protein", Journal of Medical Virology, 93:2115-2131 (2021).
Kirszbaum, et al., "The alpha-chain of murine CD8 lacks an invariant Ig-like disulfide bond but contains a unique intrachain loop instead", J. Immunol., 142(11):3931-6 (1989).
Koonin, et al., "Sequence—Evolution—Function: Computational Approaches in Comparative Genomics", Boston: Kluwer Academic; 2003, Chapter 2 Evolutionary Concept in Genetics and Genomics (2003).
Reeck, et al., "Homolgy' in Proteins and Nucleic Acids: A Terminology Muddle and a Way out of it", Cell, 50:667 (1987).
Smith, et al., "Zinc mediated azide-alkyne ligation to 1,5- and 1,4,5-substituted 1,2,3-triazoles", Org. Lett., 15(18):4826-4829 (2013).
Sormanni, et al., "Rational design of antibodies targeting specific epitopes within intrinsically disordered proteins", PNAS, 112(32):9902-9907 (2015).
Sormanni, etal., "Supporting Information", PNAS, 112(32):1-10 (2015). Supplemental Materials.
Testa, et al., "CD 123 is a membrane biomarker and a therapeutic target in hematologic malignancies", Biomarker Research, 2:4 (2014).
Wang, et al., "Structural basis of the CD8 alpha beta/MHC class I interaction: focused recognition orients CD8 beta to a T cell proximal position", J. Immunol., 183(4):2554-64 (2009).
Yang, et al., "Structural biology of SARS-CoV-2 and implications for therapeutic development", Nature Reviews, 19:685-700 (2021).
Nakano et al., "Amino Acid Sequence of Cytochrome C-553 from Desulfovibrio vulgaris Miyazaki" vol. 258 No. 20 Issue of Oct. 25 pp. 12409-12412(1983).
Murphy et al,. "Janeway's Immunobiology, 9th edition", pp. 150-151 (2017).

\* cited by examiner

SEQUENCE LISTING

```
<160> NUMBER OF SEQ ID NOS: 87

<210> SEQ ID NO 1
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 1

Phe Phe Gly Lys Val Thr Asp Val Ser Cys Thr Val Ser Val
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 2

Thr Glu Val Lys Ala Ala Ala Ala Asp Thr Tyr Leu Lys Pro
1               5                   10
```

```
<210> SEQ ID NO 3
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 3

Ala Thr Ser Lys Gln Gln Gly Tyr Leu Ala Asn Thr Glu Ala
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 4

Ser Thr Gln Pro Lys Ala Lys Gly Asp Ala Ser Ala Val Ala
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 5

Leu Leu Phe Phe Phe
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 6

His Tyr Glu Trp Leu
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 7

Ala Leu Phe Phe Phe
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 8

Leu Ala Phe Phe Phe
1               5

<210> SEQ ID NO 9
```

```
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 9

Leu Leu Ala Phe Phe
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 10

Leu Leu Phe Ala Phe
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 11

Leu Leu Phe Phe Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 12

Asp Leu Phe Phe Phe
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 13

His Leu Phe Phe Phe
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 14

Ala Ala Phe Phe Phe
1               5

<210> SEQ ID NO 15
<211> LENGTH: 8
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: Cyclic peptide

<400> SEQUENCE: 15

Leu Leu Phe Phe Phe Arg Arg Arg
1               5

<210> SEQ ID NO 16
<211> LENGTH: 11
<212> TYPE: PRT
<213> ORGANISM: Artificial Sequence
<220> FEATURE:
<223> OTHER INFORMATION: Artificial Sequence
<220> FEATURE:
<221> NAME/KEY: MISC_FEATURE
<222> LOCATION: (1)..(5)
<223> OTHER INFORMATION: CYCLIC PEPTIDE

<400> SEQUENCE: 16

Leu Leu Phe Phe Phe Arg Arg Arg Arg Arg Arg
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: CYCLIC PEPTIDE

<400> SEQUENCE: 17

Leu Leu Phe Phe Phe Arg Arg Arg Arg Arg Arg Arg Arg
1               5                   10

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 18

His Asn Gly Pro Thr
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 19

Ala Thr His Ser Leu
1               5

<210> SEQ ID NO 20
```

```
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (2)..(2)
<220> FEATURE:
<221> NAME/KEY: D-amino acid
<222> LOCATION: (4)..(5)

<400> SEQUENCE: 20

Gly Asn Gly Asp Val
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 21

Pro Lys Asp Glu Trp
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 22

Lys Pro Glu Asp Trp
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 23

Lys Pro Asp Glu Trp
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: D-amino acid
<222> LOCATION: (5)..(5)
```

```
<400> SEQUENCE: 24

Pro Glu Glu Gly Thr
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)

<400> SEQUENCE: 25

Glu Val Glu Thr Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 26

Lys Ala Asp His Pro
1               5

<210> SEQ ID NO 27
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)

<400> SEQUENCE: 27

Lys Asn Asp Pro
1

<210> SEQ ID NO 28
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (2)..(5)

<400> SEQUENCE: 28

Gly Leu His Thr Asp
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)
```

```
<400> SEQUENCE: 29

Ser Asp Leu Pro Arg
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 30

Pro Asp Glu Asp Trp
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(1)
<220> FEATURE:
<221> NAME/KEY: D-amino acid
<222> LOCATION: (3)..(5)

<400> SEQUENCE: 31

Ala Gly Pro Val Glu
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(2)
<220> FEATURE:
<221> NAME/KEY: D-amino acid
<222> LOCATION: (5)..(5)

<400> SEQUENCE: 32

Ala Lys Gly Gly Pro
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(1)
<220> FEATURE:
<221> NAME/KEY: D-amino acid
<222> LOCATION: (3)..(3)
<220> FEATURE:
<221> NAME/KEY: D-amino acid
<222> LOCATION: (5)..(5)

<400> SEQUENCE: 33
```

Ala Gly Lys Gly Pro
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 34

Ala Lys Lys Arg Pro
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 35

Thr Thr Phe Phe Phe
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: Xaa is 4-fluoro-phenylalanine

<400> SEQUENCE: 36

Leu Leu Phe Phe Xaa
1               5

<210> SEQ ID NO 37
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 37

Leu Phe Phe Phe
1

<210> SEQ ID NO 38
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = azidolysine
<222> LOCATION: (8)..(8)

<400> SEQUENCE: 38

Phe Phe Gly Lys Val Thr Asp Xaa Ser Cys Thr Val Ser Val
1               5                   10

```
<210> SEQ ID NO 39
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = azidolysine
<222> LOCATION: (7)..(7)

<400> SEQUENCE: 39

Thr Glu Val Lys Ala Ala Xaa Ala Asp Thr Tyr Leu Lys Pro
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = azidolysine
<222> LOCATION: (9)..(9)

<400> SEQUENCE: 40

Ala Thr Ser Lys Gln Gln Gly Tyr Xaa Ala Asn Thr Glu Ala
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Artificial Sequence
<220> FEATURE:
<221> NAME/KEY: Xaa = azidolysine
<222> LOCATION: (6)..(6)

<400> SEQUENCE: 41

Ser Thr Gln Pro Lys Xaa Lys Gly Asp Ala Ser Ala Val Ala
1               5                   10

<210> SEQ ID NO 42
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 42

Phe Tyr Thr Lys Gly
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 43

Glu Tyr Glu Gly Lys
1               5

<210> SEQ ID NO 44
<211> LENGTH: 5
<212> TYPE: PRT
<213> ORGANISM: Artificial Sequence
<220> FEATURE:
```

<223> OTHER INFORMATION: Synthetic Peptide

<400> SEQUENCE: 44

Pro Trp Asn Lys Gly
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 45

Ser Trp Thr Gly Glu
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 46

Arg His Pro Gly Glu
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 47

Asn Arg Thr Gly Pro
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 48

Pro Arg Glu Gly Pro
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 49

Ser Asn Phe Gly Pro
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 50

Glu Lys Thr Pro Gly
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 51

Lys Gly Phe Pro Gly
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 52

Gly Gly Phe Asn Ala
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 53

Asn Gly Pro Val His
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 54

Trp Tyr Lys Gly Pro
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 55

Trp Asp Tyr Lys Gly
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic Peptide

```
<400> SEQUENCE: 56

Tyr Arg His Leu Gly
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 57

Gly Val His Arg Leu
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 58

Gly Val Val Glu Lys
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 59

Gly Leu Thr His Ala
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 60

Ser Leu Gly Leu Thr
1               5

<210> SEQ ID NO 61
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 61

Lys Pro Ala Gly
1

<210> SEQ ID NO 62
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 62
```

```
Ala Lys Pro Glu Pro
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 63

Glu Trp Val Ser Ala
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 64

Glu Phe Ser Gly Val
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 65

Asp Gly Thr Ala Leu
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 66

Val Val Asn Leu Pro
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 67

Thr Pro Asn Leu Pro
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 68
```

-continued

```
Arg Pro Glu Gly Pro
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: D-amino acid
<222> LOCATION: (5)..(5)

<400> SEQUENCE: 69

Phe Asp Glu Gly Glu
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: D-amino acid
<222> LOCATION: (5)..(5)

<400> SEQUENCE: 70

Phe Asp Glu Gly Pro
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: D-amino acid
<222> LOCATION: (5)..(5)

<400> SEQUENCE: 71

Leu Asp Glu Gly Pro
1               5

<210> SEQ ID NO 72
<211> LENGTH: 202
<212> TYPE: PRT
<213> ORGANISM: Klebsiella pneumoniae

<400> SEQUENCE: 72

Met Lys Lys Val Leu Leu Ser Ala Ala Met Ala Thr Ala Phe Phe Gly
1               5                   10                  15

Met Thr Ala Ala His Ala Ala Asp Thr Thr Val Gly Gly Gly Gln Val
                20                  25                  30

Asn Phe Phe Gly Lys Val Thr Asp Val Ser Cys Thr Val Ser Val Asn
            35                  40                  45

Gly Gln Gly Ser Asp Ala Asn Val Tyr Leu Ser Pro Val Thr Leu Thr
        50                  55                  60
```

```
Glu Val Lys Ala Ala Ala Asp Thr Tyr Leu Lys Pro Lys Ser Phe
 65                  70                  75                  80

Thr Ile Asp Val Ser Asn Cys Gln Ala Ala Asp Gly Thr Lys Gln Asp
                 85                  90                  95

Asp Val Ser Lys Leu Gly Val Asn Trp Thr Gly Gly Asn Leu Leu Ala
            100                 105                 110

Gly Ala Thr Ser Lys Gln Gln Gly Tyr Leu Ala Asn Thr Glu Ala Ser
        115                 120                 125

Gly Ala Gln Asn Ile Gln Leu Val Leu Ser Thr Asp Asn Ala Thr Ala
    130                 135                 140

Leu Thr Asn Lys Ile Ile Pro Gly Asp Ser Thr Gln Pro Lys Ala Lys
145                 150                 155                 160

Gly Asp Ala Ser Ala Val Ala Asp Gly Ala Arg Phe Thr Tyr Tyr Val
                165                 170                 175

Gly Tyr Ala Thr Ser Ala Pro Thr Thr Val Thr Thr Gly Val Val Asn
            180                 185                 190

Ser Tyr Ala Thr Tyr Glu Ile Thr Tyr Gln
        195                 200

<210> SEQ ID NO 73
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 73

Leu Leu Phe Phe
1

<210> SEQ ID NO 74
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (7)..(7)
<223> OTHER INFORMATION: X is Azidolysine

<400> SEQUENCE: 74

Xaa Leu Leu Phe Phe Phe Xaa
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (7)..(7)
<223> OTHER INFORMATION: X is Azidolysine

<400> SEQUENCE: 75
```

Xaa Ala Leu Phe Phe Phe Xaa
1               5

<210> SEQ ID NO 76
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (7)..(7)
<223> OTHER INFORMATION: X is Azidolysine

<400> SEQUENCE: 76

Xaa Leu Ala Phe Phe Phe Xaa
1               5

<210> SEQ ID NO 77
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (7)..(7)
<223> OTHER INFORMATION: X is Azidolysine

<400> SEQUENCE: 77

Xaa Leu Leu Ala Phe Phe Xaa
1               5

<210> SEQ ID NO 78
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (7)..(7)
<223> OTHER INFORMATION: X is Azidolysine

<400> SEQUENCE: 78

Xaa Leu Leu Phe Ala Phe Xaa
1               5

<210> SEQ ID NO 79
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X is Azidolysine
<220> FEATURE:

```
<221> NAME/KEY: MOD_RES
<222> LOCATION: (7)..(7)
<223> OTHER INFORMATION: X is propargylglycine

<400> SEQUENCE: 79

Xaa Leu Leu Phe Phe Ala Xaa
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (7)..(7)
<223> OTHER INFORMATION: X is Azidolysine

<400> SEQUENCE: 80

Xaa Ala Ala Phe Phe Phe Glx
1               5

<210> SEQ ID NO 81
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (6)..(6)
<223> OTHER INFORMATION: X is Azidolysine

<400> SEQUENCE: 81

Xaa Leu Phe Phe Phe Xaa
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (7)..(7)
<223> OTHER INFORMATION: X is azidonorvaline

<400> SEQUENCE: 82

Xaa Leu Leu Phe Phe Phe Xaa
1               5

<210> SEQ ID NO 83
<211> LENGTH: 7
<212> TYPE: PRT
<213> ORGANISM: Artificial sequence
<220> FEATURE:
<223> OTHER INFORMATION: Synthetic Peptide
```

```
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (6)..(6)
<223> OTHER INFORMATION: X is 4-fluoro-phenylalanine
<220> FEATURE:
<221> NAME/KEY: MOD_RES
<222> LOCATION: (7)..(7)
<223> OTHER INFORMATION: Z is Azidolysine

<400> SEQUENCE: 83

Xaa Leu Leu Phe Phe Xaa Xaa
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (7)..(7)
<223> OTHER INFORMATION: X is Azidolysine

<400> SEQUENCE: 84

Xaa Thr Thr Phe Phe Phe Xaa
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (7)..(7)
<223> OTHER INFORMATION: X is Azidolysine

<400> SEQUENCE: 85

Xaa His Leu Phe Phe Phe Glx
1               5

<210> SEQ ID NO 86
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (7)..(7)
<223> OTHER INFORMATION: X is Azidolysine

<400> SEQUENCE: 86

Xaa Asp Leu Phe Phe Phe Xaa
```

```
<210> SEQ ID NO 87
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X is propargylglycine
<220> FEATURE:
<221> NAME/KEY: MOD_RES
<222> LOCATION: (6)..(6)
<223> OTHER INFORMATION: X is Azidolysine

<400> SEQUENCE: 87

Xaa Leu Leu Phe Phe Xaa
1               5
```

EPITOPE-TARGETED PEPTIDE IMMUNOSTIMULANTS

CROSS-REFERENCE TO RELATED APPLICATIONS

This application claims benefit of U.S. Provisional Application No. 62/830,193, filed Apr. 5, 2019. Application No. 62/830,193, filed Apr. 5, 2019, is hereby incorporated herein by reference in its entirety.

STATEMENT REGARDING FEDERALLY SPONSORED RESEARCH

This invention was made with government support under AI138258 and AI128215 awarded by the National Institutes of Health, W911NF-09-D-0001 awarded by the U.S. Army Research Office, and 1565166 awarded by the National Science Foundation. The government has certain rights in the invention.

REFERENCE TO SEQUENCE LISTING

The Sequence Listing submitted as a text file named "REGN_105_US_ST25.txt" created on May 31, 2024, and having a size of 20,675 bytes is hereby incorporated by reference pursuant to 37 C.F.R. § 1.825 (b) (2).

FIELD OF THE INVENTION

The disclosed invention is generally in the field of immunostimulation and vaccines and specifically in the area of epitope-targeted immunostimulation.

BACKGROUND OF THE INVENTION

Antibiotic resistant infections are projected to cause over 10 million deaths by 2050, yet the development of new antibiotics has slowed. This points to an urgent need for methodologies for the rapid development of antibiotics against emerging drug resistant pathogens. The emergence of antibiotic-resistant bacteria represents a major threat to human health (1-4), with both increasing mortality rates and costs of care (5-8). Widespread overuse and misuse of traditional antibiotics has enabled bacteria to evolve immunity against many or all available antibiotic therapies. These difficult-to-drug or "undruggable" multi-resistant bacteria already account for a substantial death-toll and increased cost of care (6, 89). One example is carbapenem-resistant *Klebsiella pneumoniae* (*K. pneumoniae*) strains that harbor resistance against many or all antibiotics (1, 6, 9, 10) and frequently cause hospital-acquired infections (11) with high mortality rates (12). Compounding the general problem of antibiotic resistance are challenges in developing and approving new antibiotics (13). This has spurred research into understanding resistance mechanisms (14, 15), host defenses (16-18), diagnostics (19) and antibiotic generation (20, 21). Ultimately, without a rapid and perhaps general method to develop new targeted antibiotics, therapies might relapse towards those of the pre-antibiotic era (4, 13).

Protein-catalyzed capture (PCCs) are an emerging class of epitope-targeted peptide ligands that can be rapidly adapted to bacterial protein targets. PCCs are developed against specific epitopes by employing non-catalyzed in situ click chemistry to assay a combinatorial library PCCs for binding to a desired epitope (42). PCCs yielded by a single-generation screen exhibit affinities from 10 µM to 500 picomolar to the target protein, while affinity can be improved by linking PCCs to form biligands that co-operatively bind a target protein (44). PCCs can be developed against a new target in under a month, and have high thermal stabilities that would enable PCCs to be transported to remote locations under inclement conditions without loss of efficacy (91).

Immunomodulation by synthetic molecules is an emerging therapeutic strategy to combat bacterial and fungal infections (22-25), as well as other human diseases including cancer (26, 27). The guiding principle is to employ an immunogenic agent to elicit a targeted immune response against a particular pathogen. The archetypical immune agent is an antibody and, while many therapeutic antibodies neutralize pathogens by direct interaction, a few operate by enhancing immune responses against the antibody target (22, 28). Examples include antibodies against the Ebola virus (29), *Staphylococcus aureus* (30), *Pseudomonas aeruginosa* (28, 31), and *K. pneumoniae* (32, 33). While effective, antibodies can be challenging to produce and globally distribute at scale (34, 35). Alternative compelling strategies include employing synthetic molecules that bind bacterial surface proteins (36, 37) or peptidoglycans (36, 38), and present haptens so as to recruit the native immune system to promote bacterial clearance. Other synthetic approaches include metabolically incorporating non-native haptens into bacterial surface components (39, 40). While inexpensive and scalable, these technologies can be challenging to adapt to different pathogens, or they can be non-selective, raising concerns about deleterious off-target effects.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

BRIEF SUMMARY OF THE INVENTION

Disclosed are compounds, compositions, and methods relating to epitope-targeted immunostimulants (EPIs). Disclosed are EPIs comprising a synthetic peptide ligand and an antibody-recruiting moiety, where the peptide ligand and the antibody-recruiting moiety are conjugated or coupled together. In some forms, the peptide ligand has affinity for an epitope on a target molecule comprised in a target. In some forms, the epitope is exposed on the surface of the target. In some forms, the antibody-recruiting moiety recruits antibodies to the target when the EPI is bound to the epitope on the target.

In some forms, the peptide ligand is cyclic.

In some forms, the peptide ligand comprises a 1,4-substituted-1,2,3-triazole residue (Tz4) or a 1,5-substituted-1,2,3-triazole residue (Tz5). In some forms, the peptide ligand comprises a 1,4-substituted-1,2,3-triazole residue (Tz4). In some forms, the peptide ligand comprises a 1,5-substituted-1,2,3-triazole residue (Tz5).

In some forms, the peptide ligand was identified by non-catalyzed in situ click chemistry screening of a combinatorial peptide library.

In some forms, the target is a microorganism. In some forms, the microorganism is an infectious microorganism. In some forms, the microorganism is a bacterium or a fungal cell. In some forms, the microorganism is a Gram-negative bacterium. In some forms, the microorganism is in the genus *Klebsiella, Salmonella, Escherichia, Staphylococcus, Legio-* nella, *Pseudomonas, Haemophilus, Helicobacter, Vibrio, Acinetobacter, Bordetella, Campylobacter, Citrobacter, Enterobacter, Serratia, Shigella, Yersinia,* or *Neisseria.* In some forms, the microorganism is in the species *Klebsiella* spp., *Salmonella* spp., *Escherichia coli, Staphylococcus* spp., *Legionella pneumophila, Pseudomonas aeruginosa, Haemophilus influenza, Helicobacter pylori, Vibrio cholerae, Acinetobacter* spp., *Bordetella pertussis, Campylobacter* spp., *Citrobacter* spp., *Enterobacter* spp., *Serratia marcescens, Shigella* spp., *Yersinia* spp., or *Neisseria* spp.

In some forms, the microorganism is *Klebsiella pneumoniae.* In some forms, the microorganism is *Staphylococcus aureus.* In some forms, the microorganism is in the family Enterobacteriaceae.

In some forms, the target is a virus. In some forms, the virus is an influenza virus or a coronavirus.

In some forms, the target molecule is MrkA protein. In some forms, the epitope has the amino acid sequence TEVKAAAADTYLKP (SEQ ID NO:2). In some forms, the peptide ligand comprises the amino acid sequence LLFFF (SEQ ID NO:5).

In some forms, the target molecule is *Staphylococcus aureus* peptidoglycan. In some forms, the target molecule is methicillin-resistant *Staphylococcus aureus* peptidoglycan. In some forms, the peptide ligand comprises the amino acid sequence kpdew (SEQ ID NO:23) or akkrp (SEQ ID NO:34).

In some forms, the antibody-recruiting moiety comprises an epitope recognized by an antibody that mediates recognition and phagocytosis of the target by an immune cell. In some forms, the epitope recognized by an antibody that mediates recognition and phagocytosis of the target by an immune cell is an immunogen endogenously recognized by a mammalian immune system. In some forms, the epitope recognized by an antibody that mediates recognition and phagocytosis of the target by an immune cell is an immunogen endogenously recognized by a human immune system.

In some forms, the epitope recognized by an antibody that mediates recognition and phagocytosis of the target by an immune cell is 2,4-dinitrophenyl (DNP), alpha-galactose, galactose (alpha1-3) galactose, beta-lactam, 1,3-diketone, avidin, fluorescein, fluorescein-DNP, or nitrophenol.

In some forms, the peptide ligand is comprised in a multi-ligand, wherein the multi-ligand further comprises a second ligand, wherein the second ligand has affinity for a second epitope on the target molecule, wherein the second epitope is exposed on the surface of the target, wherein the peptide ligand and the second ligand are covalently linked to each other, wherein the multi-ligand can simultaneous bind to the epitope and to the second epitope on the target molecule.

Also disclosed are compositions comprising any of the disclosed EPIs.

Also disclosed are methods of stimulating an immune reaction to a microorganism or other pathogen in a subject, the method comprising administering an EPI to the subject, wherein the microorganism or other pathogen in the subject is the target of the EPI of the composition.

In some forms, the microorganism in the subject is resistant to one or more antibiotics. In some forms, the microorganism in the subject is resistant to one or more classes of antibiotics. In some forms, the microorganism in the subject is multidrug-resistant. In some forms, the microorganism is a bacterium or a fungal cell. In some forms, the microorganism is a Gram-negative bacterium. In some forms, the microorganism is in the genus *Klebsiella, Salmonella, Escherichia, Staphylococcus, Legionella, Pseudomonas, Haemophilus, Helicobacter, Vibrio, Acinetobacter, Bordetella, Campylobacter, Citrobacter, Enterobacter, Serratia, Shigella, Yersinia,* or *Neisseria.* In some forms, the microorganism is in the species *Klebsiella* spp., *Salmonella* spp., *Escherichia coli, Staphylococcus* spp., *Legionella pneumophila, Pseudomonas aeruginosa, Haemophilus influenza, Helicobacter pylori, Vibrio cholerae, Acinetobacter* spp., *Bordetella pertussis, Campylobacter* spp., *Citrobacter* spp., *Enterobacter* spp., *Serratia marcescens, Shigella* spp., *Yersinia* spp., or *Neisseria* spp.

In some forms, the microorganism is *Klebsiella pneumoniae.* In some forms, the microorganism is *Staphylococcus aureus.* In some forms, the microorganism is in the family Enterobacteriaceae.

Also disclosed are methods of identifying the peptide ligand, the method comprising:
 (a) selecting a protein that is highly expressed in a target microorganism and that at least a part of is exposed on the surface of the microorganism, wherein the selected protein is the target molecule;
 (b) selecting an epitope by identifying amino acid sequences of the selected protein that are predicted both to be surface-exposed and to have a low homology to the human proteome relative to other amino acid sequences of the selected protein and selecting one of the identified amino acid sequences as the epitope;
 (c) contacting a polypeptide fragment with a plurality of candidate peptides, wherein the polypeptide fragment comprises the epitope, wherein the epitope is modified or substituted with (i) a group comprising an azido or alkynyl group and (ii) a label, wherein the candidate peptides all comprise an alkynyl group if the epitope has an azido group or an azido group if the epitope has an alkynyl group; and
 (d) incubating the polypeptide fragment and the candidate peptides to allow formation of a triazole linkage between the polypeptide fragment and one of the candidate peptides, wherein a candidate peptide that forms a triazole linkage with the polypeptide fragment is identified as the peptide ligand.

In some forms, the group comprising an azido or alkynyl group is an artificial amino acid. In some forms, the artificial amino acid is propargylglycine (Pra). In some forms, the epitope comprises a phosphorylated amino acid, wherein the group comprising an azido or alkynyl group is a metalorganic molecule that selectively binds to the phospho group on the phosphorylated amino acid. In some forms, the metalorganic molecule comprises the label. In some forms, the label is biotin. In some forms, the metalorganic molecule comprises an azido group.

In some forms, the method further comprises: selecting a candidate peptide linked to the polypeptide fragment via a triazole linkage as the peptide ligand; and sequencing the peptide ligand. In some forms, the candidate peptide is selected by selecting labeled candidate peptides. In some forms, the method further comprises testing the peptide ligand for binding to the target molecule.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 2A is a flow diagram illustrating the multi-omic-driven approach for selecting a protein target on *K. pneumoniae* for EPIs (AR-PCCs): analysis of transcriptomic and proteomic data identified highly expressed surface proteins of *K. pneumoniae*. Among those proteins, MrkA was targeted due to its association with virulence and extracellular localization (literature review). FIG. 2B is a plot of predicted surface-exposure, maximum homology with the human proteome ("Maximum homology"), and antigenicity ("Antigen"), for all 14-residue epitopes of MrkA, as derived from bioinformatics tools (NetSurfP-2.0 (57), BepiPred 2.0 (58), and BLAST, using parameters defined in reference 59. Arrows indicate the locations of four 14-residue epitopes with high-exposure and low-homology that were selected as targets. The sequences of these epitopes are shown above the plot: FFGKVTDVSCTVSV (SEQ ID NO: 1), TEVKAAAADTYLKP (SEQ ID NO:2), ATSKQQGYLANTEA (SEQ ID NO: 3), STQPKAKGDASAVA (SEQ ID NO:4).

FIG. 4A is a graph depicting sandwich ELISA results of an alanine scan of cy(LLFFF) (SEQ ID NO:5), which interrogates the affinity of alanine-substituted cy(LLFFF) (SEQ ID NO:5) analogues to full-length MrkA protein. The sequences are, from left to right, cy(LLFFF) SEQ ID NO:5, cy(ALFFF) SEQ ID NO:7, cy(LAFFF) SEQ ID NO:8, cy(LLAFF) SEQ ID NO:9, cy(LLFAF) SEQ ID NO:10, and cy(LLFFA) SEQ ID NO:11. FIG. 4B is a plot of the isocratic point versus affinity to MrkA protein, relative to cy(LLFFF) (SEQ ID NO:5), for various cy(LLFFF) (SEQ ID NO:5) analogues in which residues were either substituted or removed, or an N-terminal tag was appended. The sequences are cy(LLFFF) SEQ ID NO: 5, cy(LLFF) SEQ ID NO:73, cy(LLF), cy(LFFF) SEQ ID NO:37, cy(FFF), cy(ALFFF) SEQ ID NO:7, cy(LAFFF) SEQ ID NO:8, cy(LLFAF) SEQ ID NO:10, cy(LLFFA) SEQ ID NO: 11, cy(DLFFF) (SEQ ID NO: 12), cy(HLFFF) (SEQ ID NO:13), cy(AAFFF) (SEQ ID NO:14), cy(LLFFF)+R3 (SEQ ID NO:15), cy(LLFFF)+R6 (SEQ ID NO: 16), and cy(LLFFF)+R9 (SEQ ID NO:17). Modifications generally reduced the isocratic point but also reduced binding, with the exception an N-terminal hexa-arginine tag (cy(LLFFF)+R6; SEQ ID NO:16). This compound also bound MrkA protein in solutions of 10 and 100% mouse sera, albeit at lower levels versus 0% serum (inset). The relative affinities plotted in FIG. 4B are the ratio of ELISA signals yielded by the analogue to those produced by an cy(LLFFF) (SEQ ID NO:5) reference on the same ELISA plate. All ELISA data are background corrected to signal from an otherwise identical measurement except with biotin-peg6 conjugated instead of the PCC. Error bars are standard deviations. Each PCC used here had an N-terminal Biotin-peg group.

FIG. 5A is a schematic illustration of a whole-cell ELISA affinity test in which *K. pneumoniae* was incubated with PCCs conjugated with biotin, opsonized with streptavidin-HRP, and then detected colorimetrically. FIG. 5B is a graph of whole-cell ELISA results showing that biotinylated cy(LLFFF) (SEQ ID NO:5) binds wild type MrkA-expressing KPPR1 cells (solid orange bars), but not MrkA-knockout KPPR1 (dashed orange bars) cells that do not produce MrkA. Much lower binding is observed from the highly homologous control compound cy(LLFFA) (SEQ ID NO:11) (solid and dashed blue lines). Western blots of wild type and MrkA-knockout KPPR1 cells are shown in the inset. FIG. 5C is a graph of cell-binding ELISA results showing that biotinylated cy(LLFFF) (SEQ ID NO:5) at 5 μM binds two strains of MrkA-expressing *K. pneumoniae* cells with excellent selectivity versus *E. coli* and *S. typhimurium*. By comparison a biotinylated dummy ligand cy(HNGPT) (SEQ ID NO:18), and cy(LLFFA) (SEQ ID NO:11) shows no or minimal binding above baseline. Asterisks (*) indicate ELISA data for target *K. pneumoniae* strains, and error bars reflect standard deviations.

FIG. 7A is a flow diagram depicting the assay used to evaluate EPI-driven opsonophagocytic killing (OPK) of *K. pneumoniae* cells. Briefly, *K. pneumoniae* cells (strain BAA 1705) opsonized by EPIs (AR-PCCs) and anti-DNP antibodies were incubated with macrophages for 1 or 24 h. Macrophages were lysed, and the lysate was plated to obtain bacterial colonies that were subsequently counted. FIG. 7B is a plot of colony counts for various samples subjected to the OPK assay. At 1 h, all controls (the six leftmost samples) showed basal-level CFU counts at around 38,000 CFU, while *K. pneumoniae* cells treated with lead EPI (AR-PCC) cy(LLFFF)-DNP (SEQ ID NO: 5), cy(LLFFA) (SEQ ID NO:11), or cy(LLFFF)+R6-DNP (SEQ ID NO: 16) plus anti-DNP antibody produced much higher 85,000 CFU, establishing cy(LLFFF)-DNP (SEQ ID NO: 5) promotes opsonization. This level of phagocytosis is comparable to that promoted by *K. pneumoniae* antiserum and anti-MrkA antibody (at dilutions stated in the Examples), which yielded approximately 100,000 CFU. Almost no CFU were produced from any samples harvested at 24 h, indicating that EPIs (AR-PCCs) did not interfere with OPK activity. All EPIs (AR-PCCs) were used at a 5 μM concentration, measurements were conducted in triplicate, and error bars reflect standard deviations.

FIG. 11A shows strong absorbances from samples treated with biotinylated cy(LLFFF) (SEQ ID NO: 5) at concentrations from 5 μM to 5 nM (solid orange bars), while near-baseline absorbances are observed from cells cultured in LB (orange dashed bars). Thus, cy(LLFFF) (SEQ ID NO:5) preferentially binds MrkA-expressing cells. By comparison, both wild type and MrkA-knockout samples treated with cy(LLFFA) (SEQ ID NO:11) at all concentrations tested yield near-baseline absorbances (solid and striped blue bars), indicating nearly no binding. FIG. 11B is a graph showing that cells cultured in either LB or G-CAA that were treated at higher 50 μM concentrations of cy(LLFFF) (SEQ ID NO: 5) and cy(LLFFA) (SEQ ID NO:11) produce strong and comparable ELISA signals, demonstrating that both compounds bind *K. pneumoniae* cells regardless of MrkA-expression. Such binding may occur through non-specific hydrophobic type interactions with cell surface components.

DETAILED DESCRIPTION OF THE INVENTION

The disclosed method and compositions can be understood more readily by reference to the following detailed description of particular embodiments and the Example included therein and to the Figures and their previous and following description.

Figure 1:
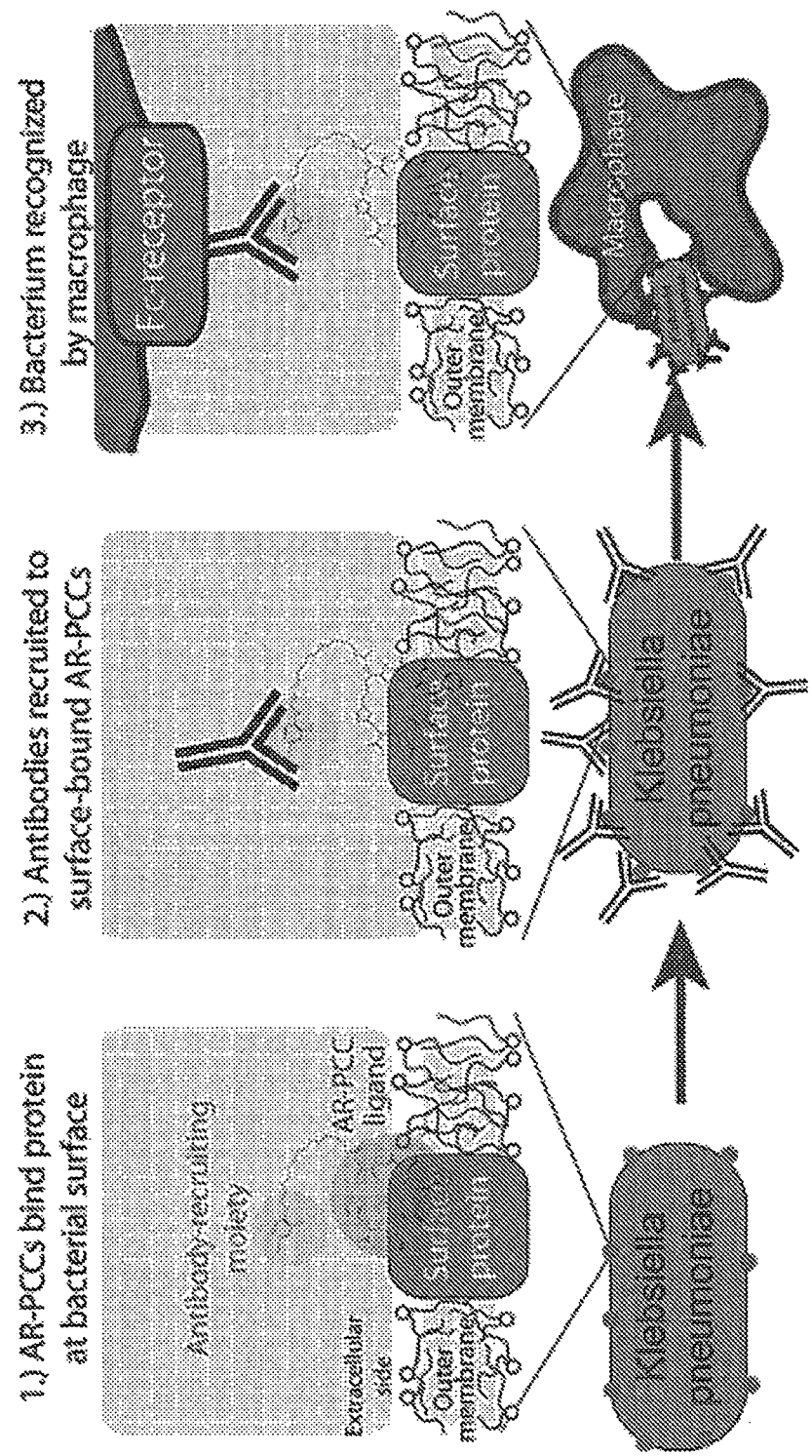
FIG. 1 is a schematic depicting the mode-of-action of AR-PCCs against antibiotic-resistant *Klebsiella pneumoniae*. EPI (AR-PCC) molecules (1) bind to a surface protein on a *K. pneumoniae* bacterium, then (2) recruit antibodies that opsonize the bacterium, which leads to (3) recognition and phagocytosis of the bacterium by immune cells (e.g., macrophages).

It was realized that a new class of highly targeted antibiotics could be made that combined immunostimulation with specific targeting of a target. Called epitope-targeting immunostimulants (EPIs), these contain a ligand to an epitope on a target and an antibody-recruiting molecule (ARM). A particular form of EPI called antibody-recruiting protein-catalyzed capture agents (AR-PCC) was demonstrated, and it was realized that these could be rapidly developed against a specified drug-resistant bacterium (FIG. 1). AR-PCCs consist of two molecular motifs. The first is a macrocyclic polypeptide ligand (the PCC) developed against a designated epitope of a specific surface protein on a microbial or viral target. The second is an antibody-recruiting (AR) label on the PCC that promotes phagocytosis of the pathogen by innate immune cells (FIG. 1). To generate the AR-PCC ligand, the recently reviewed (41), all synthetic epitope-targeted protein-catalyzed capture agent (PCC) method (42-45) was used and coupled with a bioinformatics approach to identify epitopes for targeting. By targeting highly exposed, antigenic epitopes of the Type 3 Fimbrial Shaft (MrkA) surface protein of *K. pneumoniae*, a small macrocyclic peptide binder was developed in a single generation screen. That binder exhibits high affinity for the MrkA protein, high selectivity for carbapenem-resistant *K. pneumoniae*, and, when labeled with the AR tag, promotes macrophage-mediated phagocytosis of the pathogen. This work demonstrates that AR-PCCs can be used to target multi-drug resistant *K. pneumoniae*, and that the basic technology provides a route towards drugging "undruggable" pathogenic bacteria.

Described herein is an all-new class of antibiotics called epitope-targeted immunostimulants (EPIs) that can be rapidly generated against a specified drug-resistant bacterium. EPI molecules consist of two molecular motifs: (1) a synthetic macrocyclic PCC polypeptide ligand that binds to a bacterial surface protein and (2) an immunogenic moiety that recruits antibodies to the cell surface. EPIs adsorb to the surfaces of the targeted bacteria, promote opsonization, and ultimately enhance phagocytic killing by innate immune cells, as shown in FIG. 1. The importance of EPIs is that they can be adapted to target any bacterium, enabling them to serve as antibiotics against any type of bacteria, including antibiotic-resistant bacteria for which there are little or no therapeutic options. The novelty of EPIs is the combination of an epitope-targeted synthetic affinity agent with an antibody-recruiting moiety.

Epitope-targeted peptide immunostimulants have several advantages versus conventional antibiotic molecules and other synthetic immunostimulants. A main advantage is that they can be judiciously, rapidly (<1 month), and reliably developed against virtually any epitope on a bacterial surface. This would allow EPIs to be easily engineered as a therapeutic counter to emerging pathogens that are partially or completely resistant to available antibiotics. A second advantage is their relatively low cost and high thermal stabilities, which would enable them to be scaled up and transported around the world without minimal or no loss of efficacy. While small molecules also exhibit these properties, antibodies are notoriously unstable and have high production costs. Thus, EPIs present advantages versus antibodies, which are an emerging therapeutic option for treating pathogenic infections. The EPI technology also is advantageous compared to other synthetic immunostimulatory agents because of its epitope specificity, which makes EPIs targetable to virtually any specified bacterium. Other synthetic immunostimulants technologies target certain cell-receptors or cellular processes, which limits the scope of bacteria (or other cells) that can be targeted.

It is to be understood that the disclosed method and compositions are not limited to specific synthetic methods, specific analytical techniques, or to particular reagents unless otherwise specified, and, as such, can vary. It is also to be understood that the terminology used herein is for the purpose of describing particular embodiments only and is not intended to be limiting.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

A residue of a monomer unit or moiety refers to the portion of the monomer or moiety that is the resulting product of the monomer unit or moiety in a particular reaction scheme or subsequent formulation or chemical product, regardless of whether the portion of the monomer or moiety is actually obtained from the monomer unit or moiety. Thus, an amino acid residue in a peptide refers to one or more —CO—CHR—NH— moieties in the peptide, regardless of whether the residue is obtained by reacting the amino acid to obtain the peptide.

As used herein, the term "non-natural amino acid" refers to an organic compound that has a structure similar to a natural amino acid so that it mimics the structure and reactivity of a natural amino acid. The non-natural amino acid as defined herein generally increases or enhances the properties of a peptide (e.g., selectivity, stability) when the non-natural amino acid is either substituted for a natural amino acid or incorporated into a peptide.

As used herein, the term "peptide" refers to a class of compounds composed of amino acids chemically bound together. In general, the amino acids are chemically bound together via amide linkages (CONH); however, the amino acids can be bound together by other chemical bonds known in the art. For example, the amino acids can be bound by amine linkages. Peptide as used herein includes oligomers of amino acids and small and large peptides, including polypeptides.

As used herein, the term "activity" refers to a biological activity.

As used herein, the term "pharmacological activity" refers to the inherent physical properties of a compound or composition, such as the disclosed EPIs. These properties include but are not limited to half-life, solubility, and stability and other pharmacokinetic properties.

Epitope-Targeted Immunostimulants (EPIs)

Disclosed are epitope-targeted immunostimulants (EPIs) comprising a synthetic peptide ligand and an antibody-recruiting moiety, where the peptide ligand and the antibody-recruiting moiety are conjugated or coupled together. In some forms, the peptide ligand has affinity for an epitope on a target molecule comprised in a target. In some forms, the epitope is exposed on the surface of the target. In some forms, the antibody-recruiting moiety recruits antibodies to the target when the EPI is bound to the epitope on the target.

In some forms, the peptide ligand is cyclic.

In some forms, the peptide ligand comprises a 1,4-substituted-1,2,3-triazole residue (Tz4) or a 1,5-substituted-1,2,3-triazole residue (Tz5). In some forms, the peptide ligand comprises a 1,4-substituted-1,2,3-triazole residue (Tz4). In some forms, the peptide ligand comprises a 1,5-substituted-1,2,3-triazole residue (Tz5).

In some forms, the peptide ligand was identified by non-catalyzed in situ click chemistry screening of a combinatorial peptide library.

In some forms, the target is a microorganism. In some forms, the microorganism is an infectious microorganism. In some forms, the microorganism is a bacterium or a fungal cell. In some forms, the microorganism is a Gram-negative bacterium. In some forms, the microorganism is in the genus *Klebsiella*, *Salmonella*, *Escherichia*, *Staphylococcus*, *Legionella*, *Pseudomonas*, *Haemophilus*, *Helicobacter*, *Vibrio*, *Acinetobacter*, *Bordetella*, *Campylobacter*, *Citrobacter*, *Enterobacter*, *Serratia*, *Shigella*, *Yersinia*, or *Neisseria*. In some forms, the microorganism is in the species *Klebsiella* spp., *Salmonella* spp., *Escherichia coli*, *Staphylococcus* spp., *Legionella pneumophila*, *Pseudomonas aeruginosa*, *Haemophilus influenza*, *Helicobacter pylori*, *Vibrio cholerae*, *Acinetobacter* spp., *Bordetella pertussis*, *Campylobacter* spp., *Citrobacter* spp., *Enterobacter* spp., *Serratia marcescens*, *Shigella* spp., *Yersinia* spp., or *Neisseria* spp.

In some forms, the microorganism is *Klebsiella pneumoniae*. In some forms, the microorganism is *Staphylococcus aureus*. In some forms, the microorganism is in the family Enterobacteriaceae.

In some forms, the target is a virus. In some forms, the virus is an influenza virus or a coronavirus.

In some forms, the target molecule is MrkA protein. In some forms, the epitope has the amino acid sequence TEVKAAAADTYLKP (SEQ ID NO:2). In some forms, the peptide ligand comprises the amino acid sequence LLFFF (SEQ ID NO:5).

In some forms, the target molecule is *Staphylococcus aureus* peptidoglycan. In some forms, the target molecule is methicillin-resistant *Staphylococcus aureus* peptidoglycan. In some forms, the peptide ligand comprises the amino acid sequence kpdew (SEQ ID NO:23) or akkrp (SEQ ID NO:34).

In some forms, the antibody-recruiting moiety comprises an epitope recognized by an antibody that mediates recognition and phagocytosis of the target by an immune cell. In some forms, the epitope recognized by an antibody that mediates recognition and phagocytosis of the target by an immune cell is an immunogen endogenously recognized by a mammalian immune system. In some forms, the epitope recognized by an antibody that mediates recognition and phagocytosis of the target by an immune cell is an immunogen endogenously recognized by a human immune system.

In some forms, the epitope recognized by an antibody that mediates recognition and phagocytosis of the target by an immune cell is 2,4-dinitrophenyl (DNP), alpha-galactose, galactose(alpha1-3)galactose, beta-lactam, 1,3-diketone, avidin, fluorescein, fluorescein-DNP, or nitrophenol.

In some forms, the peptide ligand is comprised in a multi-ligand, wherein the multi-ligand further comprises a second ligand, wherein the second ligand has affinity for a second epitope on the target molecule, wherein the second epitope is exposed on the surface of the target, wherein the peptide ligand and the second ligand are covalently linked to each other, wherein the multi-ligand can simultaneous bind to the epitope and to the second epitope on the target molecule.

Also disclosed are compositions comprising any of the disclosed EPIs.

Also described herein are pharmaceutically acceptable nontoxic ester, amide, and salt derivatives of EPIs. The disclosed EPIs also encompass pharmaceutically acceptable esters, amides, and salts of such EPIs. EPIs also encompasses pharmaceutically acceptable salts. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds EPIs to base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds—as illustrated in the examples below—and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine.

Every EPI within the above definition (or as otherwise disclosed herein) is intended to be and should be considered to be specifically disclosed herein. Further, every subgroup that can be identified within the above definition is intended to be and should be considered to be specifically disclosed herein. As a result, it is specifically contemplated that any EPI, or subgroup of EPIs can be either specifically included for or excluded from use or included in or excluded from a list of EPIs.

Every ligand within the above definition (or as otherwise disclosed herein) is intended to be and should be considered to be specifically disclosed herein. Further, every subgroup that can be identified within the above definition is intended to be and should be considered to be specifically disclosed herein. As a result, it is specifically contemplated that any ligand, or subgroup of ligands can be either specifically included for or excluded from use or included in or excluded from a list of ligands.

Antibody-recruiting molecules (ARMs) generally re molecules that bind to antibodies. Preferred ARMs can bind to antibodies that (1) are present in the body of a subject and (2) when bound to a target will attract an immune response or effect on the target. Useful ARMs include dinitrophenol (DNP), alpha-galactose, galactose(alpha1-3)galactose, beta-lactam, 1,3-diketone, avidin, fluorescein, fluorescein-DNP, and nitrophenol (McEnaney et al., ACS Chem Biol 7(7): 1139-1151 (2012)).

Every ARM within the above definition (or as otherwise disclosed herein) is intended to be and should be considered to be specifically disclosed herein. Further, every subgroup that can be identified within the above definition is intended to be and should be considered to be specifically disclosed herein. As a result, it is specifically contemplated that any ARM, or subgroup of ARMs can be either specifically included for or excluded from use or included in or excluded from a list of ARMs.

Methods of Making/Screening Target Ligands and Capture Agents

Provided herein in some forms are methods of screening target-binding moieties (e.g., ligands) and/or making capture agents that comprise these target-binding moieties.

Methods for screening target-binding moieties and/or making capture agents that comprise these target-binding moieties can also be found in International Publication Nos. WO 2012/106671, WO 2013/033561, WO 2013/009869 and WO 2014/074907, each of which is incorporated by reference, herein, in their entireties.

If the protein target has a known and well-defined tertiary (folded) structure, then key aspects of this targeting method involve strategies for identifying ligands that bind to selected epitopes of the protein. If the protein does not have a well-defined tertiary structure, the disclosure describes strategies designed to produce specific, high affinity ligand. The selection of the target and an epitope on that target can benefit from the multi-omic approach described herein.

The initial goal for developing a set of PCC binders against a protein target is to identify one or more PCCs that bind to an epitope on the protein target. In the epitope targeted PCC method, this can be accomplished by screening peptide libraries against synthetic epitopes (SynEps, also referred to as "Epitopes" herein, e.g., Epitope1, Epitope2, and Epitope3 and first epitope, second epitope, and third epitope). A SynEp is a polypeptide that has the sequence of the naturally occurring target epitope, except that one position contains an artificial amino acid that presents an azide or acetylene chemical group, called a click handle. The SynEp is further modified to contain an assay handle, such as a biotin group, at the N- or C-terminus. The screening procedure can be done using any procedure disclosed herein or known in the art. By screening, one identifies at least one unique peptide binder to each of at least two epitopes on the target. Those peptide binders are validated via carrying out binding assays against the full protein target as well as against the SynEps. For those binding assays, the SynEps are prepared with the naturally occurring residue in place of the click handle.

Peptide library screening can be performed with one or more different epitopes. When two or more different epitopes are used, some or all of the different epitopes can be used sequentially in the screening (referred to as sequential screening) (screening, for example, only the hit peptides from a prior screen in a subsequence screen), in combination (referred to as multi-ligand screening) (screening, for example, using two or more different epitopes in the same screen), or a combination of both sequential and combination screening. In some forms, the epitopes used can be two epitopes where the epitope is selected from the group consisting of amino acid sequences comprising FFGKVTDVSCTVSV (SynEp 1; SEQ ID NO:1), TEVKAAAADTYLKP (SynEp 2; SEQ ID NO:2), ATSKQQGYLANTEA (SynEp 3; SEQ ID NO:3), STQPKAKGDASAVA (SynEp 4; SEQ ID NO:4). In some forms, the epitopes used can be two or more epitopes where each epitope is selected from the group consisting of amino acid sequences comprising FFGKVTDVSCTVSV (SynEp 1; SEQ ID NO:1), TEVKAAAADTYLKP (SynEp 2; SEQ ID NO:2), ATSKQQGYLANTEA (SynEp 3; SEQ ID NO:3), STQPKAKGDASAVA (SynEp 4; SEQ ID NO:4).

In some forms, the epitopes used can be two epitopes where the epitope is selected from the group consisting of amino acid sequences comprising MRSA peptidoglycan SynEp 1a, MRSA peptidoglycan SynEp 1b, and MRSA peptidoglycan SynEp 1c. In some forms, the epitopes used can be two or more epitopes where each epitope is selected from the group consisting of amino acid sequences comprising MRSA peptidoglycan SynEp 1a, MRSA peptidoglycan SynEp 1b, and MRSA peptidoglycan SynEp 1c.

In some forms, two separately-identified ligands that bind to two different regions of the same protein (the target) are chemically linked together to form a biligand. By optimizing a linker of the two ligands, the biligand formed by the ligands and linker can exhibit a binding affinity that is far superior to either of the individual ligands. This enhanced binding effect is called binding cooperativity. For an ideal cooperative binder, the thermodynamic binding energies of the individual ligands to the target will sum to yield the binding energy of the linked biligand. This means that the binding affinity constant ($K_D$) of the linked biligand will be the product of the binding affinity of the individual ligands (i.e. $K_D = K_{D1} \times K_{D2}$, where the subscripts 1 and 2 refer to the two ligands). In practice, full cooperative binding is rarely, if ever, achieved. Thus, a comparison of the properties of a linked biligand against those of a fully cooperative binder provides a measurement of how optimally the two ligands were linked.

Once the epitope targeted PCCs are identified, there are several methods for selecting a linker. In some forms, if the folded structure of the protein is known, and if the PCCs bind to that folded structure, then one can use that information, plus knowledge of which PCCs bind to which epitopes, to estimate an optimal linker length. For example, one PCC can bind to the N-side of one epitope and a second PCC can bind to the C-side of a second epitope. Analysis of this binding arrangement, together with the structure of the protein from, for example, the Protein Database, permits an estimate of the length of an optimized linker. Such an estimate can narrow down the choice of candidate linkers to a very small number. One example might be to use such a length estimate to select one or two length-matched polyethylene glycol oligomers for testing. The best linker is the one that brings the biligand affinity closest to that a fully cooperative binder.

Multi-Omic Analyses to Select Target Protein on *K. pneumoniae*

The ability to target specified epitopes on a bacterium enables EPIs to target virtually any bacterium or other pathogen. A challenge, however, in developing an EPI against a bacterium or other pathogen is the selection of a target, among the myriad proteins and epitopes encoded by the bacterium or other pathogen. This problem was approached by integrating multi-omic and bioinformatic analysis to select optimal protein and epitope targets on the bacterium or other pathogen. In the examples here, that target was a protein and epitope *K. pneumoniae* and a protein and epitope of methicillin-resistant *Staphylococcus aureus* (MRSA).

Favorable aspects of target proteins are localization and high expression levels in the outer membrane or extracellular space, which should promote high extents of EPI-driven and opsonization. However, importantly, expression levels may vary with environment and growth phase, which must also be factored into choosing a target protein. Analysis of multi-omic data of *K. pneumoniae* efficiently clarified the choice for a target protein. Inspection of all available proteomic datasets for *K. pneumoniae* yielded 85 proteins located either in the outer membrane or extracellular space (47-49). Separately, complementary transcriptomic datasets (46) then identified proteins that were highly expressed during three key life stages of *K. pneumoniae*: exponential phase, stationary phase, and biofilms (including detached cells). The top 10% of highly-expressed genes (515 protein candidates) across these conditions were then cross-referenced with proteomic data to identify highly-expressed proteins localized either to the outer membrane or extracellularly (13 candidates). A literature search then narrowed the selection of a target proteins, specifically by prioritization of virulence- and pathogenicity-related genes and cytoplasmic or extracellular orientation in the outer membrane. Ultimately, the fimbrial subunit MrkA was chosen because of its definitively extracellular location in fimbrial rods, which are large (0.5-2 µM) structures (54) associated with *K. pneumoniae* virulence (50), and extremely high abundance, as bacteria express hundreds of fimbriae each with an estimated 1000s of MrkA proteins (56). Moreover, MrkA is expressed in a majority of analyzed *K. pneumoniae* strains (51-53).

The selection of target epitopes on MrkA poses challenges that we approached by using powerful bioinformatic tools. Ideal epitope targets would be surface exposed to ensure accessibility to EPIs, as well as have low sequence homology versus epitopes in the human proteome, to reduce off-target binding in vivo. Guidance in selecting surface exposed epitopes could be provided by a protein structure, though structures for MrkA do not exist. As a surrogate for structure, we employed advanced bioinformatics tools (NetSurfP2.0, Bepipred 2.0, and BlastP2.0) to survey MrkA for epitopes with high surface exposures and low homology with the human proteome. B-cell antigenicity was also considered in epitope selection; the ability for EPIs to target highly antigenic epitopes would validate the technology with respect to antibodies, while targeting non-antigenic epitopes demonstrates that EPIs could elicit immune responses where the native immune system cannot.

Figure 2A:
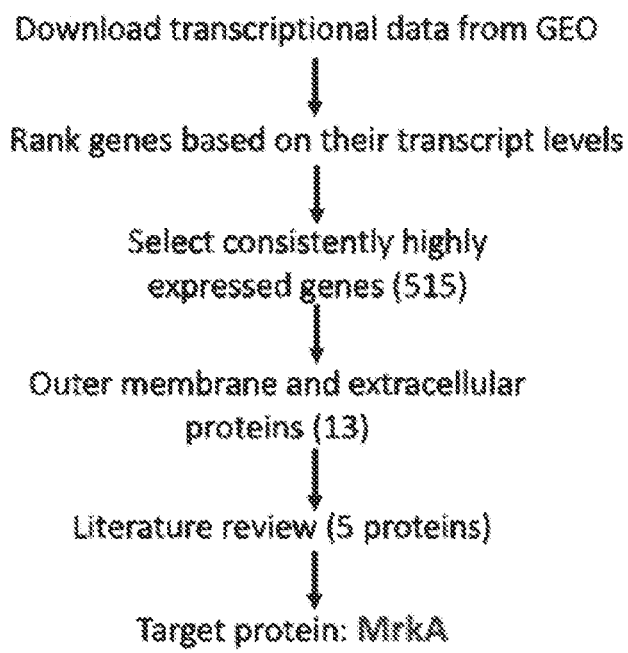
FIGS. 2A and 2B illustrate a strategy for selecting protein and epitope targets on *K. pneumoniae* bacteria for EPIs (AR-PCCs).
Figure 2B:
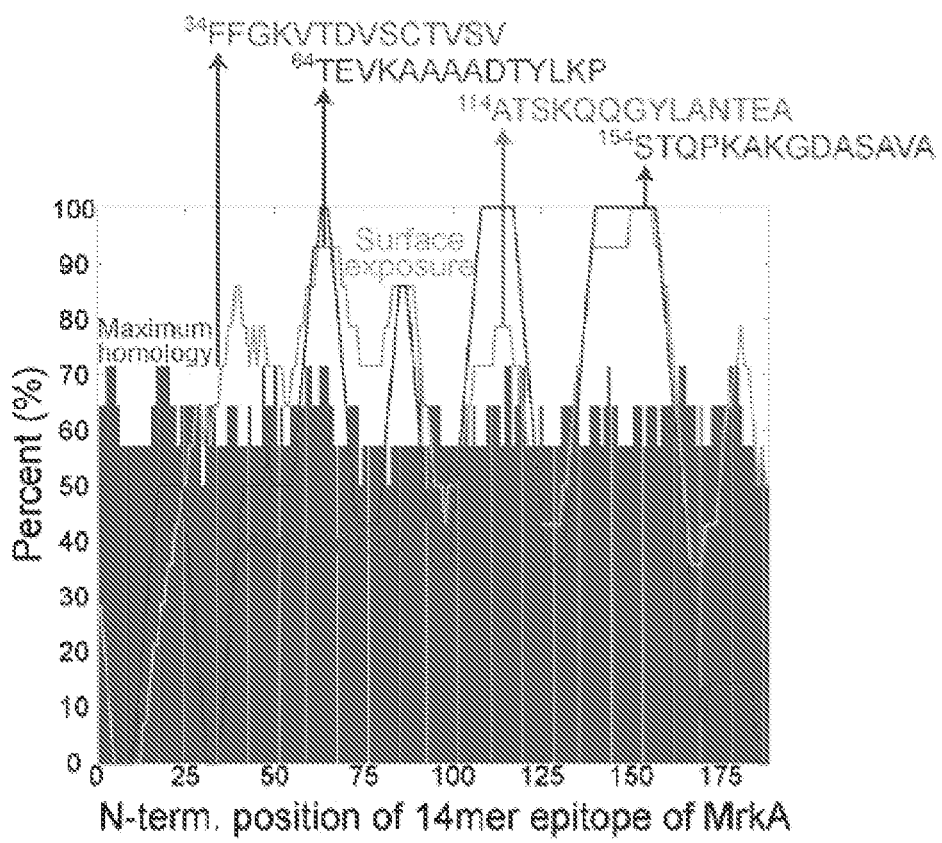

The surface exposure, antigenicity, and homology of 14-residue epitopes on the MrkA sequence were predicted and superimposed in FIG. 2B to facilitate epitope selection. Surface-exposure and antigenicity were calculated by predicting these properties across the MrkA primary sequence and then averaging over each 14-residue epitope, while homology was predicted by comparing each 14-residue epitope to the human proteome by using BlastP2.0. The plot in FIG. 2B reveals numerous epitopes with high (>60%) surface exposure (FIG. 2B, green line) and comparably low (~50-55%) homology to human proteins (FIG. 2B, blue bars), which would be ideal targets for EPIs. Moreover, these epitopes range in predicted antigenicity from 0 to 100%. Three highly (100%) antigenic epitopes (N-termini at residue 64, 114 and 154, FIG. 2B, black arrow) and one non-antigenic epitope (N-terminus at residue 34, FIG. 2B, black arrow) with high surface exposure (>60%) and relatively low (57-71%) maximum homology were selected as targets for EPIs. The sequences of these target epitopes are listed in the inset of FIG. 2B.

Epitope-Targeted Ligands Against the MrkA Protein

Figure 3A:
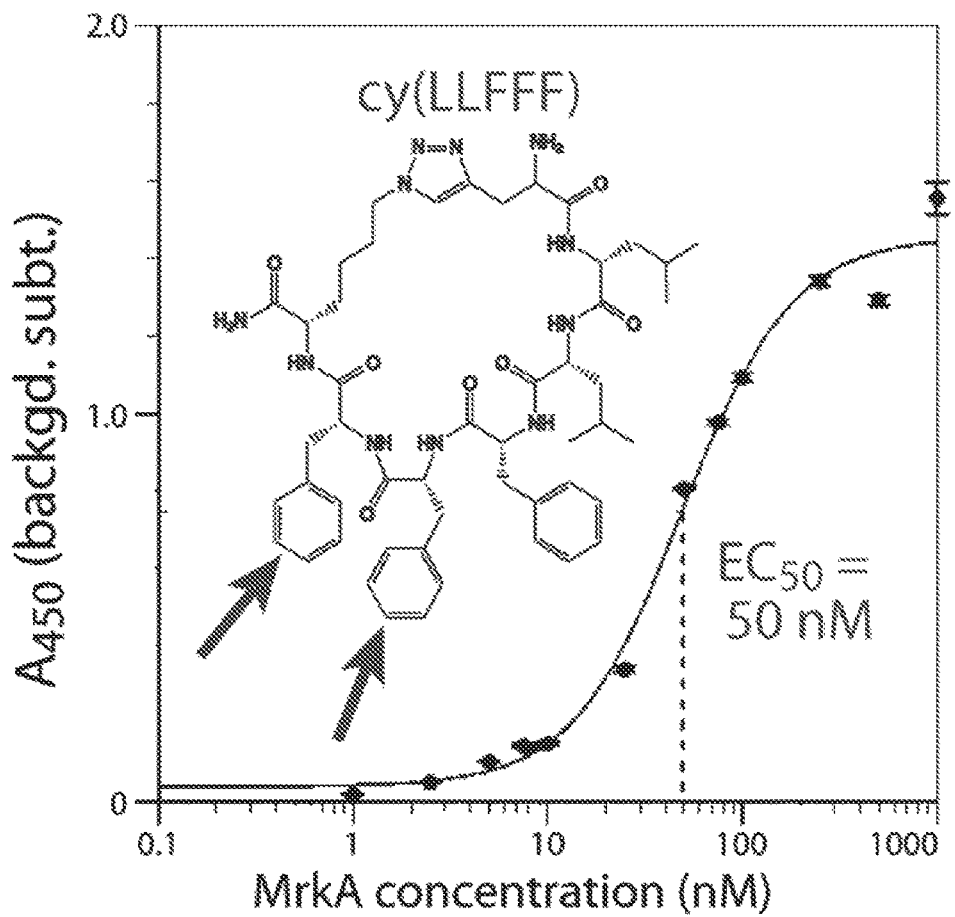
FIGS. 3A and 3B are graphs showing the binding of the top-performing PCC ligand cy(LLFFF) (SEQ ID NO:5) to protein and epitope targets. Sandwich enzyme-linked immunoassays (ELISA) reveal that the lead EFI (AR-PCC) ligand cy(LLFFF) (SEQ ID NO: 5) binds to full-length MrkA protein with an $EC_{50}$ value of 50 nM (FIG. 3A) and selectively binds synthetic epitope 2 versus other targeted epitopes (FIG. 3B). The sequences depicted are FFGKVTDVSCTVSV (SynEp 1; SEQ ID NO:1), TEVKAAAADTYLKP (SynEp 2; SEQ ID NO:2), ATSKQQGYLANTEA (SynEp 3; SEQ ID NO:3), STQPKAKGDASAVA (SynEp 4; SEQ ID NO:4), cy(LLFFF) (SEQ ID NO: 5), and cy(HYEWL) (SEQ ID NO:6). The cy(HYEWL) (SEQ ID NO:6) ligand is a negative control. All measurements were performed in triplicate, and signals were background-corrected by subtracting the absorbance from otherwise identically prepared wells, except with biotin-peg6 conjugated. Error bars reflect standard deviations. Each PCC and SynEp used here had an N-terminal Biotin-peg5 group.
Figure 3B:
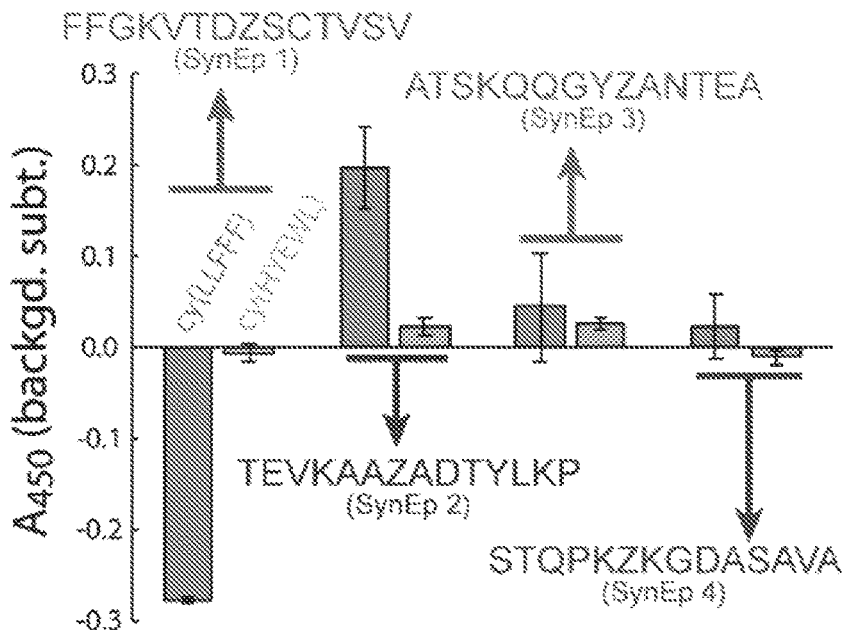

EPI ligands against the four selected target epitopes were identified from combinatorial libraries by using a state-of-the-art PCC screening technique (42-44, 92). Briefly, this process exploits a non-catalyzed click chemistry to assay a one-bead one-compound combinatorial library for high-affinity binding to a particular epitope. The screens used here involve incubating a combinatorial library of alkyne-presenting cyclic heptapeptides with a synthetic version of the target epitope (a SynEp), in which one natural residue is strategically substituted with a non-natural azidolysine. Library members that bind SynEps in just the right orientation undergo a 1,3-Huisgen dipolar addition reaction that covalently links the SynEp to the bead, which can be detected colorimetrically by employing the biotin handle for enzymatic amplification with streptavidin-alkaline phosphatase. The screen yielded 26 hits that were scaled up and tested for binding to the full-length recombinant MrkA protein by using Enzyme-linked immunoassays, in which the PCC was immobilized. The top-performing ligand had the sequence cy(LLFFF) (SEQ ID NO:5), where "cy" represents cyclization and letters in single-letter amino acid code, and exhibited estimated $EC_{50}$ value of 230 nM, as determined by ELISA (FIG. 3A). Several other ligands with lower affinities (likely ~1 µM) to MrkA were identified, with sequences cy(TTFFF) (SEQ ID NO:35), cy(YRHLG) (SEQ ID NO:56) and cy(GVHRL) (SEQ ID NO:57). Based upon chemical analysis, these ligands likely bind distinct epitopes on MrkA than cy(LLFFF) (SEQ ID NO:5). The lead ligand cy(LLFFF) (SEQ ID NO:5) was also observed to preferably bind synthetic epitope 2, which has sequence (TEV-KAAZADTYLKP, where Z refers to azidolysine; SEQ ID NO:39) versus the other three synthetic epitopes that were screened by using the PCC method (FIG. 3B). This indicates that cy(LLFFF) (SEQ ID NO:5) binds target epitope 2, sequence (TEVKAAAADTYLKP; SEQ ID NO:2) on MrkA.

Selective Binding of EPIs to *Klebsiella pneumoniae* Cells

Figure 5A:
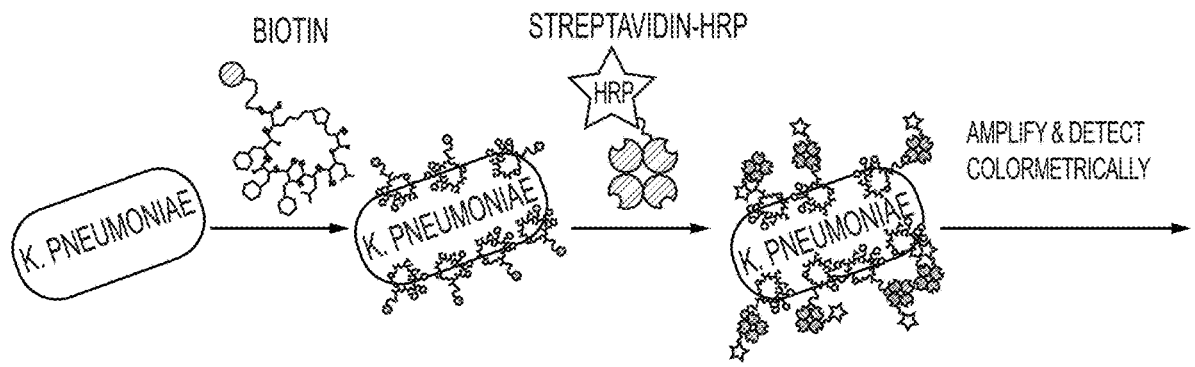
FIGS. 5A, 5B, and 5C show binding specificity of cy(LLFFF) (SEQ ID NO:5) towards MrkA-expressing drug resistant *K. pneumoniae* cells.
Figure 5B:
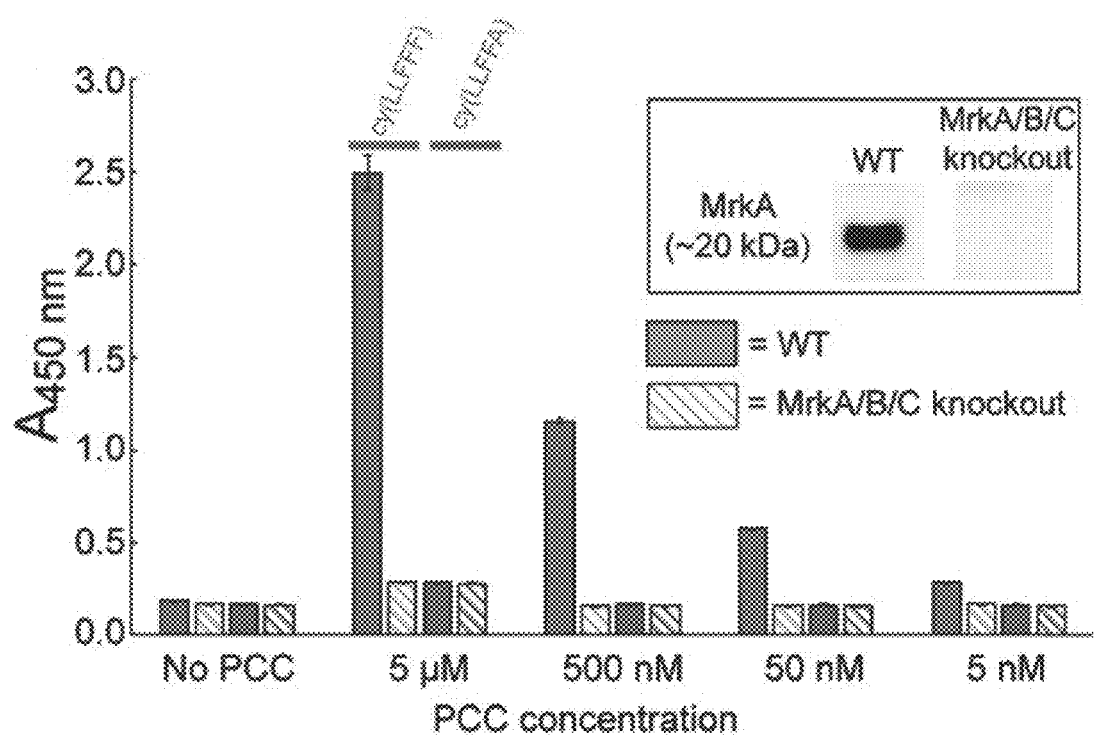
Figure 5C:
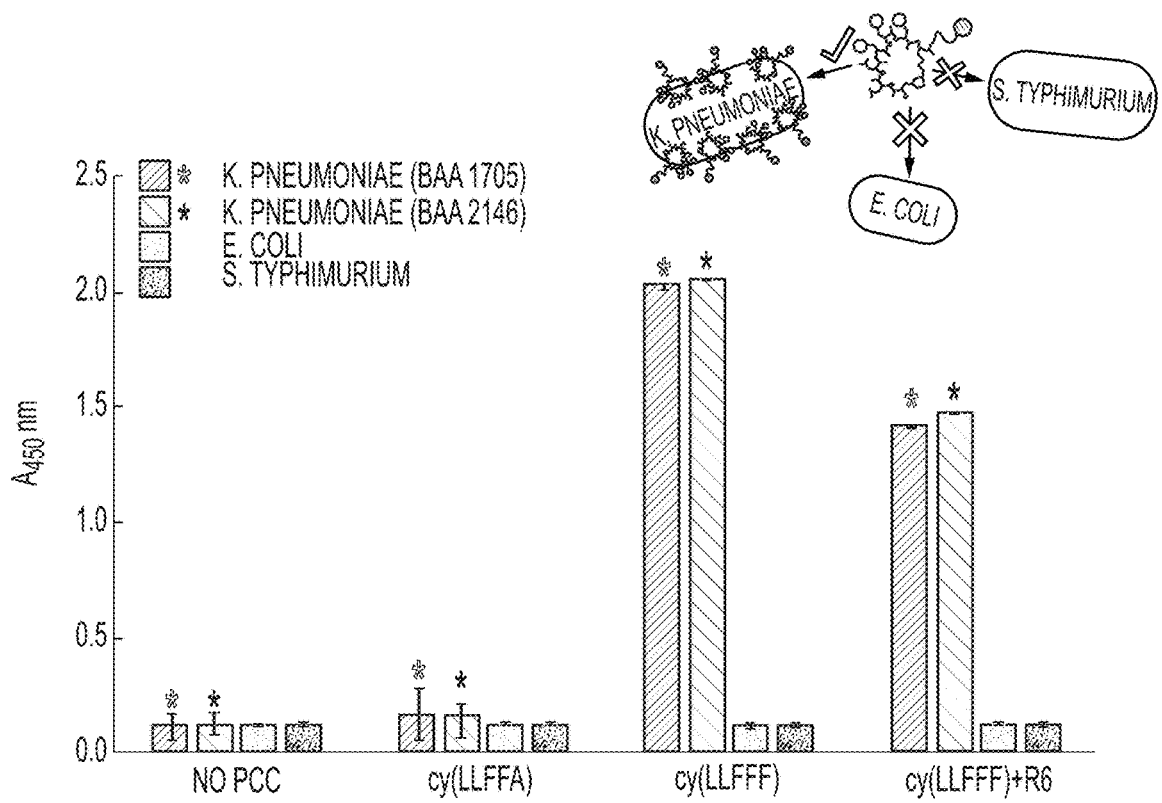

While ELISAs test for EPI ligand binding against monomeric MrkA in solution, MrkA assembles as an oligomer in the fimbriae of MrkA. Thus, the binding of cy(LLFFF) ligands to MrkA-producing *K. pneumoniae* cells was tested. In this assay, *K. pneumoniae* cells were exposed to biotinylated EPI ligands, then streptavidin-horseradish peroxidase, and subjected to development conditions to produce a colorimetric signal. Greater absorption correlates with more binding by biotinylated EPI ligands. FIG. 5C shows high absorbance from two strains of *K. pneumoniae* cells exposed to biotinylated cy(LLFFF) (SEQ ID NO:5) EPI ligands, while the same strains exposed to biotinylated cy(HNGPT) (SEQ ID NO:18) ligands had comparably lower signal. This establishes high levels of binding of cy(LLFFF) (SEQ ID NO:5) to MrkA-expressing *K. pneumoniae* cells. Furthermore, we also observed small absorbances from *E. coli* and S. typhimurius samples exposed to the same biotinylated cy(LLFFF) (SEQ ID NO:5) ligands, demonstrating that cy(LLFFF) (SEQ ID NO:5) binds *K. pneumoniae* cells selectively. Together with the ELISA data, this supports the high protein and epitope specificities of ligands developed by the protein-catalyzed capture agent method (41, 42).

EPI-Driven Opsonization by Anti-Dinitrophenyl Antibodies

The results above also underscore an ability of biotinylated cy(LLFFF) (SEQ ID NO:5) to recruit anti-biotin to cellular surfaces. While this is a crude demonstration of EPI-driven opsonization, biotin recruitment of streptavidin-horseradish peroxidase would not promote opsophagocytic killing (OPK) of *K. pneumoniae* cells in vivo. By comparison, EPI ligands conjugated with immunogens that are endogenously recognized by human immune systems would induce effective immune responses against antibiotic-resistant bacteria without the need to introduce antibodies exogenously. Thus, an immunogenic 2,4-dinitrophenyl (DNP) moiety was incorporated into EPI ligands on the sidechain amine of a lysine residue appended to a flexible polyethylene glycol linker. The DNP moiety was selected as an immunogen because it is an agonist for ~1% of endogenous antibodies in humans (67), allowing EPIs with DNP moieties to elicit native immune responses. We hypothesized that DNP-conjugated EPIs could recruit anti-DNP antibodies to the surfaces of *K. pneumoniae* cells. To test this, cells were incubated with DNP-conjugated EPIs and then fluorescently labeled anti-DNP antibody (Alexafluor488), and subsequently quantified the fluorescence of cells by using flow cytometry.

Cytometry results revealed an ability for DNP-conjugated EPIs to recruit anti-DNP antibodies to *K. pneumoniae* cell surfaces. The cytometry data showed little fluorescence (predominantly <$10^1$ intensity) of *K. pneumoniae* cells that were not stained by either EPI or antibody. Slightly greater fluorescence was observed for cells stained with secondary antibody either without or with prior incubation with cy(HNGPT) (SEQ ID NO:18) at 50 μM. The fluorescence of all these samples, however, was substantially less intense than for cells exposed to cy(LLFFF) (SEQ ID NO:5) and then incubated with anti-DNP. This establishes that DNP-conjugated EPI ligands promote the opsonization of *K. pneumoniae* cells with anti-DNP antibodies. Paired with the binding of biotinylated cy(LLFFF) (SEQ ID NO:5) to *K. pneumoniae* cells, these results moreover support the versatility of EPIs to recruit distinct and specified biomolecules to the surfaces of bacterial cells, which can be therapeutically powerful by, for instance, recruiting complement proteins.

EPI-Driven Opsonophagocytic Killing of Antibiotic-Resistant *K. pneumoniae*

It also tested whether DNP-conjugated EPIs could promote the opsonophagocytic killing (OPK) of *K. pneumoniae* by macrophages. This was tested by using an OPK assay. Briefly, *K. pneumoniae* cells were treated with EPI and then anti-DNP antibody before being exposed to macrophages for either 6 or 24 hours. During this incubation period, macrophages that recognize *K. pneumoniae* cells will phagocytose them, and phagocytosed bacteria will remain viable for up to 6 hours, but within 24 hours are rendered inviable by OPK. Thus, macrophages were isolated after 6 and 24 hours of incubation with *K. pneumoniae*, lysed them, and plated and grew the lysate, which yielded bacterial colonies that reflect the phagocytosis (at 6 hrs) or OPK (at 24 hrs) of bacteria.

Figure 14:
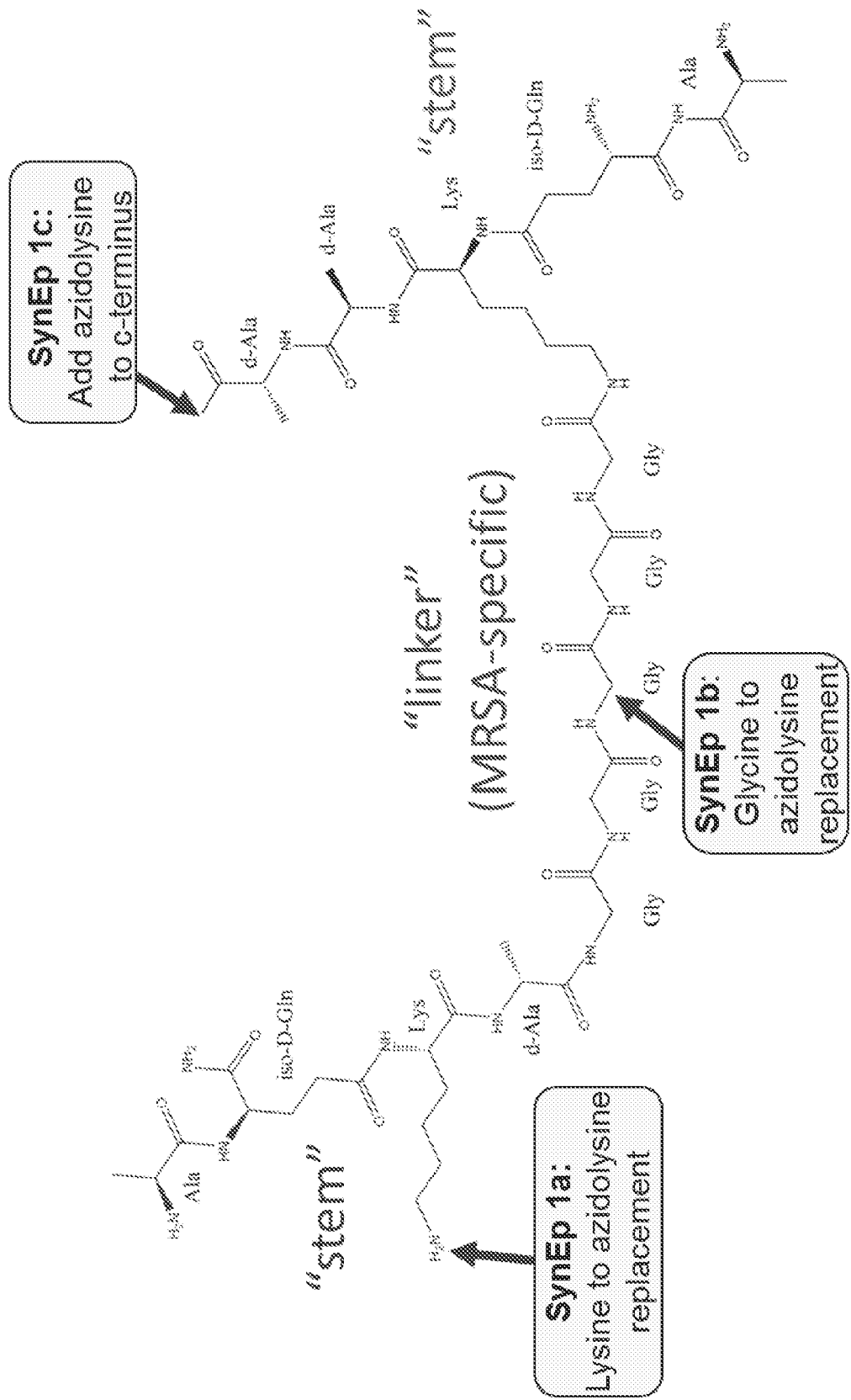
FIG. 14 shows the design of synthetic epitopes (SynEps) for protein catalyzed capture agent (PCC) screen against peptidoglycan of methicillin-resistant *Staphylococcus Aureus* (MRSA) bacteria. The molecular structure of peptidoglycan, shown here, contains two "stem" regions with a MRSA-specific pentaglycine linker. Three synthetic versions of this molecule were prepared for PCC screens, with an azidolysine residue either replacing the lysine residue of the stem (SynEp 1a), replacing the middle glycine residue of the linker (SynEp 1b), or appended to the C-terminus of the stem (SynEp 1c). These three synthetic epitopes were used to screen a combinatorial one-bead one-compound library of cyclic heptapeptides using the PCC method.
Figure 15:
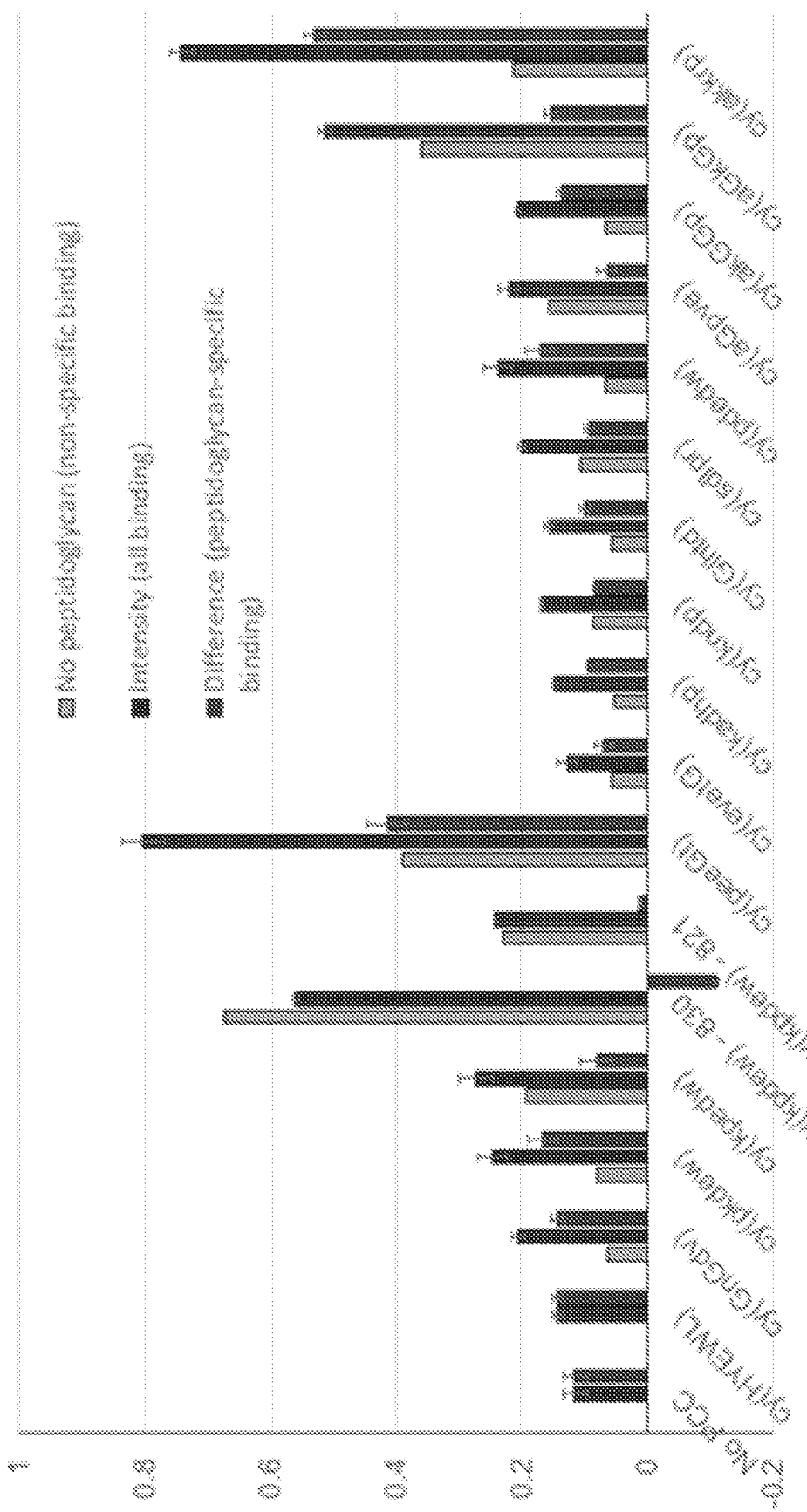
FIG. 15 is a graph showing PCC-driven recruitment of streptavidin-horseradish peroxidase (SAv-HRP) conjugate to peptidoglycan isolated from MRSA cells via enzyme-linked Immunosorbent Assays (ELISAs). All tests were conducted by coating the antigen (MRSA peptidoglycan) onto the wells of 96-well plates and then exposing the wells solutions containing biotinylated PCCs, then SAv-HRP, then HRP substrate followed by detection via absorbance at 450 nm. Absorbance from peptidoglycan-coated wells (blue bars) was subtracted from non-coated wells (orange bars) to assess the peptidoglycan-specific binding (red bars), which revealed SAv-HRP recruitment to MRSA peptidoglycan by several biotinylated PCCs. All measurements were conducted in triplicate and error bars reflect standard deviations. The PCC sequences are, from left to right, SEQ ID NOs: 6, 20-23, and 23-34.

The biological assays described above clearly showed that EPIs promoted OPK of *K. pneumoniae* cells. Here, a *K. pneumoniae* strain (BAA 1705) was used that exhibits high antibiotic resistance, including to last-line carbapenem antibiotics. Similar cell counts of ~35,000 were observed from controls prepared from macrophages harvested at 6 hrs after incubation with *K. pneumoniae* cells exposed to no EPI or antibody, only anti-DNP, or DNP-conjugated EPIs with cy(LLFFF) (SEQ ID NO:5) or cy(HNGPT) (SEQ ID NO:18; a non-MrkA-binding dummy ligand) (FIG. 14). Moreover, an almost identical CFU count was observed for samples prepared from macrophages that were incubated with *K. pneumoniae* cells treated with DNP-conjugated cy(HNGPT) (SEQ ID NO:18) and anti-DNP antibody, indicating the DNP-conjugated cy(HNGPT) (SEQ ID NO:18) dummy ligand did not promote any phagocytosis, as expected from its low binding to *K. pneumoniae* cells (FIG. 14). By comparison, more than 80,000 CFU were observed samples in which *K. pneumoniae* was treated with a DNP-conjugated version of the lead EPI ligand cy(LLFFF) (SEQ ID NO:5), which was comparable to samples prepared by opsonizing *K. pneumoniae* cells with anti-KP antiserum and anti-MrkA antibody (FIG. 14). This demonstrates that EPIs can promote phagocytosis of antibiotic-resistant bacteria. Further, all samples prepared from macrophages isolated at 24 hours of incubation showed little to no CFU, indicating near complete OPK. This demonstrates that EPIs can also drive OPK against a highly resistant bacterium.

Disclosed are methods of stimulating an immune reaction to a microorganism or other pathogen in a subject, the method comprising administering an EPI to the subject, wherein the microorganism or other pathogen in the subject is the target of the EPI of the composition.

In some forms, the microorganism in the subject is resistant to one or more antibiotics. In some forms, the microorganism in the subject is resistant to one or more classes of antibiotics. In some forms, the microorganism in the subject is multidrug-resistant. In some forms, the microorganism is a bacterium or a fungal cell. In some forms, the microorganism is a Gram-negative bacterium. In some forms, the microorganism is in the genus *Klebsiella, Salmonella, Escherichia, Staphylococcus, Legionella, Pseudomonas, Haemophilus, Helicobacter, Vibrio, Acinetobacter, Bordetella, Campylobacter, Citrobacter, Enterobacter, Serratia, Shigella, Yersinia,* or *Neisseria*. In some forms, the microorganism is in the species *Klebsiella* spp., *Salmonella* spp., *Escherichia coli, Staphylococcus* spp., *Legionella pneumophila, Pseudomonas aeruginosa, Haemophilus influenza, Helicobacter pylori, Vibrio cholerae, Acinetobacter* spp., *Bordetella pertussis, Campylobacter* spp., *Citrobacter* spp., *Enterobacter* spp., *Serratia marcescens, Shigella* spp., *Yersinia* spp., or *Neisseria* spp.

In some forms, the microorganism is *Klebsiella pneumoniae*. In some forms, the microorganism is *Staphylococcus aureus*. In some forms, the microorganism is in the family Enterobacteriaceae.

Also disclosed are methods of identifying the peptide ligand, the method comprising:
  (a) selecting a protein that is highly expressed in a target microorganism and that at least a part of is exposed on the surface of the microorganism, wherein the selected protein is the target molecule;
  (b) selecting an epitope by identifying amino acid sequences of the selected protein that are predicted both to be surface-exposed and to have a low homology to the human proteome relative to other amino acid sequences of the selected protein and selecting one of the identified amino acid sequences as the epitope;
  (c) contacting a polypeptide fragment with a plurality of candidate peptides, wherein the polypeptide fragment comprises the epitope, wherein the epitope is modified or substituted with (i) a group comprising an azido or alkynyl group and (ii) a label, wherein the candidate peptides all comprise an alkynyl group if the epitope has an azido group or an azido group if the epitope has an alkynyl group; and (d) incubating the polypeptide fragment and the candidate peptides to allow formation of a triazole linkage between the polypeptide fragment and one of the candidate peptides, wherein a candidate peptide that forms a triazole linkage with the polypeptide fragment is identified as the peptide ligand.

In some forms, the group comprising an azido or alkynyl group is an artificial amino acid. In some forms, the artificial amino acid is propargylglycine (Pra). In some forms, the epitope comprises a phosphorylated amino acid, wherein the group comprising an azido or alkynyl group is a metalorganic molecule that selectively binds to the phospho group on the phosphorylated amino acid. In some forms, the metalorganic molecule comprises the label. In some forms, the label is biotin. In some forms, the metalorganic molecule comprises an azido group.

In some forms, the method further comprises: selecting a candidate peptide linked to the polypeptide fragment via a triazole linkage as the peptide ligand; and sequencing the peptide ligand. In some forms, the candidate peptide is selected by selecting labeled candidate peptides. In some forms, the method further comprises testing the peptide ligand for binding to the target molecule.

The term "hit" refers to a test compound that shows desired properties in an assay. The term "test compound" refers to a chemical to be tested by one or more screening method(s) as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist." One that decreases, or prevents, a known activity is an "antagonist."

The term "inhibit" means to reduce or decrease in activity or expression. This can be a complete inhibition of activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "monitoring" as used herein refers to any method in the art by which an activity can be measured.

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the disclosed compounds.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

A cell can be in vitro. Alternatively, a cell can be in vivo and can be found in a subject. A "cell" can be a cell from any organism including, but not limited to, a bacterium.

In one aspect, the compounds described herein can be administered to a subject comprising a human or an animal including, but not limited to, a mouse, dog, cat, horse, bovine or ovine and the like, that is in need of alleviation or amelioration from a recognized medical condition.

By the term "effective amount" of a compound as provided herein is meant a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compounds or compositions according to the methods described herein can be determined by evaluating the particular aspects of the medical history, signs, symptoms, and objective laboratory tests that are known to be useful in evaluating the status of a subject in need EPIs for the treatment of pathogen infection or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

Any of the EPIs can be used therapeutically in combination with a pharmaceutically acceptable carrier. The compounds described herein can be conveniently formulated into pharmaceutical compositions composed of one or more of the compounds in association with a pharmaceutically acceptable carrier. See, e.g., *Remington's Pharmaceutical Sciences*, latest edition, by E. W. Martin Mack Pub. Co., Easton, PA, which discloses typical carriers and conventional methods of preparing pharmaceutical compositions that can be used in conjunction with the preparation of formulations of the compounds described herein and which is incorporated by reference herein. These most typically would be standard carriers for administration of compositions to humans. In one aspect, humans and non-humans, including solutions such as sterile water, saline, and buffered solutions at physiological pH. Other compounds will be administered according to standard procedures used by those skilled in the art.

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The compounds and pharmaceutical compositions described herein can be administered to the subject in a number of ways depending on whether local or systemic treatment is desired, and on the area to be treated. Thus, for example, a compound or pharmaceutical composition described herein can be administered as an ophthalmic solution and/or ointment to the surface of the eye. Moreover, a compound or pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. Parenteral administration can also involve use of a slow, sustained, or controlled release system such that a constant dosage is maintained.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

The disclosed compositions and methods can be further understood through the following numbered paragraphs.

1. An epitope-targeted immunostimulant (EPI) comprising a synthetic peptide ligand and an antibody-recruiting moiety, wherein the peptide ligand and the antibody-recruiting moiety are conjugated or coupled together, wherein the peptide ligand has affinity for an epitope on a target molecule comprised in a target, wherein the epitope is exposed on the surface of the target, wherein the antibody-recruiting moiety recruits antibodies to the target when the EPI is bound to the epitope on the target.
2. The EPI of paragraph 1, wherein the peptide ligand is cyclic.
3. The EPI of paragraph 1 or 2, wherein the peptide ligand comprises a 1,4-substituted-1,2,3-triazole residue (Tz4) or a 1,5-substituted-1,2,3-triazole residue (Tz5).
4. The EPI of paragraph 3, wherein the peptide ligand comprises a 1,4-substituted-1,2,3-triazole residue (Tz4).
5. The EPI of paragraph 3, wherein the peptide ligand comprises a 1,5-substituted-1,2,3-triazole residue (Tz5).
6. The EPI of any one of paragraphs 1-5, wherein the peptide ligand was identified by non-catalyzed in situ click chemistry screening of a combinatorial peptide library.
7. The EPI of any one of paragraphs 1-6, wherein the target is a microorganism.
8. The EPI of paragraph 7, wherein the microorganism is an infectious microorganism.
9. The EPI of paragraph 7 or 8, wherein the microorganism is a bacterium or a fungal cell.
10. The EPI of any one of paragraphs 7-9, wherein the microorganism is a Gram-negative bacterium.
11. The EPI of any one of paragraphs 7-10, wherein the microorganism is in the genus *Klebsiella, Salmonella, Escherichia, Staphylococcus, Legionella, Pseudomonas, Haemophilus, Helicobacter, Vibrio, Acinetobacter, Bordetella, Campylobacter, Citrobacter, Enterobacter, Serratia, Shigella, Yersinia*, or *Neisseria*.
12. The EPI of any one of paragraphs 7-11, wherein the microorganism is in the species *Klebsiella* spp., *Salmonella* spp., *Escherichia coli, Staphylococcus* spp., *Legionella pneumophila, Pseudomonas aeruginosa, Haemophilus influenza, Helicobacter pylori, Vibrio cholerae, Acinetobacter* spp., *Bordetella pertussis, Campylobacter* spp., *Citrobacter* spp., *Enterobacter* spp., *Serratia marcescens, Shigella* spp., *Yersinia* spp., or *Neisseria* spp.
13. The EPI of any one of paragraphs 7-12, wherein the microorganism is *Klebsiella pneumoniae*.
14. The EPI of any one of paragraphs 7-12, wherein the microorganism is *Staphylococcus aureus*.
15. The EPI of any one of paragraphs 7-11, wherein the microorganism is in the family Enterobacteriaceae.
16. The EPI of any one of paragraphs 1-13, wherein the target molecule is MrkA protein.
17. The EPI of paragraph 16, wherein the epitope has the amino acid sequence TEVKAAAADTYLKP (SEQ ID NO:2).
18. The EPI of paragraph 16 or 17, wherein the peptide ligand comprises the amino acid sequence LLFFF (SEQ ID NO:5).
19. The EPI of any one of paragraphs 1-12 or 14, wherein the target molecule is *Staphylococcus aureus* peptidoglycan.
20. The EPI of paragraph 19, wherein the target molecule is methicillin-resistant *Staphylococcus aureus* peptidoglycan.
21. The EPI of paragraph 19 or 20, wherein the peptide ligand comprises the amino acid sequence kpdew (SEQ ID NO:23) or akkrp (SEQ ID NO:34).
22. The EPI of any one of paragraphs 1-21, wherein the antibody-recruiting moiety comprises an epitope recognized by an antibody that mediates recognition and phagocytosis of the target by an immune cell.
23. The EPI of paragraph 22, wherein the epitope recognized by an antibody that mediates recognition and phagocytosis of the target by an immune cell is an immunogen endogenously recognized by a mammalian immune system.
24. The EPI of paragraph 22 or 23, wherein the epitope recognized by an antibody that mediates recognition and phagocytosis of the target by an immune cell is an immunogen endogenously recognized by a human immune system.
25. The EPI of any one of paragraphs 22-24, wherein the epitope recognized by an antibody that mediates recognition and phagocytosis of the target by an immune cell is 2,4-dinitrophenyl (DNP), alpha-galactose, galactose(alpha1-3)galactose, beta-lactam, 1,3-diketone, avidin, fluorescein, fluorescein-DNP, or nitrophenol.
26. The EPI of paragraphs 1-25, wherein the peptide ligand is comprised in a multi-ligand, wherein the multi-ligand further comprises a second ligand, wherein the second ligand has affinity for a second epitope on the target molecule, wherein the second epitope is exposed on the surface of the target, wherein the peptide ligand and the second ligand are covalently linked to each other, wherein the multi-ligand can simultaneous bind to the epitope and to the second epitope on the target molecule.
27. A composition comprising the EPI of any one of paragraphs 1-26.
28. A method of stimulating an immune reaction to a microorganism in a subject, the method comprising administering a composition of paragraph 27 to the subject, wherein the microorganism in the subject is the target of the EPI of the composition.
29. The method of paragraph 28, wherein the microorganism in the subject is resistant to one or more antibiotics.
30. The method of paragraph 28 or 29, wherein the microorganism in the subject is resistant to one or more classes of antibiotics.
31. The method of any one of paragraphs 28-30, wherein the microorganism in the subject is multidrug-resistant.
32. The method of any one of paragraphs 28-31, wherein the microorganism is a bacterium or a fungal cell.
33. The method of any one of paragraphs 28-32, wherein the microorganism is a Gram-negative bacterium.
34. The method of any one of paragraphs 28-33, wherein the microorganism is in the genus *Klebsiella, Salmonella, Escherichia, Staphylococcus, Legionella, Pseudomonas, Haemophilus, Helicobacter, Vibrio, Acinetobacter, Bordetella, Campylobacter, Citrobacter, Enterobacter, Serratia, Shigella, Yersinia*, or *Neisseria*.
35. The method of any one of paragraphs 28-34, wherein the microorganism is in the species *Klebsiella* spp., *Salmonella* spp., *Escherichia coli, Staphylococcus* spp., *Legionella pneumophila, Pseudomonas aeruginosa, Haemophilus influenza, Helicobacter pylori, Vibrio cholerae, Acinetobacter* spp., *Bordetella pertus-* sis, *Campylobacter* spp., *Citrobacter* spp., *Enterobacter* spp., *Serratia marcescens*, *Shigella* spp., *Yersinia* spp., or *Neisseria* spp.
36. The method of any one of paragraphs 28-35, wherein the microorganism is *Klebsiella pneumoniae*.
37. The method of any one of paragraphs 28-35, wherein the microorganism is *Staphylococcus aureus*.
38. The method of any one of paragraphs 28-34, wherein the microorganism is in the family Enterobacteriaceae.
39. A method of identifying the peptide ligand of an EPI of any one of paragraphs 7-26, the method comprising:
(a) selecting a protein that is highly expressed in the microorganism and that at least a part of is exposed on the surface of the microorganism, wherein the selected protein is the target molecule;
(b) selecting the epitope by identifying amino acid sequences of the selected protein that are predicted both to be surface-exposed and to have a low homology to the human proteome relative to other amino acid sequences of the selected protein and selecting one of the identified amino acid sequences as the epitope;
(c) contacting a polypeptide fragment with a plurality of candidate peptides, wherein the polypeptide fragment comprises the epitope, wherein the epitope is modified or substituted with (i) a group comprising an azido or alkynyl group and (ii) a label, wherein the candidate peptides all comprise an alkynyl group if the epitope has an azido group or an azido group if the epitope has an alkynyl group; and
(d) incubating the polypeptide fragment and the candidate peptides to allow formation of a triazole linkage between the polypeptide fragment and one of the candidate peptides, wherein a candidate peptide that forms a triazole linkage with the polypeptide fragment is identified as the peptide ligand.
40. The method of paragraph 39, wherein the group comprising an azido or alkynyl group is an artificial amino acid.
41. The method of paragraph 40, wherein the artificial amino acid is propargylglycine (Pra).
42. The method of paragraph 39, wherein the epitope comprises a phosphorylated amino acid, wherein the group comprising an azido or alkynyl group is a metalorganic molecule that selectively binds to the phospho group on the phosphorylated amino acid.
43. The method of paragraph 42, wherein the metalorganic molecule comprises the label.
44. The method of paragraph 43, wherein the label is biotin.
45. The method of paragraph 42, wherein the metalorganic molecule comprises an azido group.
46. The method of paragraph 39, wherein the label is biotin.
47. The method of paragraph 39 further comprising:
selecting a candidate peptide linked to the polypeptide fragment via a triazole linkage as the peptide ligand; and
sequencing the peptide ligand.
48. The method of paragraph 47, wherein the candidate peptide is selected by selecting labeled candidate peptides.
49. The method of paragraph 39, wherein the method further comprises testing the peptide ligand for binding to the target molecule.

EXAMPLES

Example 1: Antibody-Recruiting Protein-Catalyzed Capture Agents (AR-PCCs) Targeting *Klebsiella pneumoniae*

Epitope-targeted immunostimulants (EPIs) have been developed that combine a ligand specific for an epitope of a target molecule of interest with an antibody-recruiting molecule (ARM). Such EPIs can bind with high affinity and specificity to a target and thereby recruit antibodies to the target, with the result that an immune response to the target is enhanced. Specifically, reported herein is a generalizable combined computational and synthetic approach, called antibody-recruiting protein-catalyzed capture agents (AR-PCCs), which are a specific form of EPI. In a proof of concept demonstration, combinatorial PCC technology was applied to identify macrocyclic peptide ligands against highly conserved surface protein epitopes of carbapenem-resistant *Klebsiella pneumoniae*, an opportunistic gram-negative pathogen with drug resistant strains. Multi-omic data combined with bioinformatic analyses was used to identify epitopes of the highly expressed MrkA surface protein of *K. pneumoniae* for targeting in PCC screens. The top-performing ligand exhibited high-affinity ($EC_{50}$~50 nM) to full-length MrkA, and selectively bound to MrkA-expressing *K. pneumoniae*, but not to other pathogenic bacterial species. AR-PCCs that bear a hapten moiety promoted antibody recruitment to *K. pneumoniae*, leading to enhanced phagocytosis and phagocytic killing by macrophages. The rapid development of this highly targeted antibiotic shows that the integrated computational and synthetic toolkit described here can be used for the accelerated production of antibiotics against drug resistant bacteria and other microorganisms and viruses.

It was realized that a new class of highly targeted antibiotics could be made that combined immunostimulation with specific targeting of a target. Called epitope-targeting immunostimulants (EPIs), these contain a ligand to an epitope on a target and an antibody-recruiting molecule (ARM). A particular form of EPI called antibody-recruiting protein-catalyzed capture agents (AR-PCC) was demonstrated, and it was realized that these could be rapidly developed against a specified drug-resistant bacterium (FIG. 1). AR-PCCs consist of two molecular motifs. The first is a macrocyclic polypeptide ligand (the PCC) developed against a designated epitope of a specific surface protein on a microbial or viral target. The second is an antibody-recruiting (AR) label on the PCC that promotes phagocytosis of the pathogen by innate immune cells (FIG. 1). To generate the AR-PCC ligand, the recently reviewed (41), all synthetic epitope-targeted protein-catalyzed capture agent (PCC) method (42-45) was used and coupled with a bioinformatics approach to identify epitopes for targeting. By targeting highly exposed, antigenic epitopes of the Type 3 Fimbrial Shaft (MrkA) surface protein of *K. pneumoniae*, a small macrocyclic peptide binder was developed in a single generation screen. That binder exhibits high affinity for the MrkA protein, high selectivity for carbapenem-resistant *K. pneumoniae*, and, when labeled with the AR tag, promotes macrophage-mediated phagocytosis of the pathogen.

This work demonstrates that AR-PCCs can be used to target multi-drug resistant *K. pneumoniae*, and that the basic technology provides a route towards drugging "undruggable" pathogenic bacteria.

Results and Discussion
Multi-Omic Analyses to Select Target a Protein on *K. pneumoniae*

It was realized that development of AR-PCCS to particular targets can be made more efficient and rapid by selecting particular targets, and particular epitopes on those targets, that are more likely to yield accessible and effective targets for PCC-targeting. In this example, an algorithm was developed to identify protein targets, and epitopes on those targets, for drugging *K. pneumoniae* using AR-PCCs. Traditional drugging strategies tend to rely on disrupting the function of, for example, an enzyme by competing for occupancy within a strategic hydrophobic binding pocket. The requirements of the discovered target-epitope selection algorithm are very different. Instead, favorable aspects of target proteins are high expression levels on only the pathogen of interest, plus localization of that protein to the outer membrane or extracellular space of the pathogen. Further, once such a target protein is identified, there are additional considerations regarding which epitopes of that protein present the greatest opportunities for exploiting AR-PCCs.

The flow diagram in FIG. 2A delineates the strategy for identifying MrkA as an ideal target protein. Protein expression levels can vary across environments and growth phases, so the transcriptional data reported by Guilhen et al. (46) was analyzed to identify proteins with consistently high transcript levels across three major life phases of *K. pneumoniae*: exponential phase, stationary phase, and biofilms (including detached cells) (see Materials and Methods section). Briefly, focus was put on the top 10% of highly-expressed genes across these life phases (515 genes out of 5146 genes in the transcriptomics dataset). Subsequent cross-referencing of these 515 genes with proteomics-derived information about the localization of *K. pneumoniae* proteins (47-49) elucidated 13 highly expressed genes that encode proteins localized to the outer membrane or extracellular space. A literature search (see Materials and Methods section for specific references) then narrowed the selection by prioritizing essential virulence- and pathogenicity-related genes as well as protein orientation in the outer membrane, to five proteins: (i) FhuA, a siderophore, (ii) Lpp, a lipoprotein, (iii) Pal, a peptidoglycan-associated lipoprotein, (iv) NlpD, a lipoprotein, and (v) MrkA, a subunit of the type 3 fimbriae. Ultimately, MrkA was chosen as a target due to its key roles in infection and persistence (50), its presence in the majority of sequenced *K. pneumoniae* strains (51-53), and, critically, its location in fimbrial rods. These rods are large extracellular structures (0.5-2 μm long, 4-to-5 nm in diameter) (54, 55) that are each comprised of up to 1,000 s of MrkA copies (56).

The selection of target epitopes on MrkA is illustrated in FIG. 2B. Selection of surface exposed epitopes would be aided by protein structure, but no published structures exist for MrkA. As a surrogate, bioinformatics tools were employed to survey MrkA for epitopes with high surface exposures and low homology with the human proteome. B-cell antigenicity was also mapped, but wasn't a critical selection consideration.

The surface exposure, homology, and antigenicity of all 14-residue epitopes on the MrkA sequence were predicted and superimposed in FIG. 2B. Surface-exposure and antigenicity were calculated by averaging the predicted values assigned to each residue in the full-length MrkA sequence (by NetSurfP-2.0 or BepiPred-2.0) (57, 58) over the entire 14-residue epitope, while homology was predicted by comparing each 14-residue epitope with the human proteome using BlastP2.0 with parameters defined in the heuristic string method by Berglund et al. (59). This homology search yielded many partial matches per MrkA epitope, and the "maximum homology" value plotted in FIG. 2B represents the percentage overlap with the best match. Predicted and averaged values from these analyses are tabulated in Table 1. The plot in FIG. 2B reveals several regions containing epitopes of high (>60%) predicted surface exposure (FIG. 2B, green line) and relatively low (~50-55%) maximum homology to the human proteome (FIG. 2B, blue bars). Note that epitopes in surface-exposed regions range in predicted antigenicity from 0 to 100%.

TABLE 1

Predicted and average surface exposure, antigenicity and maximum homology for individual amino acids and 14-mer epitopes of MrkA (SEQ ID NO: 72).

| | | Predicted quantities | | | | |
|---|---|---|---|---|---|---|
| | | Amino acid | | | Epitope (14-mer), starting at residue # | |
| Residue # | Residue | Pred. Antigen. | Pred. Surf.-Exp. | Avg. Surf.-Exp. | Avg. Antigen. | Max Homol. (%) |
| 1 | M | 0 | 1 | 29 | 0 | 57 |
| 2 | K | 0 | 1 | 21 | 0 | 64 |
| 3 | K | 0 | 1 | 14 | 0 | 71 |
| 4 | V | 0 | 1 | 7 | 0 | 71 |
| 5 | L | 0 | 0 | 0 | 0 | 71 |
| 6 | L | 0 | 0 | 0 | 0 | 64 |
| 7 | S | 0 | 0 | 0 | 0 | 57 |
| 8 | A | 0 | 0 | 0 | 0 | 57 |
| 9 | A | 0 | 0 | 0 | 0 | 57 |
| 10 | M | 0 | 0 | 0 | 0 | 57 |
| 11 | A | 0 | 0 | 0 | 7 | 57 |
| 12 | T | 0 | 0 | 0 | 14 | 57 |
| 13 | A | 0 | 0 | 7 | 21 | 57 |
| 14 | F | 0 | 0 | 7 | 29 | 57 |
| 15 | F | 0 | 0 | 14 | 36 | 57 |
| 16 | G | 0 | 0 | 21 | 43 | 64 |
| 17 | M | 0 | 0 | 21 | 50 | 71 |
| 18 | T | 0 | 0 | 29 | 50 | 71 |
| 19 | A | 0 | 0 | 29 | 50 | 71 |
| 20 | A | 0 | 0 | 36 | 50 | 71 |
| 21 | H | 0 | 0 | 36 | 50 | 64 |
| 22 | A | 0 | 0 | 43 | 50 | 64 |
| 23 | A | 0 | 0 | 43 | 50 | 57 |
| 24 | D | 1 | 0 | 50 | 50 | 64 |
| 25 | T | 1 | 0 | 50 | 43 | 64 |
| 26 | T | 1 | 1 | 57 | 36 | 64 |
| 27 | V | 1 | 0 | 57 | 29 | 64 |
| 28 | G | 1 | 1 | 64 | 21 | 64 |
| 29 | G | 1 | 1 | 64 | 14 | 64 |
| 30 | G | 1 | 0 | 57 | 7 | 50 |
| 31 | Q | 0 | 1 | 64 | 0 | 64 |
| 32 | V | 0 | 0 | 57 | 0 | 64 |
| 33 | N | 0 | 1 | 64 | 0 | 64 |
| 34 | F | 0 | 0 | 64 | 0 | 57 |
| 35 | F | 0 | 1 | 71 | 7 | 57 |
| 36 | G | 0 | 0 | 71 | 14 | 57 |
| 37 | K | 0 | 1 | 79 | 21 | 64 |
| 38 | V | 0 | 0 | 79 | 29 | 64 |
| 39 | T | 0 | 1 | 86 | 36 | 64 |
| 40 | D | 0 | 1 | 86 | 43 | 57 |
| 41 | V | 0 | 1 | 79 | 50 | 57 |
| 42 | S | 0 | 1 | 79 | 50 | 57 |
| 43 | C | 0 | 0 | 71 | 50 | 64 |
| 44 | T | 0 | 1 | 79 | 50 | 57 |
| 45 | V | 0 | 0 | 71 | 50 | 57 |
| 46 | S | 0 | 1 | 79 | 50 | 57 |
| 47 | V | 0 | 1 | 79 | 50 | 71 |
| 48 | N | 1 | 1 | 71 | 57 | 64 |
| 49 | G | 1 | 1 | 71 | 50 | 64 |
| 50 | Q | 1 | 1 | 71 | 50 | 71 |
| 51 | G | 1 | 1 | 71 | 50 | 57 |
| 52 | S | 1 | 1 | 71 | 50 | 64 |
| 53 | D | 1 | 1 | 64 | 50 | 57 |

TABLE 1-continued

Predicted and average surface exposure, antigenicity and maximum homology for individual amino acids and 14-mer epitopes of MrkA (SEQ ID NO: 72).

| | | Predicted quantities | | | | |
|---|---|---|---|---|---|---|
| | | Amino acid | | | Epitope (14-mer), starting at residue # | |
| Residue # | Residue | Pred. Antigen. | Pred. Surf.-Exp. | Avg. Surf.-Exp. | Avg. Antigen. | Max Homol. (%) |
| 54 | A | 1 | 0 | 64 | 50 | 57 |
| 55 | N | 0 | 1 | 71 | 50 | 64 |
| 56 | V | 0 | 0 | 71 | 57 | 64 |
| 57 | Y | 0 | 1 | 79 | 64 | 64 |
| 58 | L | 0 | 0 | 79 | 71 | 64 |
| 59 | S | 0 | 1 | 86 | 79 | 71 |
| 60 | P | 0 | 1 | 86 | 86 | 71 |
| 61 | V | 1 | 0 | 86 | 93 | 64 |
| 62 | T | 0 | 1 | 93 | 93 | 64 |
| 63 | L | 1 | 1 | 93 | 100 | 71 |
| 64 | T | 1 | 1 | 93 | 100 | 71 |
| 65 | E | 1 | 1 | 93 | 100 | 71 |
| 66 | V | 1 | 0 | 93 | 93 | 64 |
| 67 | K | 1 | 1 | 93 | 86 | 57 |
| 68 | A | 1 | 1 | 93 | 79 | 57 |
| 69 | A | 1 | 1 | 86 | 71 | 57 |
| 70 | A | 1 | 1 | 86 | 64 | 57 |
| 71 | A | 1 | 1 | 79 | 57 | 64 |
| 72 | D | 1 | 1 | 79 | 50 | 64 |
| 73 | T | 1 | 1 | 79 | 43 | 64 |
| 74 | Y | 1 | 1 | 71 | 43 | 50 |
| 75 | L | 1 | 1 | 71 | 43 | 57 |
| 76 | K | 1 | 1 | 71 | 43 | 57 |
| 77 | P | 1 | 1 | 71 | 43 | 57 |
| 78 | K | 1 | 1 | 71 | 43 | 57 |
| 79 | S | 0 | 1 | 71 | 43 | 57 |
| 80 | F | 0 | 0 | 71 | 50 | 57 |
| 81 | T | 0 | 1 | 79 | 57 | 57 |
| 82 | I | 0 | 0 | 79 | 64 | 50 |
| 83 | D | 0 | 1 | 86 | 71 | 57 |
| 84 | V | 0 | 0 | 86 | 79 | 57 |
| 85 | S | 0 | 1 | 86 | 86 | 57 |
| 86 | N | 0 | 1 | 86 | 86 | 57 |
| 87 | C | 1 | 0 | 86 | 86 | 57 |
| 88 | Q | 1 | 1 | 86 | 79 | 57 |
| 89 | A | 1 | 1 | 86 | 71 | 57 |
| 90 | A | 1 | 1 | 79 | 64 | 57 |
| 91 | D | 1 | 1 | 71 | 57 | 71 |
| 92 | G | 1 | 1 | 64 | 50 | 57 |
| 93 | T | 1 | 1 | 64 | 43 | 57 |
| 94 | K | 1 | 1 | 57 | 36 | 64 |
| 95 | Q | 1 | 1 | 50 | 36 | 64 |
| 96 | D | 1 | 1 | 50 | 36 | 64 |
| 97 | D | 1 | 1 | 50 | 36 | 57 |
| 98 | V | 1 | 0 | 43 | 36 | 57 |
| 99 | S | 0 | 1 | 50 | 36 | 57 |
| 100 | K | 0 | 1 | 50 | 43 | 57 |
| 101 | L | 0 | 0 | 50 | 50 | 57 |
| 102 | G | 0 | 1 | 57 | 57 | 57 |
| 103 | V | 0 | 0 | 57 | 64 | 64 |
| 104 | N | 0 | 0 | 64 | 71 | 64 |
| 105 | W | 0 | 0 | 64 | 79 | 57 |
| 106 | T | 0 | 1 | 71 | 86 | 64 |
| 107 | G | 0 | 0 | 71 | 93 | 57 |
| 108 | G | 1 | 0 | 71 | 100 | 57 |
| 109 | N | 1 | 1 | 71 | 100 | 57 |
| 110 | L | 1 | 1 | 71 | 100 | 64 |
| 111 | L | 1 | 0 | 71 | 100 | 64 |
| 112 | A | 1 | 1 | 79 | 100 | 64 |
| 113 | G | 1 | 1 | 79 | 100 | 64 |
| 114 | A | 1 | 1 | 79 | 100 | 57 |
| 115 | T | 1 | 1 | 79 | 100 | 71 |
| 116 | S | 1 | 1 | 79 | 100 | 71 |
| 117 | K | 1 | 1 | 71 | 100 | 57 |
| 118 | Q | 1 | 0 | 71 | 93 | 64 |
| 119 | Q | 1 | 1 | 71 | 86 | 71 |
| 120 | G | 1 | 1 | 64 | 79 | 71 |
| 121 | Y | 1 | 0 | 57 | 71 | 57 |
| 122 | L | 1 | 0 | 57 | 64 | 57 |
| 123 | A | 1 | 1 | 57 | 57 | 57 |
| 124 | N | 1 | 1 | 50 | 50 | 57 |
| 125 | T | 1 | 1 | 43 | 43 | 64 |
| 126 | E | 1 | 1 | 43 | 36 | 57 |
| 127 | A | 1 | 1 | 43 | 36 | 57 |
| 128 | S | 1 | 1 | 43 | 36 | 57 |
| 129 | G | 1 | 1 | 43 | 36 | 57 |
| 130 | A | 1 | 0 | 43 | 36 | 57 |
| 131 | Q | 0 | 1 | 50 | 36 | 64 |
| 132 | N | 0 | 0 | 50 | 43 | 64 |
| 133 | I | 0 | 0 | 57 | 50 | 64 |
| 134 | Q | 0 | 0 | 64 | 57 | 64 |
| 135 | L | 0 | 0 | 71 | 64 | 71 |
| 136 | V | 0 | 0 | 71 | 71 | 57 |
| 137 | L | 0 | 0 | 79 | 79 | 57 |
| 138 | S | 0 | 0 | 86 | 86 | 57 |
| 139 | T | 0 | 1 | 93 | 93 | 64 |
| 140 | D | 1 | 1 | 93 | 100 | 64 |
| 141 | N | 1 | 1 | 93 | 100 | 64 |
| 142 | A | 1 | 1 | 93 | 100 | 57 |
| 143 | T | 1 | 1 | 93 | 100 | 64 |
| 144 | A | 1 | 1 | 93 | 100 | 71 |
| 145 | L | 1 | 1 | 93 | 100 | 64 |
| 146 | T | 1 | 1 | 93 | 100 | 64 |
| 147 | N | 1 | 1 | 93 | 100 | 57 |
| 148 | K | 1 | 1 | 93 | 100 | 57 |
| 149 | I | 1 | 0 | 93 | 100 | 57 |
| 150 | I | 1 | 1 | 100 | 100 | 57 |
| 151 | P | 1 | 1 | 100 | 100 | 64 |
| 152 | G | 1 | 1 | 100 | 100 | 64 |
| 153 | D | 1 | 1 | 100 | 100 | 64 |
| 154 | S | 1 | 1 | 100 | 100 | 57 |
| 155 | T | 1 | 1 | 100 | 100 | 64 |
| 156 | Q | 1 | 1 | 100 | 100 | 64 |
| 157 | P | 1 | 1 | 93 | 100 | 64 |
| 158 | K | 1 | 1 | 93 | 93 | 57 |
| 159 | A | 1 | 1 | 86 | 86 | 64 |
| 160 | K | 1 | 1 | 86 | 79 | 64 |
| 161 | G | 1 | 1 | 79 | 71 | 64 |
| 162 | D | 1 | 1 | 71 | 64 | 64 |
| 163 | A | 1 | 1 | 64 | 57 | 64 |
| 164 | S | 1 | 1 | 57 | 50 | 71 |
| 165 | A | 1 | 1 | 50 | 43 | 71 |
| 166 | V | 1 | 1 | 43 | 36 | 64 |
| 167 | A | 1 | 1 | 36 | 29 | 64 |
| 168 | D | 1 | 1 | 36 | 21 | 64 |
| 169 | G | 1 | 1 | 36 | 14 | 57 |
| 170 | A | 1 | 0 | 36 | 7 | 64 |

TABLE 1-continued

Predicted and average surface exposure, antigenicity and maximum homology for individual amino acids and 14-mer epitopes of MrkA (SEQ ID NO: 72).

| | | Predicted quantities | | | | |
|---|---|---|---|---|---|---|
| | | Amino acid | | | Epitope (14-mer), starting at residue # | |
| Residue # | Residue | Pred. Antigen. | Pred. Surf.-Exp. | Avg. Surf.-Exp. | Avg. Antigen. | Max Homol. (%) |
| 171 | R | 0 | 1 | 43 | 7 | 57 |
| 172 | F | 0 | 0 | 43 | 14 | 57 |
| 173 | T | 0 | 1 | 43 | 14 | 64 |
| 174 | Y | 0 | 0 | 43 | 14 | 64 |
| 175 | Y | 0 | 0 | 50 | 14 | 64 |
| 176 | V | 0 | 0 | 57 | 14 | 64 |
| 177 | G | 0 | 0 | 64 | 14 | 64 |
| 178 | Y | 0 | 0 | 64 | 14 | 71 |
| 179 | A | 0 | 0 | 71 | 14 | 71 |
| 180 | T | 0 | 0 | 71 | 14 | 71 |
| 181 | S | 0 | 1 | 79 | 14 | 64 |
| 182 | A | 0 | 1 | 71 | 14 | 57 |
| 183 | P | 0 | 1 | 71 | 14 | 57 |
| 184 | T | 1 | 1 | 64 | 14 | 57 |
| 185 | T | 0 | 1 | 57 | 7 | 57 |
| 186 | V | 0 | 0 | 50 | 0 | 50 |
| 187 | T | 0 | 1 | 57 | 0 | 57 |
| 188 | T | 0 | 1 | 50 | 0 | 50 |
| 189 | G | 0 | 1 | 50 | 0 | 50 |
| 190 | V | 0 | 1 | — | — | — |
| 191 | V | 0 | 0 | — | — | — |
| 192 | N | 0 | 1 | — | — | — |
| 193 | S | 0 | 0 | — | — | — |
| 194 | Y | 0 | 1 | — | — | — |
| 195 | A | 0 | 0 | — | — | — |
| 196 | T | 0 | 1 | — | — | — |
| 197 | Y | 0 | 0 | — | — | — |
| 198 | E | 0 | 0 | — | — | — |
| 199 | I | 0 | 0 | — | — | — |
| 200 | T | 0 | 1 | — | — | — |
| 201 | Y | 0 | 0 | — | — | — |
| 202 | Q | 0 | 1 | — | — | — |

Four epitopes, indicated by arrows in FIG. 2B, were selected based on their predicted high surface exposures (>60%), limited maximum homology (57-71%), and broad range of antigenicity values. The sequences of these candidate epitopes are shown in FIG. 2B. Importantly, the MrkA protein and candidate epitopes are highly conserved among *K. pneumoniae* strains. In fact, the MrkA sequence (with 202 amino acids (SEQ ID NO:72)) is 95% conserved across 380 analyzed *K. pneumoniae* strains (60, 61).

Epitope-Targeted PCC Ligands Against the MrkA Protein

AR-PCC ligands against the four selected epitopes were identified from a combinatorial library of macrocyclic peptides by using the epitope-targeted PCC method (42-45). This method exploits non-catalyzed click chemistry via an in situ click screen. For the screen, an alkyne-presenting, one-bead one-compound (OBOC) combinatorial library of approximately 1M peptide macrocycles with a 5-residue variable region is screened against synthetic variants of the epitopes (SynEps). Each SynEp is designed with a biotin assay handle and a strategically incorporated azide click handle (42). The structures of the four SynEps are shown below. SynEp 1 is SEQ ID NO:38, SynEp 2 is SEQ ID NO:39, SynEp 3 is SEQ ID NO:40, and SynEp 4 is SEQ ID NO:41.

MrkA SynEp 1-Biotin-peg5-FFGKVT(V→Z)SCTVSV

Chemical Formula: $C_{91}H_{146}N_{22}O_{28}S_2$
Exact Mass: 2059.01
Molecular Weight: 2060.42

-continued
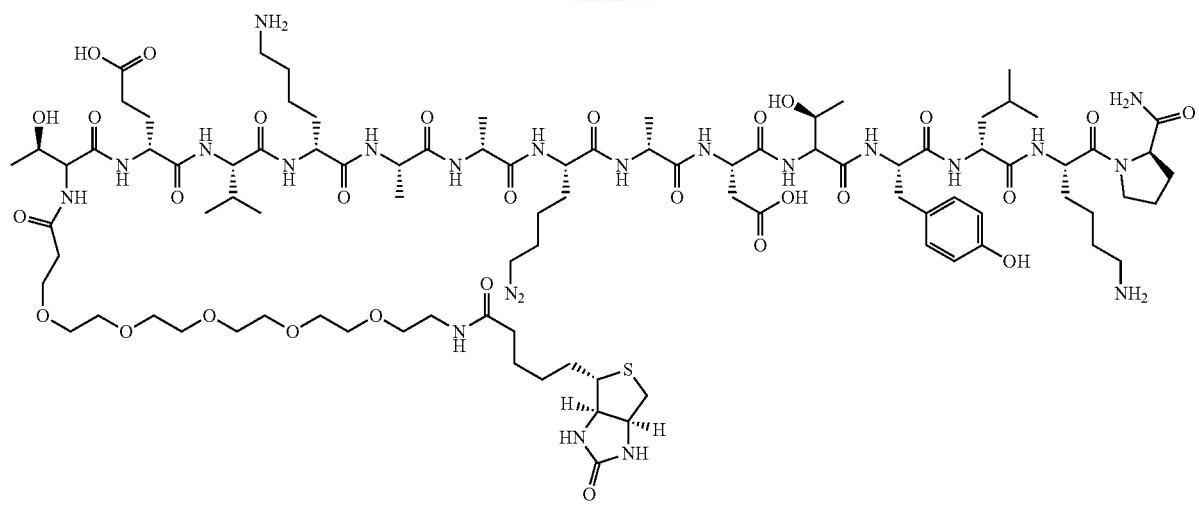
MrkA SynEp 2-Biotin-peg5-TEVKAA(A→Z)ADTYLKP
Chemical Formula: $C_{92}H_{153}N_{23}O_{29}S$
Exact Mass: 2076.09
Molecular Weight: 2077.43
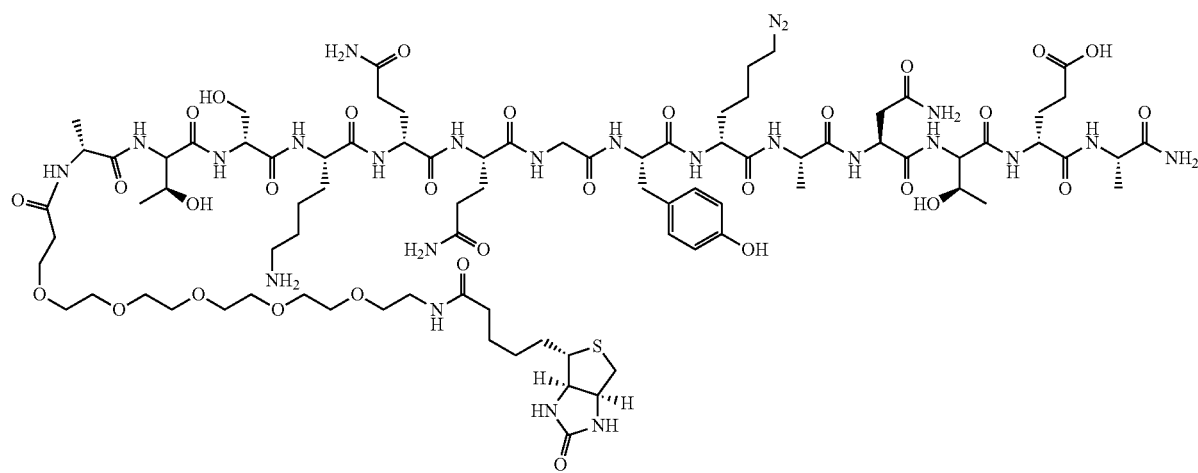
MrkA SynEp 3-Biotin-peg5-ATSKQQGY(L→Z)ANTEA
Chemical Formula: $C_{85}H_{139}N_{25}O_{31}S$
Exact Mass: 2037.98
Molecular Weight: 2039.25

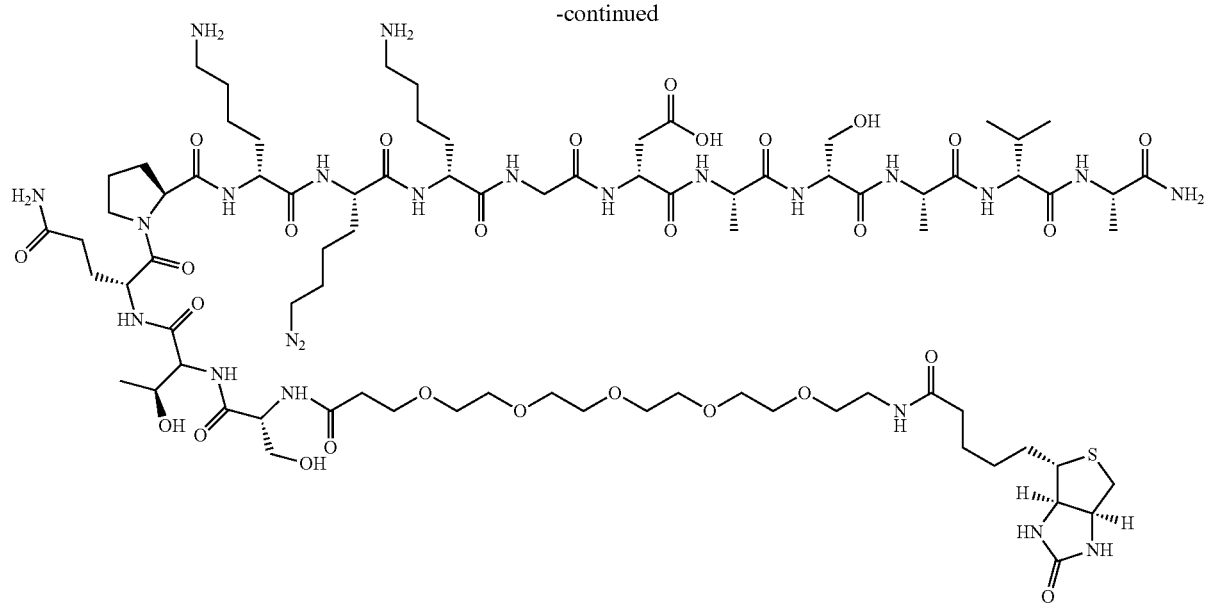

MrkA SynEp 4-Biotin-peg5-STQPK(A→Z)KGDASAVA

Chemical Formula: $C_{61}H_{140}N_{24}O_{28}S$
Exact Mass: 1929.00
Molecular Weight: 1930.21

The concept behind the screen is that select OBOC library elements will bind to a SynEp in just the right orientation so as to promote the azide-acetylene click reaction, thus covalently linking the SynEp to the bead. This product can be detected using the biotin assay handle on the SynEp, coupled with enzymatic amplification, to add color to the hit bead. Prior to screening SynEps, the library is cleared of beads that bound the detection antibody, streptavidin-alkaline phosphatase (SAv-AP). Hit beads are separated, and the hit candidate peptides are cleaved and sequenced using tandem mass spectrometry.

For this work, a single screen of the OBOC library against all four target MrkA SynEps was performed. The chemical structure of macrocyclic peptide ligands to MrkA, in which each $X_i$ represents one of 17 common amino acids (excluding methionine, cysteine, and isoleucine) is:

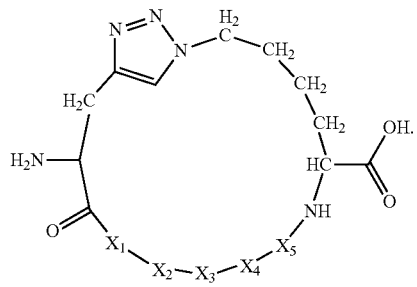

Figure 8:
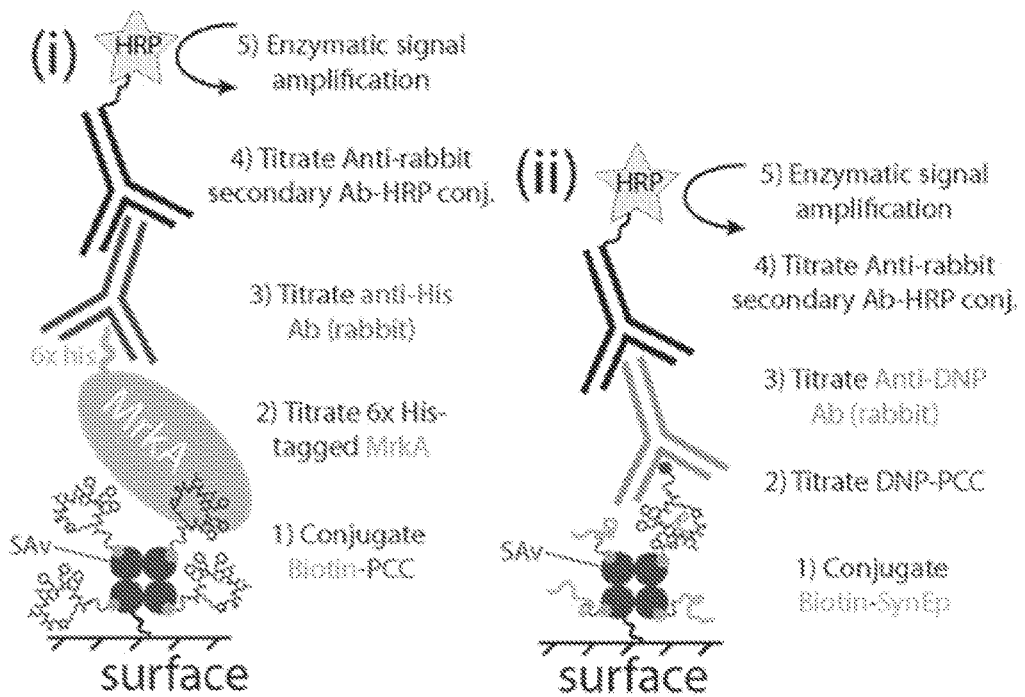
FIG. 8 is schematic diagrams of the sandwich ELISA assay formats used to test the binding affinities of PCC ligands to (i) full-length MrkA and (ii) SynEps. The relative sizes of the molecules in these illustrations are not to scale.

The screen yielded 26 hits (Table 2) that were sequenced, scaled up, and tested for binding to full-length recombinant MrkA in solution by single-point sandwich Enzyme-linked immunoassays (ELISAs) (FIG. 8). HPraGly is present before X1 in each peptide and Az4 follows X5 in each peptide.

TABLE 2

Sequences of the 26 different macrocyclic peptide ligands from the in situ click screen of four target epitopes on MrkA.

| Hit # | X1 | X2 | X3 | X4 | X5 | SEQ ID NO: |
|---|---|---|---|---|---|---|
| 1 | F | Y | T | K | G | 42 |
| 2 | E | Y | E | G | K | 43 |
| 3 | P | W | N | K | G | 44 |
| 4.1 | S | W | T | G | E | 45 |
| 4.2 | R | H | P | G | E | 46 |
| 5 | N | R | T | G | P | 47 |
| 6 | P | R | E | G | P | 48 |
| 7 | S | N | F | G | P | 49 |
| 8 | E | K | T | P | G | 50 |
| 9 | K | G | F | P | G | 51 |
| 10 | G | G | F | N | A | 52 |
| 11 | N | G | P | V | H | 53 |
| 12 | W | Y | K | G | P | 54 |
| 13 | W | D | Y | K | G | 55 |
| 14 | Y | R | H | L | G | 56 |
| 15 | G | V | H | R | L | 57 |
| 16 | G | V | V | E | K | 58 |
| 17 | G | L | T | H | A | 59 |
| 18 | S | L | G | L | T | 60 |
| 19 | L | L | F | F | F | 5 |
| 20 | T | T | F | F | F | 35 |
| 21 | K | P | A | G | — | 61 |
| 22 | A | K | P | E | P | 62 |
| 23 | E | W | V | S | A | 63 |
| 24 | E | F | S | G | V | 64 |
| 25 | D | G | T | A | L | 65 |
| 26.1 | V | V | N | L | P | 66 |
| 26.2 | T | P | N | L | P | 67 |
| 26.3 | R | P | E | G | P | 68 |

The top-performing ligand had was cy(LLFFF) (SEQ ID NO:5; structure in FIG. 3A inset), where "cy" represents azidolysine-propargylglycine cyclization and the letters represent single-letter amino acid codes. This ligand exhibited an $EC_{50}$ value of 50 nM to full-length recombinant MrkA protein (FIG. 3A). Additional ligands, but with lower affinities to MrkA, were also discovered, with sequences cy(TTFFF) (SEQ ID NO:35), cy(YRHLG) (SEQ ID NO:56) and cy(GVHRL) (SEQ ID NO:57). Based upon chemical homology, cy(TTFFF) (SEQ ID NO:35) likely binds the same epitope as cy(LLFFF) (SEQ ID NO:5), but cy(YRHLG) (SEQ ID NO:56) and cy(GVHRL) (SEQ ID NO:57) presumably bind a different one.

The particular epitope target to which cy(LLFFF) (SEQ ID NO:5) binds was next identified. A sandwich ELISA was performed in which the biotinylated SynEps were immobilized. The lead ligand cy(LLFFF) (SEQ ID NO:5), conjugated to a 2,4-dinitrophenyl (DNP) moiety, was titrated at a 500 nM concentration, and anti-DNP was used as a detection antibody. The results in FIG. 3B show the highest signals from SynEp 2 (TEVKAAZADTYLKP; SEQ ID NO:39). A background level for this assay was established using a biotinylated 6-mer polyethylene glycol (biotin-PEG$_6$). Negative signals observed for the case of SynEp 1 indicate that this SynEp blocks non-specific binding of cy(LLFFF) (SEQ ID NO:5) or anti-DNP more than the biotin-peg6 control. As the native epitope for SynEp1 has a GRAVY score of 1.01, while the native versions of other SynEps range between −0.9 and −0.28, the negative ELISA signals may arise from the relatively high hydrophobicity of SynEp 1 versus others. The blocking may also result from the reactivity of the cysteine residue in SynEp 1. Overall, these findings suggest that cy(LLFFF) (SEQ ID NO:5) binds the epitope TEVKAAAADTYLKP (SEQ ID NO:2) in native MrkA. This epitope is 100% conserved across the 380 *K. pneumoniae* isolates analyzed, suggesting that cy(LLFFF) (SEQ ID NO:5) would bind the entire cohort of these *K. pneumoniae* strains.

Figure 4A:
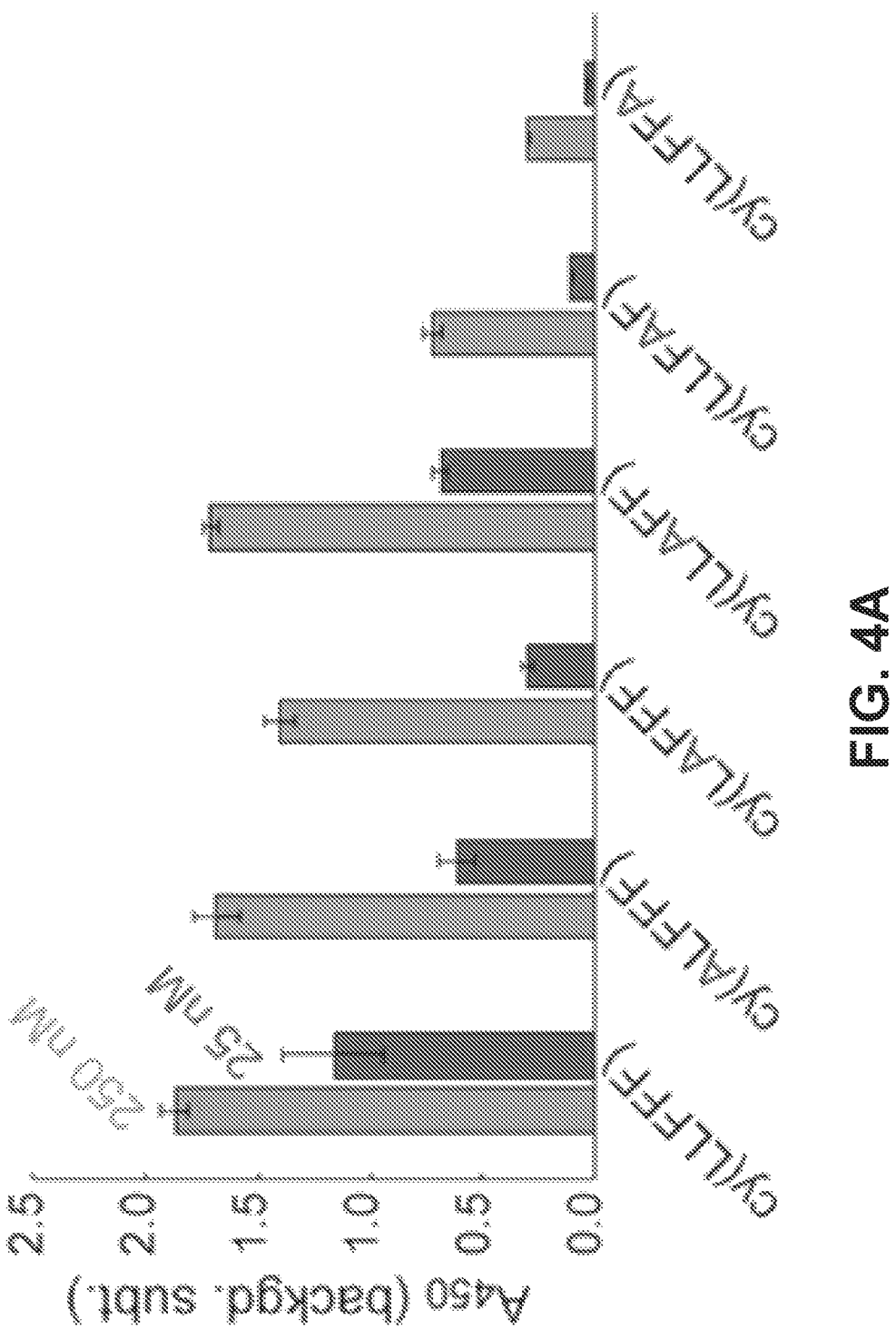
FIGS. 4A and 4B show features and optimization the cy(LLFFF) (SEQ ID NO: 5) ligand through strategic chemical modifications.

An alanine scan was performed to establish which residues of cy(LLFFF) (SEQ ID NO:5) contribute most to MrkA binding. In this assay, a sandwich ELISA is used to quantify the affinity of several cy(LLFFF) (SEQ ID NO:5) analogues, in which one residue is substituted with an alanine, towards full-length MrkA protein. The ELISA results in FIG. 4 show lower signal for every alanine-substituted cy(LLFFF) (SEQ ID NO:5) analogue compared to unmodified cy(LLFFF) (SEQ ID NO:5), establishing that the native compound has the highest affinity. Modestly lower binding is observed for cy(ALFFF) (SEQ ID NO:7), cy(LAFFF) (SEQ ID NO:8), and cy(LLAFF) (SEQ ID NO:9), but binding is substantially reduced for analogues with alanine substitutions at the C-terminal diphenylalanine motif. Thus, these two C-terminal phenylalanine residues (FIG. 3A, red arrows in inset) play critical roles in MrkA binding, and are targets for modifications to improve binding. Another important detail of these alanine scan results is a strong dependence of MrkA binding on the residue position, independent of residue type. For example, cy(LLAFF) (SEQ ID NO:9) and cy(LLFFA) (SEQ ID NO:11) have very different binding affinities, despite having the same phenylalanine-to-alanine substitution. This indicates that MrkA-binding is sequence dependent, suggesting selectivity of cy(LLFFF) (SEQ ID NO:5) for MrkA at the TEVKAAAADTYLKP epitope (SEQ ID NO:2).

Synthetic Modifications to Optimize AR-PCC Pharmacokinetics and Avidity

Figure 4B:
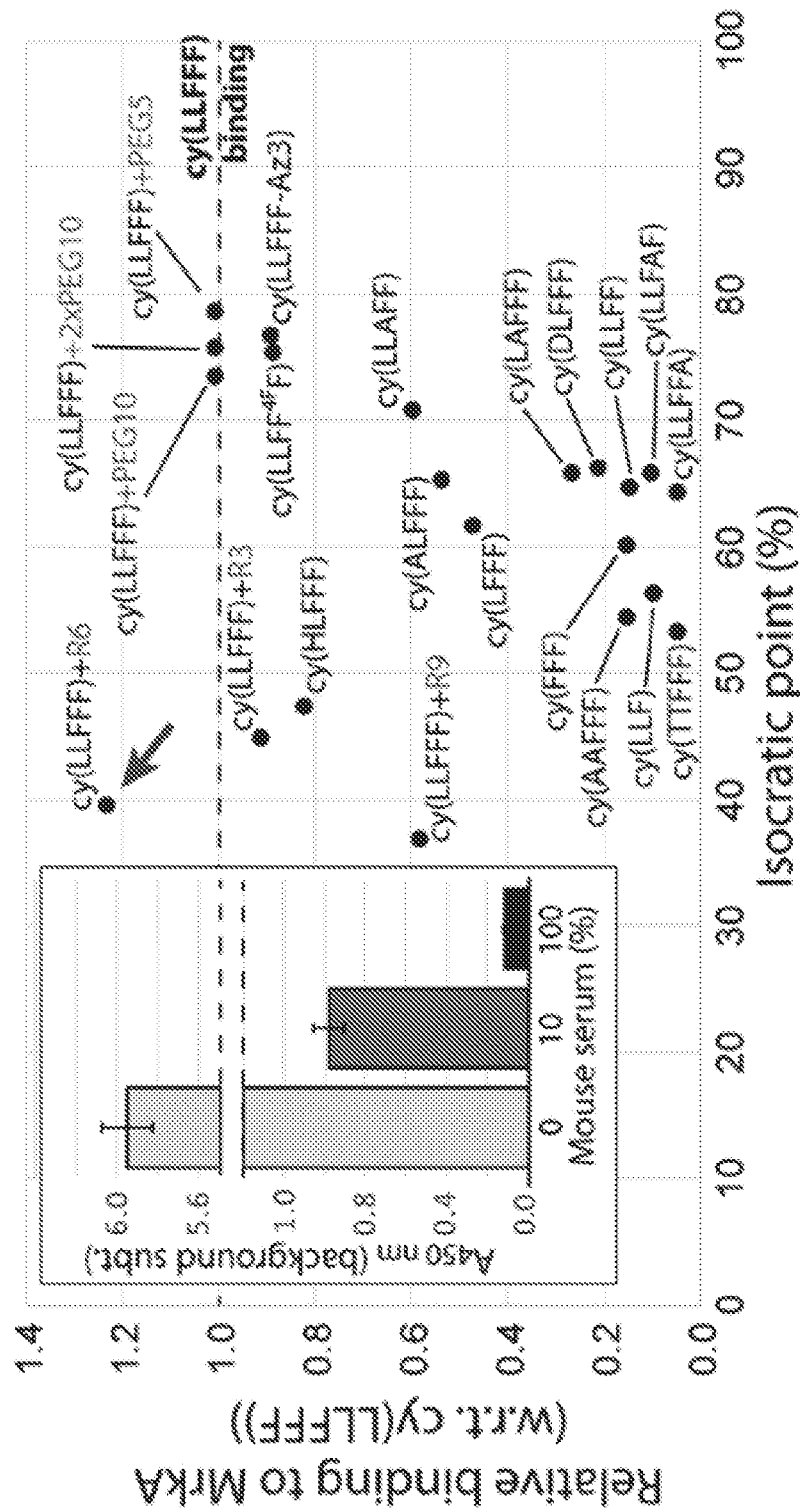

The efficacy of AR-PCCs in vivo will not only depend on target binding, but also pharmacokinetic (PK) properties, of which clearance pathway is an important parameter. Separate mouse studies indicate that PCCs with isocratic points (IPs) above 35% predominantly clear via the liver (i.e., hepatic clearance), while more hydrophilic compounds with lower isocratic points clear by the kidneys (i.e., renal clearance). Thus, the highly hydrophobic cy(LLFFF) (SEQ ID NO:5) ligand would likely exhibit hepatic clearance. To afford greater control over PK properties, synthetic modifications were explored to improve the hydrophilicity of cy(LLFFF) (SEQ ID NO:5), to favor renal clearance, while retaining the desired avidity characteristics. Modifications include single- and double-residue substitutions, residue removal, and the addition of non-ionic PEG and charged poly-arginine tags (Ri, where i represents the number of arginine). Results of this optimization are shown in FIG. 4B, which plots IP versus the affinity of the compound to MrkA, relative to cy(LLFFF) (SEQ ID NO:5). The same results are also tabulated in Table 3.

TABLE 3

Isocratic points and relative affinities of macrocyclic analogues of lead MrkA ligand cy(LLFFF) (SEQ ID NO: 5).

| ELISA Assay # | Compound Number (SEQ ID NO) | N-terminal tag | Cycle sequence | Isocratic point (%) | Relative affinity* | [MrkA] for ELISA | Modification |
| --- | --- | --- | --- | --- | --- | --- | --- |
| ELISA 1 | Ref. compound (74) | Bio-Peg10-peg10- | cy(X-LLFFF-Z) | 74.53 | 1.00 | N/A | Reference |
| ELISA 2 | Ref. compound (74) | Bio-peg10- | cy(X-LLFFF-Z) | 75.88 | 1.00 | 25 nM | Reference |
| | 2 (75) | Bio-peg10- | cy(X-ALFFF-Z) | 65.55 | 0.53 | 25 nM | L-to-A substitution |
| | 3 (76) | Bio-peg10- | cy(X-LAFFF-Z) | 66.00 | 0.26 | 25 nM | L-to-A substitution |
| | 4 (77) | Bio-peg10- | cy(X-LLAFF-Z) | 70.97 | 0.59 | 25 nM | F-to-A substitution |
| | 5 (78) | Bio-peg10- | cy(X-LLFAF-Z) | 66.00 | 0.10 | 25 nM | F-to-A substitution |
| | 6 (79) | Bio-peg10- | cy(Z-LLFFA-X) | 64.43 | 0.04 | 25 nM | F-to-A substitution |
| ELISA 3 | Ref. compound (74) | Bio-peg10- | cy(X-LLFFF-Z) | 75.88 | 1.00 | 50 nM | Reference |
| | 7 (80) | Bio-peg10- | cy(X-AAFFF-Z) | 54.65 | 0.15 | 50 nM | LL-to-AA substitution |
| | 8 (81) | Bio-peg10- | cy(X-LFFF-Z) | 61.84 | 0.46 | 50 nM | L removal |

TABLE 3-continued

Isocratic points and relative affinities of macrocyclic analogues of lead MrkA ligand cy(LLFFF) (SEQ ID NO: 5).

| ELISA Assay # | Compound Number (SEQ ID NO) | N-terminal tag | Cycle sequence | Isocratic point (%) | Relative affinity* | [MrkA] for ELISA | Modification |
|---|---|---|---|---|---|---|---|
| | 10 (82) | Bio-peg10- | cy(X-LLFFF-(Z3)) | 76.89 | 0.89 | 50 nM | Z-to-Z3 substitution (remove one methylene group) |
| | 11 (83) | Bio-peg10- | cy(X-LLFF4-Z) | 75.53 | 0.88 | 50 nM | F-to-4 substitution |
| ELISA 4 | Ref. compound (74) | Bio-peg5- | cy(X-LLFFF-Z) | 78.85 | 1.00 | 100 nM | Reference |
| | 13 (84) | Bio-peg5- | cy(X-TTFFF-Z) | 53.40 | 0.04 | 100 nM | LL-to-TT substitution |
| ELISA 5 | Ref. compound (74) | Bio-peg10- | cy(X-LLFFF-Z) | 75.88 | 1.00 | 25 nM | Reference |
| | 16 (74) | Bio-peg10-R3-peg10- | cy(X-LLFFF-Z) | 45.02 | 0.90 | 25 nM | Add-Peg10-R3 tag |
| | 17 (74) | Bio-peg10-R6-peg10- | cy(X-LLFFF-Z) | 39.82 | 1.22 | 25 nM | Add-Peg10-R6 tag |
| | 18 (74) | Bio-peg10-R9-peg10- | cy(X-LLFFF-Z) | 37.03 | 0.58 | 25 nM | Add-Peg10-R9 tag |
| ELISA 6 | Ref. compound (74) | Bio-peg10- | cy(X-LLFFF-Z) | 75.88 | 1.00 | 25 nM | Reference |
| | 19 (85) | Bio-peg10- | cy(X-HLFFF-Z) | 47.52 | 0.81 | 25 nM | Cationic residue substitution |
| | 20 (86) | Bio-peg10- | cy(X-DLFFF-Z) | 66.33 | 0.21 | 25 nM | Anionic residue substitution |
| | 21 (87) | Bio-peg10- | cy(X-LLFF-Z) | 64.99 | 0.14 | 25 nM | Residue removal |
| | 22 | Bio-peg10- | cy(X-LLF-Z) | 56.45 | 0.09 | 25 nM | Double residue removal |
| | 23 | Bio-peg10- | cy(X-FFF-Z) | 60.27 | 0.14 | 25 nM | Double residue removal |

*Relative affinity is the ratio of ELISA signal for a given compound versus that obtained from cy(LLFFF) (SEQ ID NO: 5) under the same assay conditions (e.g., MrkA concentration). A Relative Affinity value of < 1 reflects lower affinity to MrkA versus cy(LLFFF) (SEQ ID NO: 5).
**cy( ) indicates cyclization, X = propargylglycine, Z = Azidolysine, Z3 = azidonorvaline, 4 = 4-fluoro-phenylalanine Bio = biotin, Ri = polyarginine tag with i arginine residues, pegi = polyethylene glycol chain of length i. All amino acids represented by single-letter amino acid codes.

The cycle sequences in Table 3 are, from top to bottom, SEQ ID NOs: 74, 74, 75, 76, 77, 78, 79, 74, 80, 81, 82, 83, 74, 84, 74, 74, 74, 74, 74, 85, 86, 87.

Residue substitutions and removals categorically reduced affinity to MrkA, indicating that the structure of cy(LLFFF) (SEQ ID NO:5) compound is somewhat optimized to bind the TEVKAAAADTYLKP epitope (SEQ ID NO:2). These residue substitutions and removals provided up to about 30% reductions in IP versus cy(LLFFF) (SEQ ID NO:5). By comparison, the addition of polyarginine tags reduced the IP to near 40% without substantial loss in MrkA avidity (three leftmost data points in FIG. 4B). In fact, cy(LLFFF) (SEQ ID NO:5) with a hexa-arginine tag, "cy(LLFFF)+R6" (SEQ ID NO:16), shows a 22% stronger affinity to MrkA over cy(LLFFF) (SEQ ID NO:5) and had an isocratic point of near 40%, as indicated by the red arrow in FIG. 4B. This represents an improvement of ~35% versus the IP of unmodified cy(LLFFF) (SEQ ID NO:5). An additional sandwich ELISA test conducted with MrkA protein at 250 nM in solutions of 10 and 100% mouse sera demonstrate that cy(LLFFF)+R6 (SEQ ID NO:16) binds MrkA protein in the context of sera (FIG. 4B inset), making this molecule attractive for in vivo translation.

AR-PCC Binding to Multidrug Resistant *Klebsiella pneumoniae* Surfaces

While cy(LLFFF) (SEQ ID NO:5) exhibits high affinity towards recombinant full-length MrkA protein in solution, the structure of MrkA is likely much different in native fimbriae, in which MrkA proteins oligomerize into a helix-like structure (55, 63). The affinity of cy(LLFFF) (SEQ ID NO:5) towards MrkA assembled into the fimbriae of *K. pneumoniae* was interrogated using whole-cell ELISAs (FIG. 5A). In this assay, bacteria are exposed to biotinylated PCC ligands, then SAv-horseradish peroxidase (SAv-HRP), and then developed to produce a colorometric signal that correlates with SAv-HRP binding.

Figure 9:
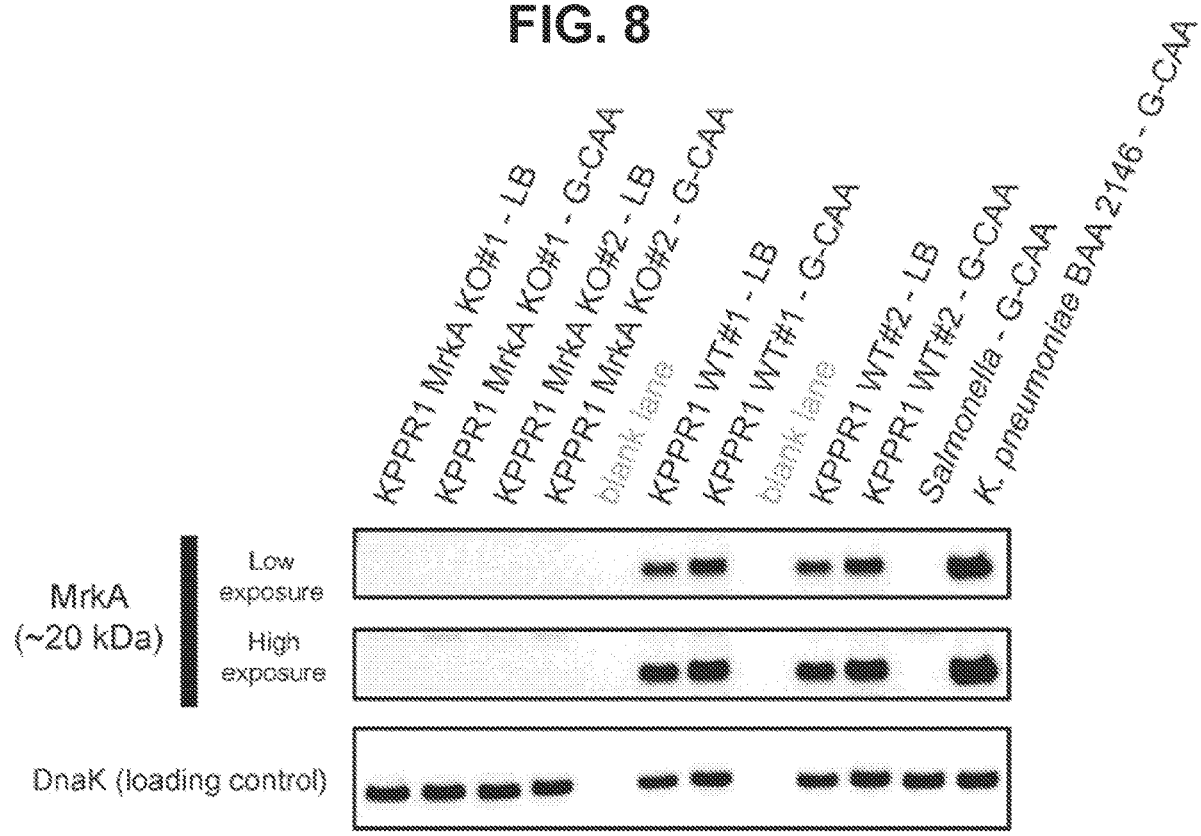
FIG. 9 is a Western blot to detect MrkA protein in wild type and MrkA/B/C knockout (KO) versions of *K. pneumoniae* strain ATCC 43816 ("KPPR1"), grown in either LB (LB) or Glycerol Casamino acid (G-CAA) media. KPPR1 MrkA KO grown in either LB or G-CAA media shows no detectable signal, confirming no MrkA expression. By comparison, wild type KPRRI cultured in either LB or G-CAA yields strong signals that establish high MrkA expression under either growth condition. A negative control of *Salmonella*, which does not express MrkA, does not show any signal, while a positive control of *K. pneumoniae* strain BAA2146 cultured in G-CAA shows a strong signal.

Whole-cell ELISA assays were conducted on the wild type version of the clinically-relevant strain of *K. pneumoniae*, KPPR1 (ATCC 43816). Wild type KPPR1 cells were cultured in G-CAA media to promote fimbrial expression (54), and MrkA expression in KPPR1 was confirmed by a western blot (FIG. 5B inset, full blot in FIG. 9). The ELISA results in FIG. 5B (solid orange bars) show strong signals from wild type KPPR1 cells exposed to cy(LLFFF) (SEQ ID NO:5) at concentrations ranging from 5 μM down to 5 nM. By comparison, KPPR1 cells treated with a control compound cy(LLFFA) (SEQ ID NO:11), which differs from cy(LLFFF) (SEQ ID NO:5) by a single phenyl moiety, produce much lower intensities (FIG. 5B, solid blue bars) that are comparable to those of untreated KPPR1 cells ("No PCC", FIG. 5B). These data not only demonstrate that cy(LLFFF) (SEQ ID NO:5) binds MrkA-expressing cells, but also reveal a high sensitivity of cy(LLFFF) (SEQ ID NO:5) structure on cell binding, establishing a strong structure-activity relationship for this PCC.

Figure 10:
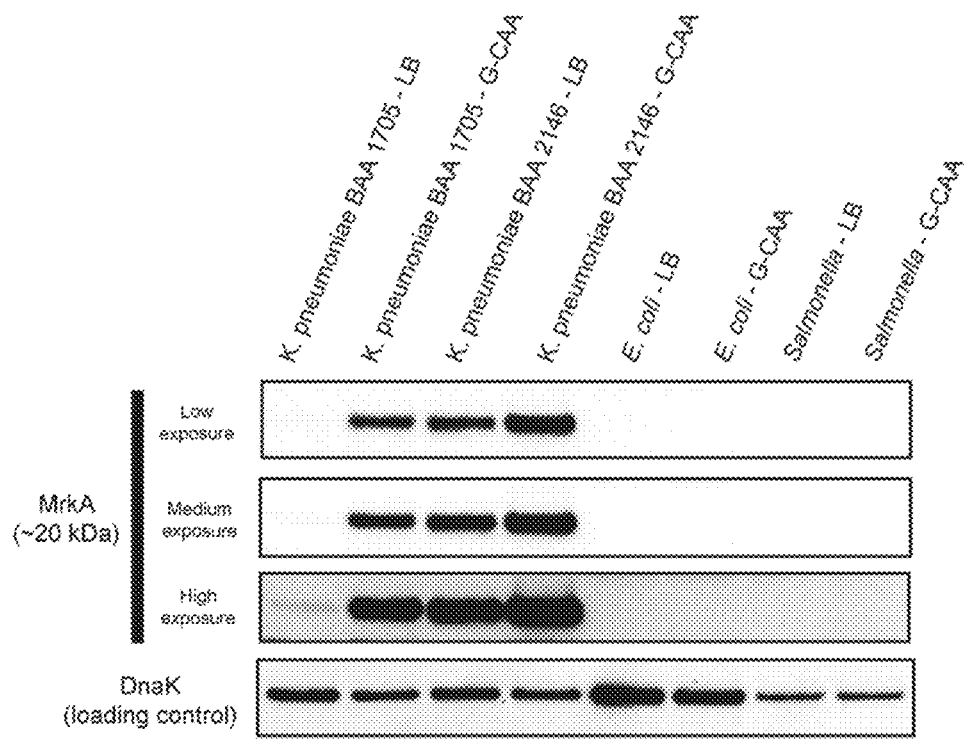
FIG. 10 is a Western blot to detect MrkA protein in *Klebsiella pneumoniae*, *Escherichia coli* and *Salmonella typhimurium* grown in either LB (LB) or Glycerol Casamino acid (G-CAA) solutions. *K. pneumoniae* BAA1705 grown in LB shows very faint signals associated with MrkA protein, while substantially higher signals associated with MrkA are observed for the same cells grown in NG-CAA. MrkA was highly expressed in *K. pneumoniae* BAA 2146 in either LB or GCAA. No detectable MrkA was observed in either *E. coli* or *S. typhimurium* under any growth conditions tested.
Figure 11A:
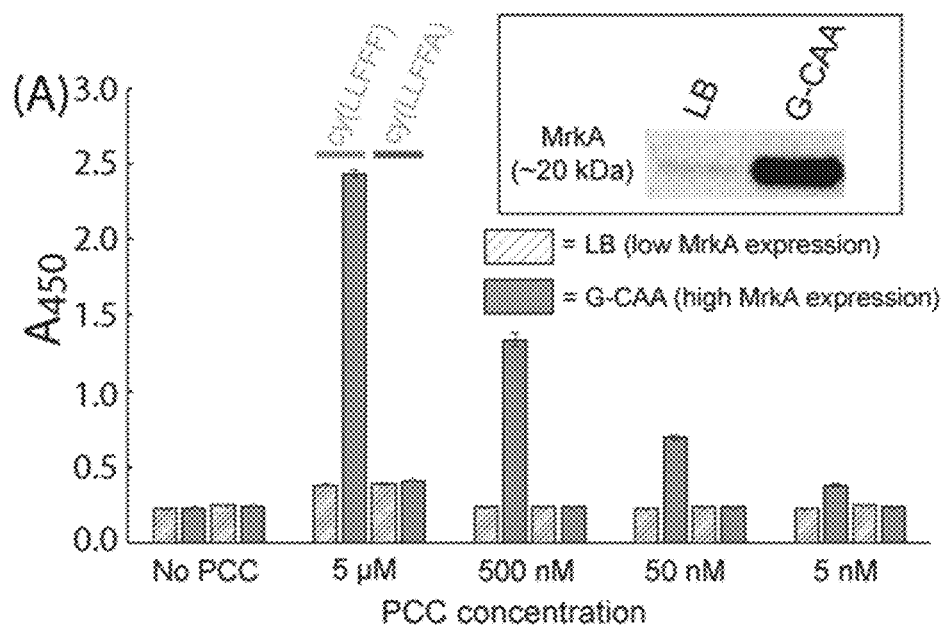
FIGS. 11A and 11B are plots of 450 nm absorbance from whole-cell ELISAs conducted on *K. pneumoniae* (strain ATCC BA with biotinylated cy(LLFFF) (SEQ ID NO: 5) and cy(LLFFA) (SEQ ID NO:11) PCCs at various concentrations. The inset in FIG. 11A shows cropped western blot lanes (full western blot in FIG. 10) that establish low MrkA expression for bacteria grown in LB and high levels for bacteria cultured in G-CAA media. Samples that were not treated with biotinylated PCCs, but with secondary antibody, establish a background absorbance (leftmost bars, "No PCC").
Figure 11B:
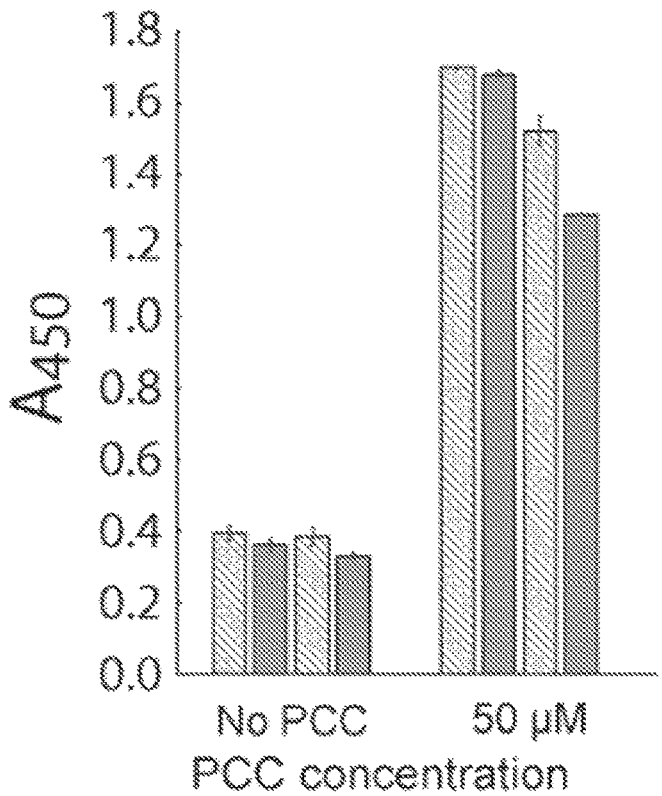

The specificity of cy(LLFFF) (SEQ ID NO:5) towards MrkA in particular was further interrogated by affinity tests to KPPR1 cells in which the gene encoding MrkA was knocked out (along with mrkB and mrkC) (64). Western blot analysis confirmed that this modified KPPR1 strain does not produce MrkA (FIG. 5B inset, full blot in FIG. 9). Knockout KPPR1 cells treated with cy(LLFFF) (SEQ ID NO:5) and control cy(LLFFA) (SEQ ID NO:11) yielded ELISA intensities comparable to baseline (FIG. 5B, dashed lines). This clearly establishes that cy(LLFFF) (SEQ ID NO:5) binds MrkA on K. pneumoniae cells, as would be expected for an epitope-targeted ligand. The specificity of cy(LLFFF) (SEQ ID NO:5) towards MrkA is further borne out by separate whole-cell ELISAs performed with K. pneumoniae cells (strain BAA 1705) cultured in G-CAA media, which elicits high MrkA expression, or LB media, which yields almost undetectable quantities of MrkA (FIGS. 10 and 11). ELISA signals were only observed for K. pneumoniae cells (strain BAA 1705) cultured in G-CAA (FIG. 11A), when treated with PCCs at concentrations of 5 μM or lower. However, when higher 50 μM PCC concentrations were used, both cy(LLFFF) (SEQ ID NO:5) and control cy(LLFFA) (SEQ ID NO:11) bound K. pneumoniae cells regardless of MrkA-expression level (FIG. 11B), suggesting non-selective hydrophobic binding at this high concentration.

The MrkA-specific binding of cy(LLFFF) (SEQ ID NO:5) anticipates selectivity towards MrkA-expressing K. pneumoniae versus bacteria devoid of MrkA. To test this, whole-cell ELISAs were performed on MrkA-producing multi-drug-resistant K. pneumoniae (strains BAA 1705 & 2146) and the bacteria Escherichia Coli (E. coli) and Salmonella typhiumurium (S. thyphimurium) that do not express MrkA, as confirmed by Western blot (FIG. 10). Whole-cell ELISA data in FIG. 5C show strong signal from the two strains of K. pneumoniae (BAA 1705 and BAA 2146) but only weak signals from Escherichia coli (E. coli) or Salmonella typhimurium (S. typhimurium) cells. The same bacterial strains treated instead with the control compound biotinylated cy(LLFFA) (SEQ ID NO:11) produced low signals that were comparable to secondary antibody controls ("No PCC", FIG. 5C), establishing low binding. Strong binding of cy(LLFFF) (SEQ ID NO:5) towards K. pneumoniae cells demonstrate the excellent binding selectivity of cy(LLFFF) (SEQ ID NO:5) towards MrkA-expressing K. pneumoniae cells versus non-target bacteria. The compound cy(LLFFF)+R6 (SEQ ID NO:16), which was chemically optimized for increased hydrophilicity versus cy(LLFFF) (SEQ ID NO:5), exhibited similarly high selectivity towards MrkA-expressing cells (FIG. 5C). Importantly, though not explicitly tested here, E. coli and S. typhimurium are known to express fimbria under growth conditions similar to those used here (65, 66), suggesting selectivity of cy(LLFFF) (SEQ ID NO:5) to type 3 fimbriae of K. pneumoniae. Moreover, salt aggregation tests reveal that the cell surfaces of the K. pneumoniae strains used here have similar or lower hydrophobicities than E. coli or S. typhimurium, indicating that binding selectivity cannot be explained simply by hydrophobicity. In these tests, droplets of phosphate buffered solution containing live bacteria or heat-killed bacteria and various concentrations of $(NH_4)_2SO_4$ at 10 m or 30 m following mixing were imaged. Aggregation in each droplet was assessed by visual inspection and scored as indicating non-aggregated, low levels of aggregation, or extensive aggregation. All droplets were on a single glass slide and image acquisition of all droplets took less than a minute for each 10 m and 30 m time point. Crystallization was observed at 30 m times that precluded assessment of aggregation. These results show that K. pneumoniae strains aggregate at similar or higher salt concentrations than E. coli and S. typhimurium, indicating similar or lower cell surface hydrophobicity for these strains of K. pneumoniae versus E. coli and S. typhimurium.

AR-PCC-Driven Opsonization of K. pneumoniae

Next, cy(LLFFF) (SEQ ID NO:5) was used to promote opsonization by appending an antibody-recruiting (AR) handle, the hapten 2,4-dinitrophenyl (DNP), to form an AR-PCC. DNP is an agonist for 1% of endogenous human antibodies (67), and has been employed in several immune-recruiting therapeutics to recruit antibodies to various pathogens (26, 39, 40) and cancer cells (68, 69). It was realized that once the AR-PCC binds to the K. pneumoniae surface, the AR handle should recruit antibodies to the pathogen. PCCs were tagged with a DNP group via conjugation of a DNP-modified lysine residue, in which a DNP moiety is covalently attached at the terminal sidechain amine. Both DNP-conjugated cy(LLFFF) (SEQ ID NO:5) and cy(HNGPT) (SEQ ID NO:18) PCCs showed absorbances at 360 nm and 420 nm that are characteristic of DNP-modified lysine (40) and indicate successful labeling of the PCC.

Figure 6:
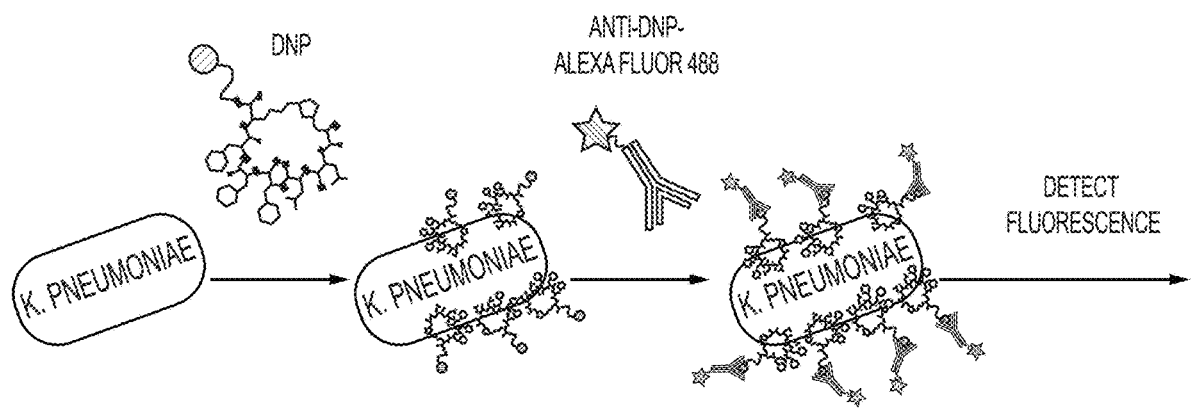
FIG. 6 is a schematic of a flow cytometry assay to evaluate the capacity of EPIs (AR-PCCs) to recruit antibodies to *K. pneumoniae* cell surfaces. In the assay, *K. pneumoniae* is incubated with EPIs (AR-PCCs) that bear DNP groups, exposed to fluorescent anti-DNP antibodies, and then subjected to flow cytometry.
Figure 12:
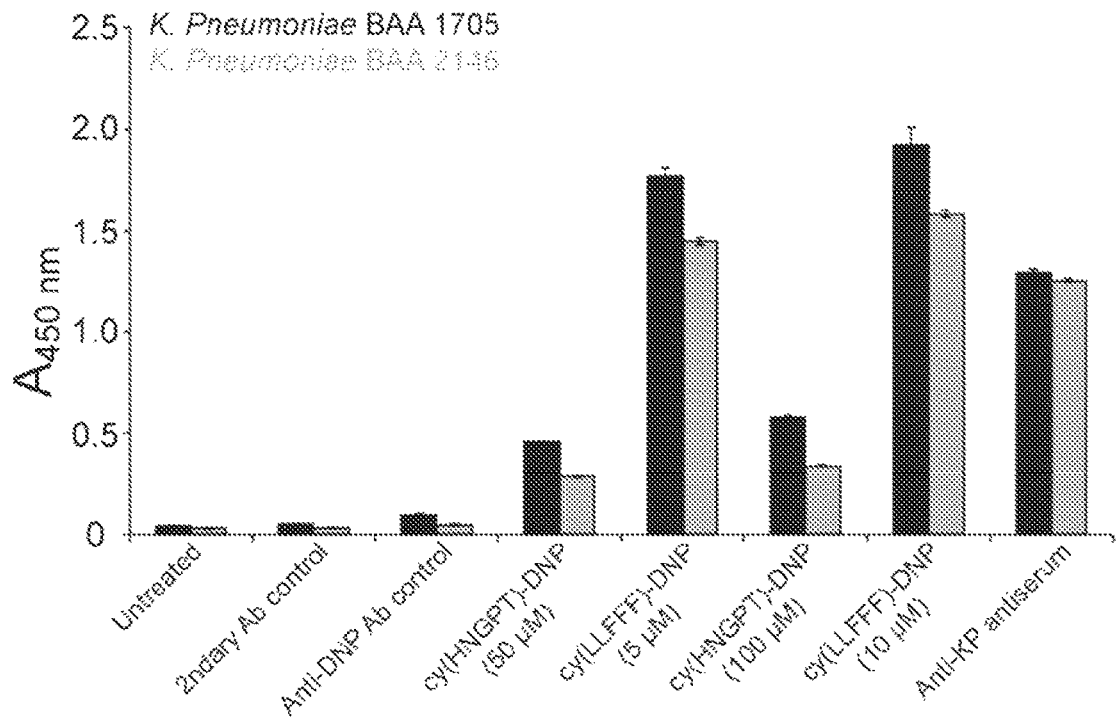
FIG. 12 is a plot of 450 nm absorbances obtained from a cell-based ELISA assay conducted on two strains of *K. pneumoniae* cells, BAA 1705 (black) and BAA 2146 (orange), that were either untreated or opsonized by EPIs (AR-PCCs) and/or antibodies. Very low absorbances were observed for *K. pneumoniae* cells that were untreated, or treated either with secondary antibody or anti-DNP controls. By comparison, much larger signal is observed for *K. pneumoniae* opsonized with cy(LLFFF) (SEQ ID NO:5) plus anti-DNP at either 5 μM or 10 μM EPI (AR-PCC) concentrations (anti-DNP concentration fixed). This establishes EPI-driven opsonization by cy(LLFFF)-DNP (SEQ ID NO:5). Much smaller signals were observed from *K. pneumoniae* cells opsonized with a dummy EPI (AR-PCC) ligand cy(HNGPT)-DNP (SEQ ID NO:18) at a much greater concentrations of 50 and 100 μM. This indicates opsonization by cy(LLFFF)-DNP (SEQ ID NO: 5) is specific and is driven by the ligand cy(LLFFF) (SEQ ID NO:5), rather than the Lys (DNP) moiety.

Flow cytometry was used to determine the extent to which cy(LLFFF)-DNP conjugates (SEQ ID NO:5) promote the opsonization of resistant K. pneumoniae by anti-DNP antibodies. K. pneumoniae cells (strain BAA 2146) were first treated with cy(LLFFF)-DNP (SEQ ID NO:5) and then Alexafluor 488 fluorophore-labeled anti-DNP antibodies (FIG. 6), so fluorescence served as a proxy for opsonization. Cells exposed to cy(LLFFF)-DNP (SEQ ID NO:5), at either 1 or 5 μM concentrations, plus secondary antibody showed much higher fluorescence than cells incubated with 50 μM of the control cy(HGNPT)-DNP conjugate (SEQ ID NO:18) plus secondary antibody and secondary antibody only. Untreated cells showed the lowest fluorescence. Cytometry measurements were gated for single cells, and each distribution comprises >18,000 cells. The cytometry data show weak fluorescence (predominantly <$0.2 \times 10^1$ intensity) K. pneumoniae cells that were either unstained or incubated with fluorescent anti-DNP only, and slightly higher fluorescence (predominantly <$1.0 \times 10^1$ intensity) was observed for cells exposed to control AR-PCC cy(HNGPT)-DNP (SEQ ID NO:18) at 50 μM plus anti-DNP, indicating slight cross-reactivity. Fluorescence counts for all these samples, however, are substantially less than for cells treated with much lower concentrations (1 or 5 μM) of cy(LLFFF)-DNP (SEQ ID NO:5) plus fluorescent anti-DNP. This demonstrates that cy(LLFFF)-DNP (SEQ ID NO:5) promotes the opsonization of K. pneumoniae cells with anti-DNP. The same behaviors were observed on a separate resistant K. pneumoniae strain, BAA 1705 (data not shown) and by using whole-cell ELISA methods that were sensitive to anti-DNP binding (FIG. 12). Paired with the recruitment of SAv-HRP to cells by biotin-cy(LLFFF) (SEQ ID NO:5) (FIG. 5B), these results demonstrate the versatility of AR-PCCs to recruit diverse and specified biomolecules to bacterial surfaces.

AR-PCC-Driven Phagocytosis and Opsonophagocytic Killing (OPK) of K. pneumoniae

Figure 7A:
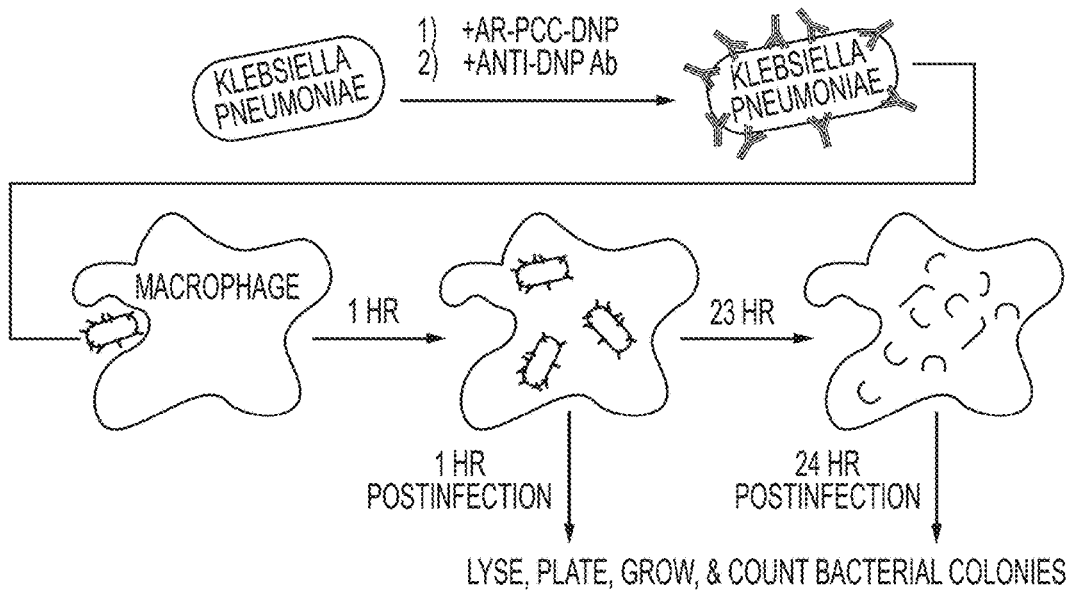
FIGS. 7A and 7B show a gentamicin protection assay that evaluates EPI-driven phagocytosis and opsonophagocytic killing (OPK) of *K. pneumoniae* cells by murine bone-marrow-derived macrophages.
Figure 13:
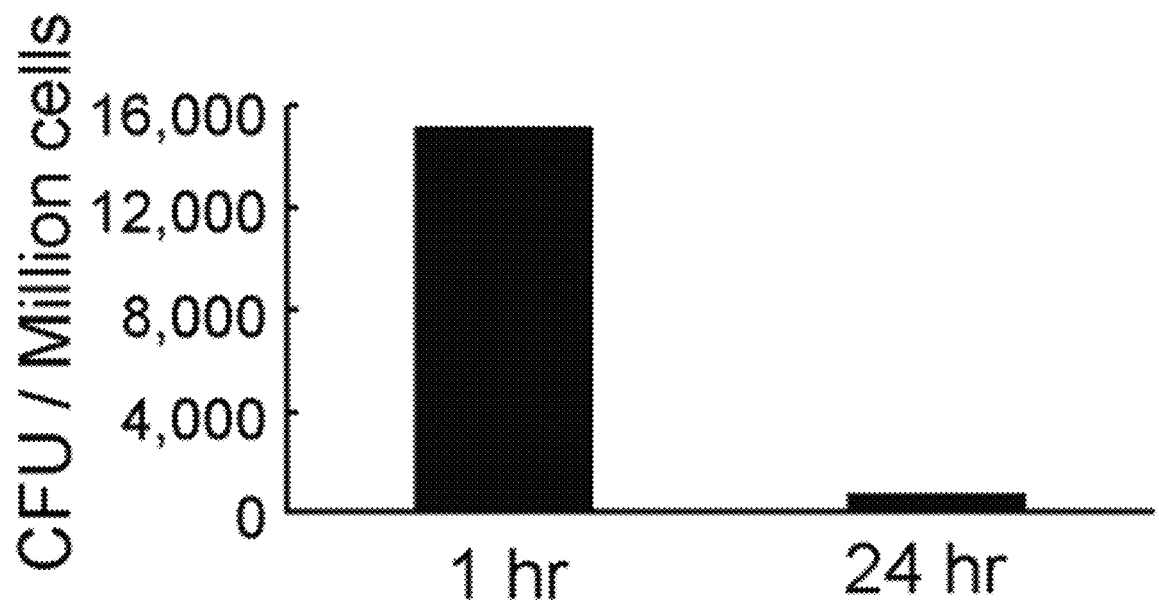
FIG. 13 is a plot of CFU counts per million cells obtained by plating and growing macrophage lysate after exposure of macrophages to *K. pneumoniae* bacteria for either 1 or 24 h. Larger cell counts (~15,000 CFU) were observed in samples prepared from macrophages harvested at 1 h, while very low counts (~1,000 CFU) were detected in samples from macrophages harvested at 24 h. This demonstrates that after 2 h, bacteria remain viable inside the phagosome, while after 24 h most bacteria were rendered inviable.

Given that cy(LLFFF)-DNP (SEQ ID NO:5) recruits antibodies to K. pneumoniae surfaces, it was expected that K. pneumoniae opsonized in this manner would be more susceptible to phagocytosis by macrophages. AR-PCC-driven phagocytosis and OPK were quantified by a gentamicin protection assay, as depicted in FIG. 7A. For this assay, K. pneumoniae cells (strain BAA 1705) were treated with cy(LLFFF)-DNP (SEQ ID NO:5), opsonized by anti-DNP antibodies, and then incubated with murine bone-marrow-derived macrophages (BMDMs). BMDMs were subsequently exposed to a solution containing gentamicin, to which *K. pneumoniae* strain BAA 1705 is susceptible, to kill any extracellular bacteria. Phagocytosed bacteria remain viable inside BMDMs for at least 1 h, yet are rendered inviable after 24 h by OPK (FIG. 13). Macrophages harvested at 1 h and 24 h were lysed and plated to generate bacterial colonies, which were enumerated to quantify phagocytosis and OPK.

Figure 7B:
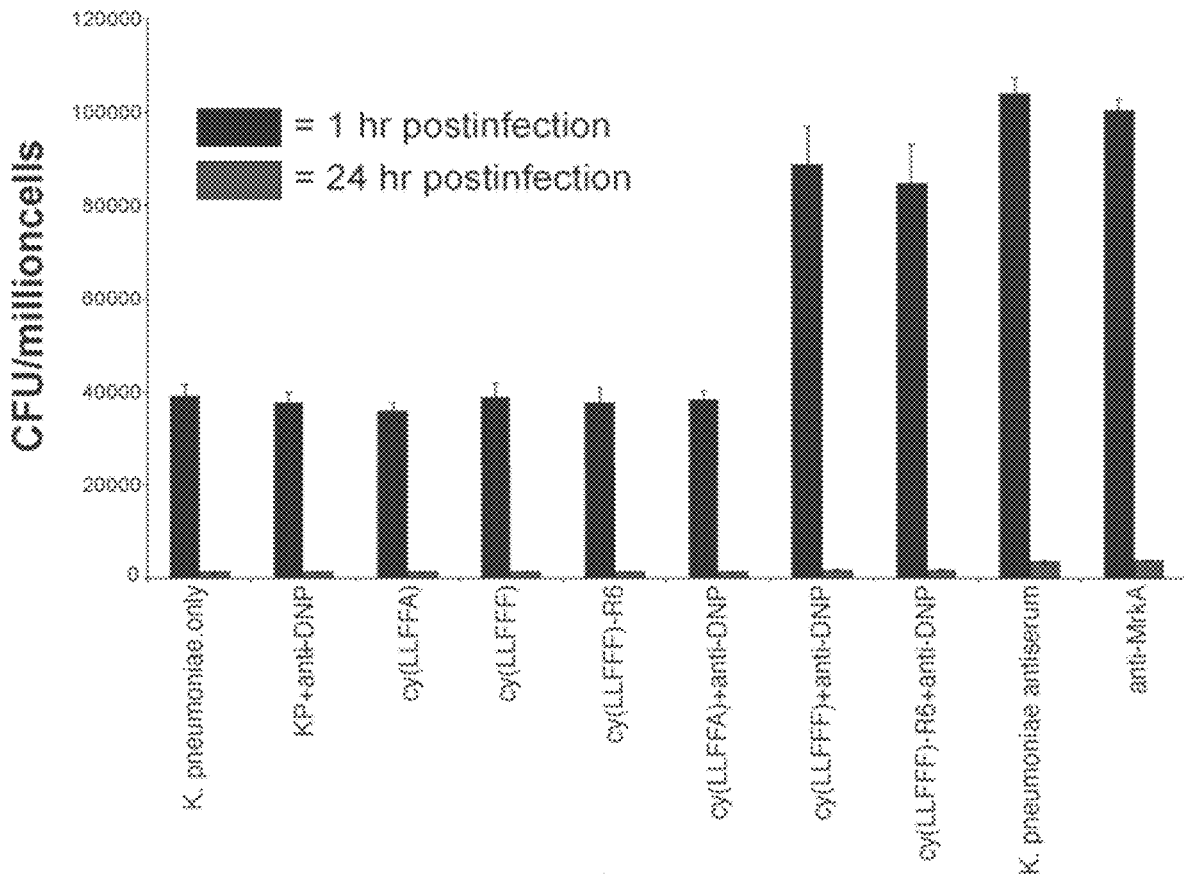

Phagocytosis assays were carried out using cy(LLFFF)-DNP (SEQ ID NO:5) on a strain of *K. pneumoniae* (BAA 1705) that harbored high antimicrobial resistance, including all tested carbapenems, but is susceptible to gentamicin. As shown in FIG. 7B, BMDMs exposed to untreated *K. pneumoniae* cells for 1 h yielded counts of ~39,000 CFU/million cells, establishing basal levels of phagocytosis (dashed line in FIG. 7B). Similar signals were also observed in all control samples (FIG. 7B, leftmost six samples) harvested at the 1 h time point. The controls were untreated bacteria ("*K. pneumoniae* only") or bacteria treated either with anti-DNP antibody only, cy(LLFFF)-DNP (SEQ ID NO:5) only, cy(LLFFA)-DNP (SEQ ID NO:11) only, cy(LLFFF)+R6-DNP (SEQ ID NO:16) only, or cy(LLFFA)-DNP (SEQ ID NO:11) plus anti-DNP. None of these treatments elicited phagocytosis above basal levels. Much greater counts of 89,000 CFU (seventh and eighth 1 h bars, FIG. 7B) were observed from samples in which *K. pneumoniae* was treated with cy(LLFFF)-DNP (SEQ ID NO:5) plus anti-DNP, which compared well with the OPK-promoting performances of the *K. pneumoniae* antiserum and the anti-MrkA antibody (FIG. 7B, rightmost two samples). When tagged with DNP, the optimized compound cy(LLFFF)+R6 (SEQ ID NO:16) also enhanced phagocytosis, as shown by comparing heights of the seventh and eighth 1 h bars in FIG. 7B. In fact, the OPK activity of DNP-tagged cy(LLFFF)-R6 (SEQ ID NO:16) was comparable to that of cy(LLFFF)-DNP (SEQ ID NO:5). Statistical analyses (T-tests comparing phagocytosed CFUs after one hour of treatment) indicated that cy(LLFFF)-DNP (SEQ ID NO:5) plus anti-DNP promoted phagocytosis of *K. pneumoniae* above the basal level of the controls (p-value <0.001, FIG. 5 and Table 4). Table 4 shows the results of a T-test conducted of the colony forming units (CFU) counts between all samples in this dataset. Ranges for P-values are indicated by different numbers (see legend), with lower numbers associated with lower P-values. For example, in the 1 h post-infection heatmap, intersection of cy(LLFFF)-R6-anti-DNP on the x-axis and cy(LLFFF)-R6 is "3," indicating a P-value of 0.001-0.01, illustrating that the difference between the CFU counts for these samples is statistically significant.

TABLE 4

Statistical significance of colony forming units between samples.

| 1 = 0 to 0.0001<br>2 = 0.0001 to 0.001<br>3 = 0.001 to 0.01<br>4 = 0.01 to 0.05<br>5 = 0.05 to 0.1<br>6 = 0.1 to 1 | *K. pneumonia* only | KP + anti-DNP | cy(LLFFA) (SEQ ID NO: 11) | cy(LLFFF) (SEQ ID NO: 5) | cy(LLFFF)-R6 (SEQ ID NO: 16) | cy(LLFFA) + anti-DNP (SEQ ID NO: 11) |
|---|---|---|---|---|---|---|
| 1 hour post-infection | | | | | | |
| *K. pneumonia* only | 6 | 6 | 6 | 6 | 6 | 6 |
| KP + anti-DNP | 6 | 6 | 6 | 6 | 6 | 6 |
| cy(LLFFA) (SEQ ID NO: 11) | 6 | 6 | 6 | 6 | 6 | 6 |
| cy(LLFFF) (SEQ ID NO: 5) | 6 | 6 | 6 | 6 | 6 | 6 |
| cy(LLFFF)-R6 (SEQ ID NO: 16) | 6 | 6 | 6 | 6 | 6 | 6 |
| cy(LLFFA) + anti-DNP (SEQ ID NO: 11) | 6 | 6 | 6 | 6 | 6 | 6 |
| cy(LLFFF) + anti-DNP (SEQ ID NO: 5) | 3 | 3 | 3 | 3 | 3 | 3 |
| cy(LLFFF)-R6 + anti-DNP (SEQ ID NO: 16) | 3 | 3 | 3 | 3 | 3 | 3 |
| *K. pneumonia* antiserum | 1 | 1 | 1 | 1 | 1 | 1 |
| anti-MrkA | 1 | 1 | 1 | 1 | 1 | 1 |
| 24 hours post-infection | | | | | | |
| *K. pneumonia* only | 6 | 6 | 6 | 6 | 6 | 6 |
| KP + anti-DNP | 6 | 6 | 6 | 6 | 6 | 6 |
| cy(LLFFA) (SEQ ID NO: 11) | 6 | 6 | 6 | 6 | 6 | 6 |
| cy(LLFFF) (SEQ ID NO: 5) | 6 | 6 | 5 | 6 | 6 | 6 |
| cy(LLFFF)-R6 (SEQ ID NO: 16) | 6 | 6 | 6 | 6 | 6 | 6 |
| cy(LLFFA) + anti-DNP (SEQ ID NO: 11) | 6 | 6 | 6 | 6 | 6 | 6 |
| cy(LLFFF) + anti-DNP (SEQ ID NO: 5) | 4 | 3 | 2 | 3 | 3 | 3 |
| cy(LLFFF)-R6 + anti-DNP (SEQ ID NO: 16) | 4 | 3 | 3 | 3 | 3 | 3 |
| *K. pneumonia* antiserum | 3 | 3 | 3 | 3 | 3 | 3 |
| anti-MrkA | 1 | 1 | 2 | 1 | 1 | 1 |

| 1 = 0 to 0.0001<br>2 = 0.0001 to 0.001<br>3 = 0.001 to 0.01<br>4 = 0.01 to 0.05<br>5 = 0.05 to 0.1<br>6 = 0.1 to 1 | cy(LLFFF) + anti-DNP (SEQ ID NO: 5) | cy(LLFFF)-R6 + anti-DNP (SEQ ID NO: 16) | *K. pneumonia* antiserum | anti-MrkA |
|---|---|---|---|---|
| 1 hour post-infection | | | | |
| *K. pneumonia* only | 3 | 3 | 1 | 1 |
| KP + anti-DNP | 3 | 3 | 1 | 1 |

TABLE 4-continued

Statistical significance of colony forming units between samples.

| | | | | |
|---|---|---|---|---|
| cy(LLFFA) (SEQ ID NO: 11) | 3 | 3 | 1 | 1 |
| cy(LLFFF) (SEQ ID NO: 5) | 3 | 3 | 1 | 1 |
| cy(LLFFF)-R6 (SEQ ID NO: 16) | 3 | 3 | 1 | 1 |
| cy(LLFFA) + anti-DNP (SEQ ID NO: 11) | 3 | 3 | 1 | 1 |
| cy(LLFFF) + anti-DNP (SEQ ID NO: 5) | 6 | 6 | 5 | 6 |
| cy(LLFFF)-R6 + anti-DNP (SEQ ID NO: 16) | 6 | 6 | 4 | 5 |
| *K. pneumonia* antiserum | 5 | 4 | 6 | 6 |
| anti-MrkA | 6 | 5 | 6 | 6 |
| 24 hours post-infection | | | | |
| *K. pneumonia* only | 4 | 4 | 3 | 1 |
| KP + anti-DNP | 3 | 3 | 3 | 1 |
| cy(LLFFA) (SEQ ID NO: 11) | 2 | 3 | 3 | 2 |
| cy(LLFFF) (SEQ ID NO: 5) | 3 | 3 | 3 | 1 |
| cy(LLFFF)-R6 (SEQ ID NO: 16) | 3 | 3 | 3 | 1 |
| cy(LLFFA) + anti-DNP (SEQ ID NO: 11) | 3 | 3 | 3 | 1 |
| cy(LLFFF) + anti-DNP (SEQ ID NO: 5) | 6 | 6 | 4 | 2 |
| cy(LLFFF)-R6 + anti-DNP (SEQ ID NO: 16) | 6 | 6 | 4 | 2 |
| *K. pneumonia* antiserum | 4 | 4 | 6 | 6 |
| anti-MrkA | 2 | 2 | 6 | 6 |

Nonetheless, the level of phagocytosis induced by cy(LLFFF)-DNP plus anti-DNP was about 15% lower than that induced by *K. pneumoniae* antiserum and anti-MrkA treatment (positive controls: p<0.001). At 24 h of incubation, the cy(LLFFF) plus anti-DNP sample (and all other samples) showed little to no cell counts, indicating near complete OPK. Thus, AR-PCCs demonstrably enhance the OPK of a highly resistant *K. pneumoniae* bacterium, presumably by engaging Fc-receptor-mediated phagocytosis pathways.

Conclusions

Demonstrated in this example is a new concept for targeted antibiotics called antibody-recruiting protein-catalyzed capture agents (AR-PCCs). AR-PCCs were designed to exhibit specific in vitro antimicrobial activities against highly-resistant *Klebsiella pneumoniae* bacteria. AR-PCC molecules comprise of two molecular motifs: a peptide ligand that binds a specific surface protein epitope on the pathogen, and a hapten that recruits antibodies. Combined multi-omic data and bioinformatic analyses provided an algorithm for selecting a highly abundant surface protein and epitopes on *K. pneumoniae* as targets for AR-PCCs. A single-generation PCC combinatorial screen was then used to rapidly identify macrocyclic peptide ligands to the chosen epitope targets. The lead AR-PCC ligand, cy(LLFFF) (SEQ ID NO:5), exhibited strong binding to full-length MrkA ($EC_{50}$=50 nM) and one of the highly conserved target epitopes, as well as high specificity towards MrkA-expressing *K. pneumoniae* versus other bacterial species that do not express MrkA. Further, the lead AR-PCC ligand conjugated with 2,4-dinitrophenyl (DNP) moieties recruited anti-DNP antibodies to *K. pneumoniae* surface, which led to increased levels of phagocytosis by macrophages and ultimately greater opsonophagocytic killing. Chemical modifications to the cy(LLFFF) (SEQ ID NO:5) showed that the macrocycle scaffold can be optimized for desired in vivo pharmacokinetic (PK) characteristics. While *K. pneumoniae* served as the target in this study, the approaches used here are adaptable to other antibiotic resistant extracellular pathogens, including viruses. This versatility also makes feasible the development of cocktails of AR-PCCs that simultaneously target several conserved surface epitopes on a single pathogen, to facilitate complete clearance of bacterial populations that exhibit heterogenous surface protein expression. Overall, AR-PCCs are an advanced and all-synthetic molecular platform that can be rapidly designed, built, and deployed against resistant microbes.

Materials and Methods

Gene Expression Analysis.

Transcriptional profiles (normalized read counts) of *Klebsiella pneumoniae* strain CH1034 in stationary phase, exponential phase, and biofilms (7 h, 13 h and detached cells) generated by Guilhen and collaborator (46) were downloaded from the GEO database (accession number: GSE71754) (70). The downloaded dataset included 5,146 genes and triplicates for each condition. Although additional transcriptomes are publicly available for *K. pneumoniae*, the analysis was restricted to a single dataset (with key stages of *K. pneumoniae* life cycle) due to: (i) the high number of *K. pneumoniae* strains studied by different research groups. This means available transcriptomic data involve multiple strains and have been collected on multiple platforms. (ii) the large size of *K. pneumoniae* pangenome (51) makes possible transcript levels of any given gene may be present in only some of the available transcriptional profiles. Inspired by the superior performance of rank-combined predictions that integrate multiple network inference methods/predictions (with respect to single ones) (71, 72), all genes in each replicate were ranked based on their normalized read counts. Then, the average ranking position of each gene along the 15 replicates was computed. This approach identified genes with consistently high transcript levels along the sampled conditions and, for downstream analyses, focus was placed on the set of genes that were in the top 10% of the ranking (515 genes).

Identification of Highly Expressed Genes Encoding Outer Membrane or Extracellular Proteins.

Available literature was mined to identify *K. pneumoniae* proteins that localize in the outer membrane or extracellular space (47-49). 54 proteins were found that localize to the regions of interest. Then, the overlap was evaluated between this set of proteins and the group of 515 highly expressed genes defined in the "Gene Expression Analysis" section. To compare the two sets, the genome annotation of *Klebsiella pneumoniae* strain CH1034 was first downloaded from the NCBI website in May 2018. The genome annotation was used to convert the locus names used as gene ID in the analyzed transcriptomics data to standard gene names (e.g., CH1034_10002 corresponds to phnV). Finally, available information (54, 56, 73-80) about genes present in both sets was manually reviewed to select a target, prioritizing gene targets that yielded virulence-associated proteins that were either membrane-spanning or oriented on the extracellular side of the outer membrane.

MrkA Sequence Alignment.

A Blastn (megablast) was first performed in the NCBI BLAST website using as query the nucleotide sequence of mrkA in the *K. pneumoniae* ATCC BAA-1705 strain. The search was restricted to the *K. pneumoniae* taxa and set the maximum number of allowed target sequences to 500. Other parameters were kept as default. All hits (402) were downloaded. Then, any hit from plasmid sequences or duplicated sequences were removed. Nucleotide hit sequences were then translated using EMBOSS Transeq (60). Finally, MrkA protein sequences were aligned using MAFFT and visualized in Jalview (60, 61).

Bioinformatics Analysis.

Predictions for surface exposure and surface antigenicity were performed using NetsurfP 2.0 (57) and Bepipred2.0 (58) software (using default parameters), with the primary sequence of MrkA as an input, which assign either a value of 1 or 0 to each residue. The resulting prediction values were then averaged over 14-residue epitopes, converted to a percent value, and plotted. The uniqueness of each 14-residue epitope of MrkA among all epitopes in the human proteome was determined by performing a BlastP2.0 search with the parameters defined in the heuristic string method by Berglund et al. (59). Many matches were obtained for each epitope, and the match with greatest homology with the MrkA epitope was extracted, the corresponding homology converted to a percent value, and plotted as "maximum homology." All results from these bioinformatics analyses are tabulated in Table 1.

Peptide Synthesis and Purification.

All peptides were synthesized by using standard Fmoc solid-phase peptide synthesis procedures, using either Rink Amide resin (Aapptech, RRZ005), Sieber Amide resin (Aapptech, RST001), or Tentagel S NH2 resin (Rapp Polymere, S30902). N-methylpyrrolidone (NMP, Alfa Aesar, 43894) was used as a solvent for all synthesis procedures, except the coupling of biotin (AK Scientific, C820) which used a 50/50 mixture of dimethylsulfoxide (DMSO, Fisher, D128-4) and NMP for solubility. All standard Fmoc-protected amino acids were purchased from ChemPep. Fmoc deprotection was achieved with 20% piperidine (Alfa Aesar, A12442) in NMP, and coupling reactions employed O-(7-Azabenzotriazol-1-yl)-N,N,N',N'-tetramethyluronium hexafluorophosphate (HATU, Chem-Impex Int'l Inc., 12881) as an activator and N-diisopropylethylamine (DIEA, Alfa Aesar, A11801) as the base. An Aapptech Titan 357 instrument was used to couple all Fmoc-protected standard amino acids and non-natural residues with click handles, i.e., propargylglycine (Pra, ChemPep, 180710) and azidolysine (Az4, ChemPep, 101227). Fmoc-NH-peg5-$CH_2CH_2OH$ (ChemPep, 280110), Fmoc-NH-peg10-$CH_2CH_2OH$ (ChemPep, 280113), and Fmoc-Lys(DNP)-OH (ApexBio, A7926) were coupled overnight with molar excesses of 2, 2, and 6 for the Fmoc-protected compound, HATU, and DIEA, respectively (excesses with respect to the reactive groups on bead surface). The Cu-catalyzed azide-alkyne click reaction was conducted by incubating beads overnight with shaking in a solution of 1.5× molar excess of Cu(I) (Millipore Sigma, 818311) and 5× molar excess of L-ascorbic acid (Sigma, A0278) in 20% piperidine in NMP (excesses with respect to the reactive groups on resin surface). The resin was then washed 5×1 minute with 5-8 mL of NMP, after which extra copper was removed by incubating beads with shaking for 5 minutes in a solution of 5 w/v % DIEA, 5 v/v % Sodium diethyldithiocarbamate trihydrate (Chem-Impex) in NMP. The resin is washed extensively with NMP (3× without shaking, 5×5 min or more with shaking) until the bead color turned white to light yellow and remained constant. After synthesis was complete, the resin was dried in dichloromethane (DCM, Acros Organics, 40692-0040) for at least 15 mins on a vacuum manifold. Peptides were cleaved from dried resin by mixing with 10 mL solution of Trifluoroacetic acid (TFA, Alfa Aesar, L06374):Triethylsilane (TES, Millipore Sigma, 230197) Millipore Water ($H_2O$) at volumetric ratios of 95:2.5:2.5, respectively, and vigorously stirring for 2 hr. Cleavage under these acidic conditions also removed all acid-labile sidechain protecting groups. The resulting solution was added to 40 mL of diethyl ether (Acros Organics, 615080-0040) and stored overnight at −20° C. to precipitate the peptide product. The product was then pelleted by centrifugation, dried in air, and then resuspended in an aqueous solution of 30% acetonitrile (Fisher, A955-4) (aq.) with 0.1% of either TFA or formic acid (Fisher, A117-50) before purification by liquid-chromatography-mass spectrometry.

PCC compounds were purified on a Waters Autopurification system, which isolated compounds based on MS peaks corresponding to protonated $[M+1H]^+$ and $[M+2H]^{2+}$, and/or sodium adducts $[M+Na]^+$ and $[M+2Na]^{2+}$. The isocratic points of PCCs were determined based on the elution of the compound from a C18 prep-scale column. Synthetic epitopes were either purified on the Waters Autopurification System, or by semi-preparative HPLC and then using matrix-assisted laser desorption/ionization mass spectroscopy to identify fractions with the desired m/z ratio. The resulting peptides were lyophilized, the yield determined by mass difference or UV-visible absorbance, and resuspended at a concentration of up to 10 mM peptide in DMSO. Peptides were stored at −80° C. before thawing for each use.

Standard Fmoc-protected synthesis and split-and-mix procedures were used to synthesize a one-bead one-compound library on TentaGel S $NH_2$ beads with the structure $NH_2$—Pra(80%)/Gly(20%)-$X_1X_2X_3X_4X_5$-Az4-M-Resin, where $X_1$ indicates one of 16 natural amino acids (excluding Methionine, Cysteine, Glutamine and Isoleucine). The coupling solution for the N-terminal residue included 80% Fmoc-propargylglycine-OH and 20% Fmoc-glycine-OH. The resulting library was clicked under copper-catalyzed conditions as described above to yield on each bead ~80% of the cyclic product cy(Pra-$X_1X_2X_3X_4X_5$-Az4) and 20% of the linear product Gly-$X_1X_2X_3X_4X_5$-Az4, which facilitates identification by tandem mass spectroscopy. A final Pra was coupled onto the library to enable PCC combinatorial screening. The library was then incubated with a solution containing volumetric ratios of 95:2.5:2.5 of TFA:H$_2$O:TES under vigorous stirring for 2 h to remove acid-labile side-chain protecting groups, and the washed 3×5 min in H$_2$O, NMP, methanol (Fisher, A454-1), and then DCM.

Combinatorial PCC Screening.

Combinatorial in situ click screens were performed as described previously (44). Briefly, 500 mg (representing ~1.4 copies of approximately 1,000,000 different compounds) of a combinatorial one-bead one-compound libraries was incubated overnight with shaking in TBS buffer (25 mM Tris HCl, 150 mM NaCl, pH 7.6). A preclear to remove beads that bound SAv-AP was performed as follows. Unless otherwise noted, all steps were performed at room temperature and all incubation and washing steps were conducted with 4 mL of the stated solution with shaking. Beads were blocked overnight by incubation in blocking buffer (TBS buffer with 1% BSA and 0.05% Tween-20, pH 7.6), rinsed with blocking buffer 3×1 min, incubated for 1 h with 1:10,000 streptavidin-Alkaline phosphatase (SAv-AP) (Thermofisher Scientific, SA1008) in 5 mL of blocking buffer, and then washed with the following: 3×5 min in TBS, 3×5 min in 0.1M glycine (pH 2.8), 3×5 min in TBS buffer, 3×5 min of alkaline phosphatase (AP) buffer (100 mM Tris-HCl, 150 mM NaCl, 1 mM MgCl$_2$, pH 9.0). The beads were then split and transferred into two separate petri dishes by using AP buffer, such that there was a total of 16 mL of AP buffer per dish. Separately, 10 mL of BCIP/NBT development buffer was prepared from the Promega BCIP/NBT Color Development substrate kit (Promega, S3771) by adding 66 μL of the NBT solution to 10 mL of AP buffer, mixing by hand, then adding 33 μL of the BCIP solution followed by vortexing. Four mL of the BCIP/NBT development buffer was added to each plate and then each plate was gently swirled for 30 seconds to ensure the development buffer was well-mixed. The reaction was quenched after 25 minutes by adding 4 mL of 5.0N HCl (aq.) to each plate and swirling to homogenize. The beads were transferred to a new SPPS tube by using Millipore water and were then washed copiously with Millipore water (10× without shaking, then 10×1 minute with shaking). The beads were resuspended in 0.05 N HCl (aq.), returned to a petri dish, and the purple beads removed by using a 10 μL pipette.

After all of the purple beads were removed, the in situ click screen was performed with the MrkA SynEps. The library was collected and rinsed in TBS buffer (3×5 min), incubated with a TBS buffer containing 20 μM of each purified MrkA SynEp for 6 h. The library was then subjected to the following treatments: washed with TBS buffer (10×1 min), incubated for 1 h in 7.5 M Guanidine-Hydrochloride (pH 2.0), washed with TBS (10×1 min), incubated for 2 h with blocking buffer, washed with blocking buffer (3×1 min), and incubated for 1 h with 1:10,000 SAv-AP in 5 mL of blocking buffer. The library was then washed as follows: 3×5 min in TBS, 3×5 min in 0.1M glycine (pH 2.8), 3×5 min in TBS buffer, 3×5 min of AP buffer. The library was then split into two petri dishes and developed as described above. The reaction was quenched by the addition of 4 mL of 5.0N HCl (aq.), then the beads were transferred to a new SPPS tube, washed copiously with Millipore water (10× without shaking, then 10×1 minute with shaking), resuspended in 0.05N HCl, and then returned to petri dishes. Dark and medium-dark colored beads were picked as hits and collected into Corning Costar Spin-X centrifuge tube filters (Sigma-Aldrich, CLS8170). Hit beads were then rinsed 10×30 s (7,000 RPM, tabletop centrifuge), decolorized by overnight incubation in NMP, rinsed in Millipore water (10×30 s), resuspended in TBS, and stored at 4° C.

Individual beads were transferred to wells in a 96 well plate and subjected to cyanogen-bromide cleavage, prepared, and sequenced as described previously (44, 81).

In Vitro ELISA Assays.

ELISA assays for MrkA-binding and epitope selectivity were performed on clear NeutrAvidin Coated High Capacity Plates (ThermoFisher, 15507). The buffer used for all washes and to dissolve all compounds was TBST+0.1% BSA (TBS+0.05% Tween 20+0.1% BSA, pH 7.3) and, unless otherwise stated, steps were conducted at room temperature. Each wash involved a brief 20 s agitation, and all conjugation, blocking, and incubation steps were performed with gentle agitation over the entire stated time period. The general procedure for an ELISA assay was: wash 3×200 μL/well, conjugate with 2 μM of biotinylated compound for 2 h at room temperature (100 μL/well), wash 3×200 μL/well, blocked overnight in 5 wt % milk at 4° C., wash 3×200 μL/well with wash buffer, incubate with titrated compound (e.g., MrkA or epitope) for 1 h, 3×200 μL/well, incubate with primary antibody (either or) for 1 h (100 μL/well), wash 3×200 μL/well, incubate with 1:2,000 anti-rabbit secondary antibody-horseradish peroxidase conjugate (Cell signaling Technologies, 7074S) for 1 h, 3×200 μL/well, develop with the Microwell Peroxidase Substrate System (2-C) (SeraCare, 5120-0047) using 100 μL/well for 1-40 minutes, and quench using 1 M H$_2$SO$_4$ (aq.) at 100 μL/well. For MrkA binding assays, biotinylated PCCs were conjugated to the well surface, recombinant MrkA with an N-terminal 6×His-SUMO-tag (MyBiosource, MBS1248970) was titrated at the desired concentration, and the primary antibody was His-tag antibody, pAb, Rabbit (Genscript, A00174) at a 1:5,000 dilution. For epitope selectivity assays, biotinylated SynEps were conjugated, DNP-conjugated AR-PCCs were titrated at a desired concentration, and the primary antibody was anti-DNP antibody produced in Rabbit (Sigma-Aldrich, D9656) at a 1:8,000 dilution. The PCCs and SynEps used for plate-based ELISA assays had a peg5 linker between the N-terminus of the peptide and the tag, which was either biotin or DNP-modified lysine. For binding tests in the context of mouse sera, the "titrated compound" described in the steps above was dispersed in a solution containing the desired concentration of mouse serum.

Cell Culture.

Bacteria were grown overnight from glycerol stocks by inoculation into either minimal media containing 1% glycerol and 0.3% casamino acids (G-CAA) or Lysogeny Broth (LB) with shaking at 37° C. G-CAA media was used to promote the expression of MrkA, while LB broth was used as a control media for binding tests that involved K. pneumoniae that do not produce MrkA. An immortalised mouse bone marrow derived macrophage cell line (iBMDM, a kind gift from Dr. Eicke Latz) was used in this study. Cells were maintained in RPMI containing 10% serum at 37° C. in a humidified atmosphere with 5% CO$_2$. K. pneumoniae strains BAA 1705 and BAA 2146 were obtained from ATCC, while wild type and MrkA/B/C knockout versions of K. pneumoniae ATCC 43816 were kindly provided by Prof. Matthew Wargo.

Salt Aggregation Tests.

Bacterial were cultured overnight in G-CAA media, washed once in 0.02M phosphate buffer (0.01 M Na$_2$HPO$_4$, 0.01 M NaH$_2$PO$_4$, pH 8), and then resuspended to an O.D.$_{600}$ of 0.95. The bacterial solutions were arrayed onto a single glass slide in 10 μL spots, and then each spot was mixed with an equal volume of phosphate buffer containing (NH$_4$)$_2$SO$_4$. The glass slide was gently agitated for 2 m.

Images were recorded at 10 m and 30 m following agitation, and image acquisition of all the spots took less than 1 m. Measurements were conducted on both live bacteria and heat-killed bacteria that were treated for 10 minutes at 90° C.

Whole-Cell ELISAs.

Detection of the binding of biotinylated PCCs to bacterial surface was performed as follows. $10^8$ bacteria from a culture grown overnight were used for each test. Bacteria were incubated with PBS containing 1% BSA (PBS-BSA) for 1 h at 37° C., washed once with PBS, and then incubated with 5 μM of the biotinylated PCC in PBS-BSA for 1 h at 37° C. After washing thrice with PBS to remove unbound PCCs, bacteria were incubated with Streptavidin-HRP (1:1000) for 1 h at 37° C. Bacteria were washed thoroughly and the TMB reagent was added until visible coloration was observed. The reaction was quenched using 2N $H_2SO_4$ and absorbance was measured at 450 nm. The biotinylated PCCs used for cell-based ELISA assays had a peg5 linker between the N-terminus of the PCC and the biotin tag.

The protocol for detecting anti-DNP recruitment to bacterial cell surfaces is as follows. Bacteria were incubated with the desired concentration of DNP-conjugated PCCs in PBS-BSA for 1 h at 37° C. Residual PCCs were washed off by using PBS-BSA and bacteria were incubated with anti-DNP antibody (1:1000) for 1 h at 37° C. After washing, bacteria were incubated with HRP conjugated secondary antibody (Bio-Rad) at a dilution of 1:10,000 for 1 h at 37° C. Unbound antibody was washed off by using PBS-BSA and the cells were then developed by using TMB reagent. The reaction was quenched using 2N $H_2SO_4$ and absorbance was measured at 450 nm. Anti-MrkA antibody was procured from Biorbyt (orb51318) and used at a concentration of 5 μg/mL, and *K. pneumoniae* antiserum was obtained from abcam (ab20947) and used at a concentration of 5 μg/mL. The DNP-conjugated PCCs used for anti-DNP recruitment assays had a peg5-peg5 linker between the N-terminus of the PCC and the DNP-modified lysine.

Opsonophagocytic Killing (OPK) Assays.

*Klebsiella pneumoniae* BAA1705 was treated with DNP-PCCs followed by incubation with anti-DNP antibody, as described above in the "Cell-Based ELISAs" section. These opsonized bacteria were then used to infect BMDMs at a multiplicity of infection of 50 for 0.5 h at 37° C. Bacteria were then washed by using RPMI 1640 Media and BMDMs were left in cell culture medium containing gentamicin (100 μg/ml). After 1 h and 24 h BMDMs were washed to remove gentamicin and intracellular bacteria were harvested by lysing BMDMs in RPMI media containing 0.2% Triton X 100. Bacterial CFUs were enumerated by plating onto LB agar. Bacterial counts at 1 h indicated the degree of opsonization while those at 24 h served as a measure of microbicidal activity of macrophages. For these measurements, anti-MrkA antibody and *K. pneumoniae* antiserum were used at dilutions of 5 μg/mL each. The DNP-conjugated PCCs used for the phagocytosis and OPK assays had a peg5-peg5 linker between the N-terminus of the PCC and the DNP-modified lysine.

Flow Cytometry.

Cytometry measurements were used to quantify AR-PCC-driven opsonization and opsonophagocytic killing of *K. pneumoniae* cells. For these measurements, *K. pneumoniae* cells were cultured in G-CAA medium overnight, washed, incubated with DNP-tagged AR-PCC at a desired concentration, washed, incubated with anti-DNP antibody conjugated with Alexafluor488, washed, then resuspended in PBS media. The samples were stored at 4° C. for 2 d before cytometry measurements were performed. The cytometer was calibrated by using Rainbow fluorescent beads (3.5 μm diameter) 3.5 m from BD (559123), which aided identification of single *K. pneumoniae* cells in subsequent measurements. Samples were excited with 488 nm light and the fluorescence emission at 530 nm was measured. Sample with no Alexaflour488 stain was used as fluorescent minus one (FMO) control for gating of DNP+ population. FACS data was analyzed on FlowJo v10 software, and the resulting histograms each include fluorescence data from >18,000 cells for strain BAA 2146 (FIG. 4B) and >4,000 cells for strain BAA 1705 (data not shown). PCCs used for flow cytometry assays had a peg5-peg5 linker between the N-terminus of the PCC and the DNP tag.

Example 2: Antibody-Recruiting Protein-Catalyzed Capture Agents (AR-PCCs) Targeting Methicillin-Resistant *Staphylococcus aureus* (MRSA)

To extend the demonstration of development, engineering, and production of AR-PCCS, PCCS to a second pathogen were developed. The pathogen was methicillin-resistant *Staphylococcus aureus* (MRSA) and the target chosen was the MRSA peptidoglycan. FIG. 14 shows the structure of the *S. aureus* peptidoglycan with an MRSA-specific linker bridging the two "stems." FIG. 14 also shows the location of the azidolysine substitutions to make three different SynEps: SynEp 1a, SynEp 1b, and SynEp 1c. These three synthetic epitopes were used to screen a combinatorial one-bead one-compound (OBOC) library of cyclic heptapeptides using the PCC method. The techniques used were generally as described in Example 1. One difference is that the OBOC library used D-amino acids rather than L-amino acids.

The molecular structure of the PCC molecules is shown below:

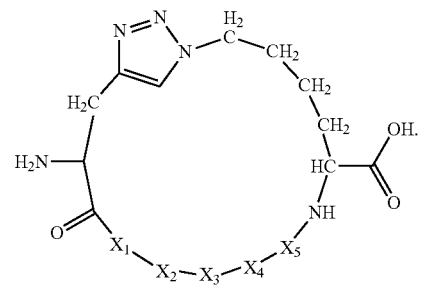

Hits were identified generally as described in Example 1. Amino acid sequences of the variable regions of PCC hits obtained through a single PCC screen against all three MRSA peptidoglycan SynEps (SynEp1a, SynEp 1b, and SynEp 1c) are shown in Table 5. The PCC amino acid sequences were determined by using Matrix-Assisted Laser Desorption Ionization Time-of-Flight tandem mass spectroscopy of cleaved peptides from OBOC library beads identified as hits from a PCC screen.

TABLE 5

| Hit # | Position | | | | | SEQ ID NO: | Homology | |
|---|---|---|---|---|---|---|---|---|
| | X1 | X2 | X3 | X4 | X5 | | | |
| 1 | f (†) | d (§) | e (§) | G | e (§) | 69 | Set 1a | Negative + hydrophobic |
| 2 | f (†) | d (§) | e (§) | G | p | 70 | | hydrophobic |

TABLE 5-continued

| Hit # | X1 | X2 | X3 | X4 | X5 | SEQ ID NO: | Set | Homology |
|---|---|---|---|---|---|---|---|---|
| 3 | l (†) | d (§) | e (§) | G | p | 71 | | |
| 4 | p | e (§) | e (§) | G | t | 24 | | |
| 5 | p | k (*) | d (§) | e (§) | w (†) | 21 | | |
| 6 | G | n | G | d (§) | v (†) | 20 | Set 1b | |
| 7 | e (§) | v (†) | e (§) | t | G | 25 | | |
| 8 | a (†) | G | p | v (†) | e (§) | 31 | | |
| 9 | a (†) | G | k (*) | G | p | 33 | Set 3 | Positive + hydrophobic |
| 10 | a (†) | t | h (*) | s | l (†) | 19 | | |
| 11 | a (†) | k (*) | k (*) | r (*) | p | 34 | | |
| 12 | k (*) | a (†) | d (§) | h (*) | p | 26 | | |
| 13 | G | l (†) | h (*) | t | d (§) | 28 | Set 4 | Zwitterion |
| 14 | k (*) | n | d (§) | p | — | 27 | | |
| 15 | s | d (§) | l (†) | p | r (*) | 29 | | |

Residues in Table 5 are coded based on physicochemical properties of (*) cationic, (§) anionic, or (†) hydrophobic.

Figure 16B:
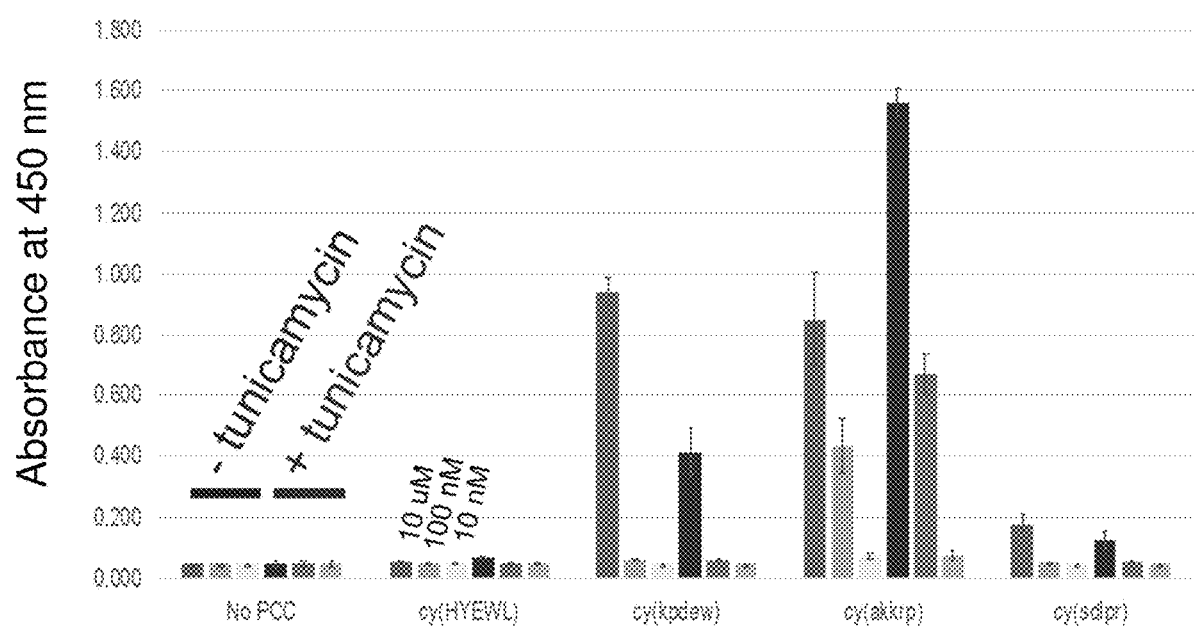
FIG. 16A-16B are graphs showing PCC-driven recruitment of streptavidin-horseradish peroxidase (SAv-HRP) conjugate to live MRSA cells (FIG. 16A) or heat-killed MRSA cells (FIG. 16B) cultured under different antibiotic conditions via enzyme-linked Immunosorbent Assays (ELISAs). All tests were conducted by coating the antigen (MRSA cells) onto the wells of 96-well plates and then exposing the wells solutions containing biotinylated PCCs, then SAv-HRP, then HRP substrate followed by detection via absorbance at 450 nm. Absorbance values greater than the "no PCC" background indicate that several PCCs recruit SAv-HRP to either live cells (FIG. 16A) or heat-killed cells (FIG. 16B) cultured either without antibiotic ("−tunicamycin", blue bars) or with 0.4 micrograms/mL of tunicamycin ("+tunicamycin", red), which reduces the expression of wall teichoic aids by MRSA. All measurements were conducted in triplicate and error bars reflect standard deviations. The PCC sequences are, from left to right in both graphs, SEQ ID NOs: 6, 23, 34, and 29.
Figure 16A:
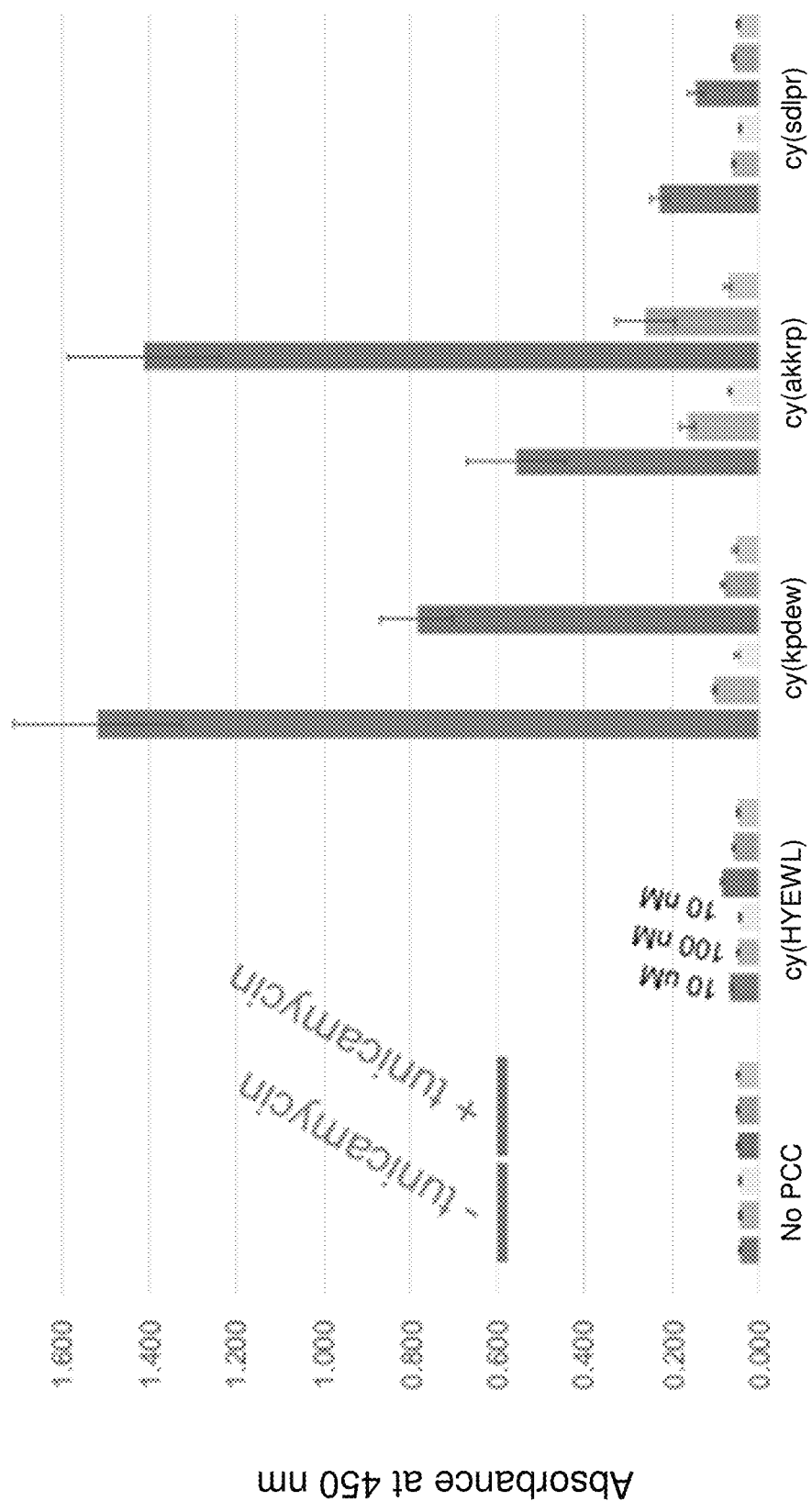

The recruitment ability of selected PCCs was assessed by PCC-driven recruitment of streptavidin-horseradish peroxidase (SAv-HRP) conjugate to live MRSA cells (FIG. 16A) or heat-killed MRSA cells (FIG. 16B) cultured under different antibiotic conditions via enzyme-linked Immunosorbent Assays (ELISAs). All tests were conducted by coating the antigen (MRSA cells) onto the wells of 96-well plates and then exposing the wells solutions containing biotinylated PCCs, then SAv-HRP, then HRP substrate followed by detection via absorbance at 450 nm. Absorbance values greater than the "no PCC" background indicate that several PCCs recruit SAv-HRP to either live cells (FIG. 16A) or heat-killed cells (FIG. 16B) cultured either without antibiotic or with 0.4 micrograms/mL of tunicamycin, which reduces the expression of wall teichoic aids by MRSA. Standout recruiting peptides are cy(kpdew) (SEQ ID NO:23) and cy(akkrp) (SEQ ID NO:34).

REFERENCES

1. Tzouvelekis L S, Markogiannakis A, Psichogiou M, Tassios P T, Daikos G L. Carbapenemases in *Klebsiella pneumoniae* and Other Enterobacteriaceae: an Evolving Crisis of Global Dimensions. Clin Microbiol Rev. 2012; 25:682-707.
2. Spellberg B, Guidos R, Gilbert D, Bradley J, Boucher H W, Scheld W M, et al. The Epidemic of Antibiotic-Resistant Infections: A Call to Action for the Medical Community from the Infectious Diseases Society of America. Clin Infect Dis. 2008; 46:155-64.
3. World Health Organization. Antimicrobial resistance: Global Report on Surveillance. 2014.
4. Fair R J, Tor Y. Antibiotics and Bacterial Resistance in the 21st Century. Perspect Medicin Chem. 2014; 6:25-64.
5. Bush K, Courvalin P, Dantas G, Davies J, Eisenstein B, Huovinen P, et al. Tackling antibiotic resistance. Nat Rev Microbiol. 2011; 9:894-6.
6. Prevention C for DCA. Antibiotic Resistance Threats in the United States, 2013. Atlanta, Georgia; 2013.
7. Ventola C L. The Antibiotic Resistance Crisis Part 1: Causes and Threats. Pharm Ther. 2015; 40:277-83.
8. Roope LSJ, Smith R D, Pouwels K B, Buchanan J, Abel L, Eibich P, et al. The challenge of antimicrobial resistance: What economics can contribute. Science. 2019; 364:41.
9. Humphries R M, Kelesidis T, Bard J D, Ward K W, Bhattacharya D, Lewinski M A. Case Report Successful treatment of pan-resistant *Klebsiella pneumoniae* pneumonia and bacteraemia with a combination of high-dose tigecycline and colistin. J Med Microbiol. 2010; 59:1383-6.
10. Tacconelli E, Mendelson M, Kluytmans J. Discovery, research, and development of new antibiotics: the WHO priority list of antibiotic-resistant bacteria and tuberculosis. Lancet Infect Dis. 2018; 18:318-27.
11. Pitout J D D, Nordmann P, Poirel L. Carbapenemase-Producing *Klebsiella pneumoniae*, a Key Pathogen Set for Global Nosocomial Dominance. Antimicrob Agents Chemother. 2015; 59:5873-84.
12. Munoz-Price L S, Poirel L, Bonomo R A, Schwaber M J, Daikos G L, Cormican M, et al. Clinical epidemiology of the global expansion of *Klebsiella pneumoniae* carbapenemases. Lancet Infect Dis 2013; 13:785-96. Available from web page dx.doi.org/10.1016/S1473-3099(13) 70190-7
13. Brown E D, Wright G D. Antibacterial drug discovery in the resistance era. Nature. 2016; 529:336-43.
14. Systems N, Techniques B, Lee M, Pinto N A, Kim C Y, Yang S, et al. Network Integrative Genomic and Transcriptomic Analysis of Carbapenem-Resistant *Klebsiella pneumoniae* Strains Identifies Genes for Antibiotic Resistance and Virulence. mSystems. 2019; 4:e00202-19.
15. Kavvas E S, Catoiu E, Mih N, Yurkovich J T, Seif Y, Dillon N, et al. Machine Learning and Structural Analysis of *Mycobacterium tuberculosis* Pan-genome Identifies Genetic Signatures of Antibiotic Resistance. Nat Commun 2018; 9:4306. Available from web pagedx.doi.org/ 10.1038/s41467-018-06634-y
16. Dotiwala F, Santara S Sen, Binker-Cosen A A, Li B, Chandrasekaran S, Lieberman J. Granzyme B Disrupts Central Metabolism and Protein Synthesis in Bacteria to Promote an Immune Cell Death Program. Cell. 2017; 171:1125-37.
17. Berry M R, Mathews R J, Ferdinand J R, Jing C, Loudon K W, Wlodek E, et al. Renal Sodium Gradient Orchestrates a Dynamic Antibacterial Defense Zone. Cell 170 (5):860-3. Available from web page dx.doi.org/10.1016/ j.cell.2017.07.022
18. Wen X, Xu X, Sun W, Chen K, Pan M, Ming J M, et al. G-protein-coupled formyl peptide receptors play a dual role in neutrophil chemotaxis and bacterial phagocytosis. Mol Biol Cell. 2019; 30:346-56.
19. Barnes L, Heithoff D M, Mahan S P, Fox G N, Zambrano A, Choe J, et al. Smartphone-based pathogen diagnosis in urinary sepsis patients. EBioMedicine 2018; 36:73-82. Available from web page doi.org/10.1016/ j.ebiom.2018.09.001
20. Mccarthy K A, Kelly M A, Li K, Cambray S, Hosseini A S, Opijnen T Van, et al. Phage Display of Dynamic Covalent Binding Motifs Enables Facile Development of Targeted Antibiotics. J Am Chem Soc. 2018; 140:6137-45.
21. Czaplewski L, Bax R, Clokie M, Dawson M, Fairhead H, Fischetti V A, et al. Alternatives to antibiotics—a pipeline portfolio review. Lancet Infect Dis. 2016; 16:239-51.
22. Lu L L, Suscovich T J, Fortune S M, Alter G. Beyond binding: antibody effector functions in infectious diseases. Nat Rev Immunol. 2019; 18:46-61.
23. Hancock REW, Nijnik A, Philpott D J. Modulating Immunity as a Therapy for Bacterial Infections. Nat Rev Microbio 2012; 10:243-54. Available from: web page dx.doi.org/10.1038/nrmicro2745.

24. McEnaney P J, Parker C G, Zhang A X, Spiegel D A. Antibody-Recruiting Molecules: An Emerging Paradigm for Engaging Immune Function in Treating Human Disease. 2012;
25. Feigman M S, Kim S, Pidgeon S E, Regen S, Im W, Pires M M, et al. Synthetic Immunotherapeutics against Gram-negative Pathogens Article Synthetic Immunotherapeutics against Gram-negative Pathogens. Cell Chem Biol 2018; 25(10):1185-1194.e5. Available from web page doi.org/10.1016/j.chembiol.2018.05.019.
26. Chirkin E, Muthusamy V, Mann P, Roemer T, Nantermet P G, Spiegel D A. Antifungal Agents Hot Paper Neutralization of Pathogenic Fungi with Small-Molecule Immunotherapeutics. Angew Chemie Int Ed. 2017; 56:13036-40.
27. Murelli R P, Zhang A X, Michel J, Jorgensen W L, Spiegel D A. Chemical Control over Immune Recognition: A Class of Antibody-Recruiting Small Molecules That Target Prostate Cancer. J Am Chem Soc. 2009; 131:17090-2.
28. Giandomenico A Di, Keller A, Gao C, Rainey G J, Warrener P, Camara M M, et al. A multifunctional bispecific antibody protects against *Pseudomonas aeruginosa* A multifunctional bispecific antibody protects against *Pseudomonas aeruginosa*. Sci Transl Med. 2014; 6:262ra155.
29. Saphire E O, Schendel S L, Gunn B M, Milligan J C, Alter G. Antibody-mediated protection against Ebola virus. Nat Immunol 2018; 19:1169-78. Available from web page dx.doi.org/10.1038/s41590-018-0233-9.
30. Lorenz U, Lorenz B, Schmitter T, Streker K, Erck C, Nickel J, et al. Functional Antibodies Targeting IsaA of *Staphylococcus aureus* Augment Host Immune Response and Open New Perspectives for Antibacterial Therapy. Antimicrob Agents Chemother. 2011; 55(1):165-73.
31. Digiandomenico A, Warrener P, Hamilton M, Guillard S, Ravn P, Minter R, et al. Identification of broadly protective human antibodies to *Pseudomonas aeruginosa* exopolysaccharide Psl by phenotypic screening. J Exp Med. 2012; 209(7):1273-87.
32. Wang Q, Chang C, Pennini M, Pelletier M, Rajan S, Zha J, et al. Target-Agnostic Identification of Functional Monoclonal Antibodies Against *Klebsiella pneumoniae* Multimeric MrkA Fimbrial Subunit. J Infect Dis. 2018; 213:1800-8.
33. Wang Q, Chen Y, Cvitkovic R, Pennini M E, Chang C S, Pelletier M, et al. Anti-MrkA monoclonal antibodies reveal distinct structural and antigenic features of MrkA. PLoS One. 2017; 12:e017059.
34. Sparrow E, Friede M, Torvaldsen S. Therapeutic antibodies for infectious diseases. Bull World Health Organ. 2017; 95:235-7.
35. Pelfrene E, Mura M, Sanches A C, Cavaleri M. Monoclonal antibodies as anti-infective products: a promising future? Clin Microbiol Infect 2019; 25:60-4. Available from web page doi.org/10.1016/j.cmi.2018.04.024.
36. Sabulski M J, Pidgeon S E, Pires M M. Immunotargeting of *Staphylococcus aureus* via surface remodeling complexes. Chem Sci. 2017; 8:6804.
37. Bertozzi C R, Bednarski M D. A Receptor-Mediated Immune Response Using Synthetic Glycoconjugates. J Am Chem Soc. 1992; 114:5543-6.
38. Krishnamurthy V M, Quinton L J, Estroff L A, Metallo S J, Isaacs J M, Mizgerd J P, et al. Promotion of opsonization by antibodies and phagocytosis of Gram-positive bacteria by a bifunctional polyacrylamide. Biomaterials. 2006; 27:3663-74.
39. Fura J M, Pidgeon S E, Birabaharan M, Pires M M. Dipeptide-Based Metabolic Labeling of Bacterial Cells for Endogenous Antibody Recruitment. 2016.
40. Fura J M, Sabulski M J, Pires M M. D-Amino Acid Mediated Recruitment of Endogenous Antibodies to Bacterial Surfaces. ACS Chem Biol. 2014; 9:1480-9.
41. Agnew H D, Coppock M B, Idso M N, Lai B T, Liang J, Mccarthy-*torrens* A M, et al. Protein-Catalyzed Capture Agents. Chem Rev. 2019; 119:9950-70.
42. Das S, Nag A, Liang J, Bunck D N, Umeda A, Farrow B, et al. A General Synthetic Approach for Designing Epitope Targeted Macrocyclic Peptide Ligands. Angew Chemie Int Ed. 2015; 54:13219-24.
43. Bunck D N, Atsavapranee B, Museth A K, Vandervelde D, Heath J R. Modulating the Folding Landscape of Superoxide Dismutase 1 with Targeted Molecular Binders. Angew Chemie. 2018; 130:6320-3.
44. Lai B T, Wilson J A, Loredo J M, Pitram S M, LaBerge N A, Heath J R, et al. Epitope Targeted Macrocyclic Peptide Ligand with Picomolar Cooperative Binding to Interleukin-17F. Chem—A Eur J. 2018; 24:3760-7.
45. McCarthy A M, Kim J, Museth A K, Henning R K, Heath J E, Winson E, et al. Allosteric Inhibitor of KRas Identified Using a Barcoded Assay Microchip Platform. Anal Chem. 2018; 90:8824-30.
46. Guilhen C, Charbonnel N, Parisot N, Gueguen N, Iltis A, Forestier C, et al. Transcriptional profiling of *Klebsiella pneumoniae* defines signatures for planktonic, sessile and biofilm-dispersed cells. BMC Genomics 2016; 17:237. Available from web page dx.doi.org/10.1186/s12864-016-2557-x
47. Cahill B K, Seeley K W, Gutel D, Ellis T N. *Klebsiella pneumoniae* O antigen loss alters the outer membrane protein composition and the selective packaging of proteins into secreted outer membrane vesicles. Microbiol Res. 2015; 180:1-10.
48. Brinkworth A J, Hammer C H, Olano L R, Kobayashi S D, Liang C, Kreiswirth B N, et al. Identification of Outer Membrane and Exoproteins of Carbapenem-Resistant Multilocus Sequence Type 258 *Klebsiella pneumoniae*. PLoS One. 2015; 10:e0123219.
49. Liu Y, Wang H, Sun X, Yang H, Wang Y, Song W. Study on Mechanisms of Colonization of Nitrogen-Fixing PGPB, *Klebsiella pneumoniae* NG14 on the Root Surface of Rice and the Formation of Biofilm. Curr Microbiol. 2011; 62:1113-22.
50. Paczosa M K, Mecsas J. *Klebsiella pneumoniae*: Going on the Offense with a Strong Defense. Microbiol Mol Biol Rev. 2016; 80:629-61.
51. Holt K E, Wertheim H, Zadoks R N, Baker S, Whitehouse C A, Dance D, et al. Genomic analysis of diversity, population structure, virulence, and antimicrobial resistance in *Klebsiella pneumoniae*, an urgent threat to public health. Proc Natl Acad Sci USA. 2015; 112:E3574-81.
52. Martin R M, Bachman M A. Colonization, Infection, and the Accessory Genome of *Klebsiella pneumoniae*. Front Cell Infect Microbiol. 2018; 8:4.
53. Alcántar-Curiel M D, Blackburn D, Saldaña Z, Gayosso-Vásquez C, Iovine N, De la Cruz M A, et al. Multifunctional Analysis of *Klebsiella pneumoniae* fimbrial types in adherence and biofilm formation. Virulence. 2013; 5594:129-38.
54. Gerlach G F, Allen B L, Clegg S. Molecular characterization of the type 3 (M R/K) fimbriae of *Klebsiella pneumoniae*. J Bacteriol. 1988; 170:3547-53.

55. Chen F-J, Chan C-H, Huang Y-J, Liu K-L, Peng H-L, Chang H-Y, et al. Structural and Mechanical Properties of *Klebsiella pneumoniae* Type 3 Fimbriae. J Bacteriol. 2011; 193(7):1718-25.

56. Alcántar-Curiel M D, Ledezma-Escalante C A, Jarillo-Quijada M D, Gayosso-Vázquez C, Rayo M-O, Rodríguez-Noriega E, et al. Association of Antibiotic Resistance, Cell Adherence, and Biofilm Production with the Endemicity of Nosocomial *Klebsiella pneumoniae*. Biomed Res Int. 2018; 2018.

57. Klausen M S, Jespersen M C, Nielsen H, Jensen K K, Jurtz V I, Sønderby C K, et al. NetSurfP-2.0: improved prediction of protein structural features by integrated deep learning. BioRxiv. 2018; 311209.

58. Jespersen M C, Peters B, Nielsen M, Marcatili P. BepiPred-2.0: improving sequence-based B-cell epitope prediction using conformational epitopes. Nucleic Acids Res. 2017; 45:W24-9.

59. Berglund L, Andrade J, Odeberg J, Uhlén M. The epitope space of the human proteome. Protein Sci. 2008; 17:606-13.

60. Mádiera F, Park Y mi, Lee J, Buso N, Gur T, Madhusoodanan N, et al. The EMBL-EBI search and sequence analysis tools APIs in 2019. Nucleic Acids Res. 2019.

61. Waterhouse A M, Procter J B, Martin DMA, Clamp M, Barton G J. Jalview Version 2—a multiple sequence alignment editor and analysis workbench. Bioinformatics. 2009; 25:1189-91.

62. Shokat, K. M.; Schultz, P. G. Redirecting the Immune Response: Ligand-Mediated Immunogenicity. J. Am. Chem. Soc. 1991, 113 (16), 1861-1862.

63. Sauer F G, Remaut H, Hultgren S J, Waksman G. Fiber assembly by the chaperone-usher pathway. Biochem Biophys Acta. 2004; 1694:259-67.

64. Wargo M J. Pulmonary Surfactant Promotes Virulence Gene Expression and Biofilm Formation in *Klebsiella pneumoniae*. Infect Immun. 2018; 86(7):e00135-18.

65. Humphries A, DeRidder S, Baumler A J. *Salmonella enterica* Serotype *Typhimurium* Fimbrial Proteins Serve as Antigens during Infection of Mice. Infect Immun. 2005; 73:5329-38.

66. Blumer C, Kleefeld A, Lehnen D, Heintz M, Dobrindt U, Nagy G, et al. Regulation of type 1 fimbriae synthesis and biofilm formation by the transcriptional regulator LrhA of *Escherichia coli*. Microbiology. 2005; 151:3287-98.

67. Karjalaninen K, Makela O. Concentrations of three hapten-binding immunoglobulins in pooled normal human serum. Eur J Immunol. 1976; 6:88-93.

68. Rullo A F, Fitzgerald K J, Muthusamy V, Liu M, Yuan C, Huang M, et al. Zuschriften Antitumor Agents Re-engineering the Immune Response to Metastatic Cancer: Antibody-Recruiting Small Molecules Targeting the Urokinase Receptor Zuschriften Angewandte. Angew Chemie. 2016; 128:3706-10.

69. Lu Y, You F, Vlahov I, Westrick E, Fan M, Low P S, et al. Folate-targeted dinitrophenyl hapten immunotherapy: effect of linker chemistry on antitumor activity and allergic potential. Mol Pharm. 2007; 4(5):2432-43.

70. Barrett T, Wilhite S E, Ledoux P, Evangelista C, Kim I F, Tomashevsky M, et al. NCBI GEO: archive for functional genomics data sets-update. Nucleic Acids Res. 2013; 41:D991-5.

71. Marbach D, Costello J C, Kuffner R, Vega N M, Prill R J, Camacho D M, et al. Wisdom of crowds for robust gene network inference. Nat Methods. 2016; 9(8):796-804.

72. Arrieta-Ortiz M L, Hafemeister C, Bate A R, Chu T, Greenfield A, Shuster B, et al. An experimentally supported model of the *Bacillus subtilis* global transcriptional regulatory network. Mol Syst Biol. 2015; 11:839.

73. Cowles C E, Li Y, Semmelhack M F, Cristea I M, Silhavy T J. The free and bound forms of Lpp occupy distinct subcellular locations in *Escherichia coli*. Mol Microbiol. 2011; 79:1168-81.

74. Wilson M M, Bernstein H D. Surface-Exposed Lipoproteins: An Emerging Secretion Phenomenon in Gram-Negative Bacteria. Trends Microbiol 2016; 24:198-208. Available from web page dx.doi.org/10.1016/j.tim.2015.11.006

75. Lee J C, Lee E J, Lee J H, Jun S H, Choi C W, Kim S I I, et al. *Klebsiella pneumoniae* Secretes Outer Membrane Vesicles that Induce the Innate Immune Response. FEBS Microbiol Lett. 2012; 331:17-24.

76. Hsieh P, Liu J, Pan Y, Wu M, Lin T, Huang Y, et al. *Klebsiella pneumoniae* Peptidoglycan-Associated Lipoprotein and Murein Lipoprotein Contribute to Serum Resistance, Antiphagocytosis, and Proinflammatory Cytokine Stimulation. J Infect Dis. 2013; 208:1580-9.

77. Ferguson A D, Braun V, Fiedler H, Coulton J W, Diederichs K A Y, Welte W. Crystal Structure of the Antibiotic Albomycin in Complex with the Outer Membrane Transporter FhuA. Protein Sci. 2000; 9:956-63.

78. Thoma J, Bosshart P, Pfreundschuh M, Muller D J. Out but Not In: The Large Transmembrane Beta-Barrel Protein FhuA Unfolds but Cannot Refold via Beta-Hairpins. Structure. 2012; 20:2185-90.

79. Tsang M-J, Yakhnina A A, Bernhardt T G. NlpD links cell wall remodeling and outer membrane invagination during cytokinesis in *Escherichia coli*. PLOS Genet. 2017; 13:e1006888.

80. Laar T A Van, Chen T, You T, Leung P. Sublethal Concentrations of Carbapenems Alter Cell Morphology and Genomic Expression of *Klebsiella pneumoniae* Biofilms. Antimicrob Agents Chemother. 2015; 59:1707-17.

81. Lee S S, Lim J, Cha J, Tan S, Heath J R. Rapid Microwave-assisted CNBr Cleavage of Bead-bound Peptides. J Comb Chem. 2008; 10:807-9.

82. Roca, I.; Akova, M.; Baquero, F.; Carlet, J.; Cavaleri, M.; Coenen, S.; Cohen, J.; Findlay, D.; Gyssens, I.; Heure, O. E. The Global Threat of Antimicrobial Resistance: Science for Intervention. New Microbes New Infect. 2015, 6, 22-29.

83. Gold, H. S.; Moellering Jr., R. C. Antimicrobial-Drug Resistance. N. Engl. J. Med. 1996, 335, 1445-1453.

84. Robinson, T. P.; Bu, D. P.; Carrique-mas, J.; Fevre, E. M.; Gilbert, M.; Grace, D.; Hay, S. I.; Jiwakanon, J.; Kakkar, M. Antibiotic Resistance Is the Quintessential One Health Issue. Trans. R. Soc. Trop. Med. Hyg. 2016, 110, 377-380.

85. Watkins, R. R.; Bonomo, R. A. Overview: Global and Local Impact of Antibiotic Resistance. Infect. Dis. Clin. North Am. 2016, 30, 313-322.

86. Davies, J.; Davies, D. Origins and Evolution of Antibiotic Resistance. 2010, 74 (3), 417-433.

87. Wise, R.; Hart, T.; Cars, O.; Streulens, M.; Helmuth, R.; Huovinen, P.; Sprenger, M. Antimicrobial Resistance Is a Major Threat to Public Health. Br. Med. J. 1998, 317 (September), 609-610.

88. Cohen, M. L. Epidemiology of Drug Resistance: Implications for a Post-Antimicrobial Era. Science 1992, 257, 1050-1055.

89. Ventola, C. L. The Antibiotic Resistance Crisis Part 1: Causes and Threats. Pharm. Ther. 2015, 40, 277-283.

90. Högberg, L. D.; Heddini, A.; Cars, O. The Global Need for Effective Antibiotics: Challenges and Recent Advances. Trends Pharmacol. Sci. 2010, 31, 509-515.
91. Coppock, M. B.; Warner, C. R.; Dorsey, B.; Orlicki, J. A.; Sarkes, D. A.; Lai, B. T.; Pitram, S. M.; Rohde, R. D.; Malette, J.; Wilson, J. A.; et al. Protein Catalyzed Capture Agents with Tailored Performance for in Vitro and in Vivo Applications. Pept. Sci. 2016, 108 (2), e22934.
92. McCarthy, A. M.; Kim, J.; Museth, A. K.; Henning, R. K.; Heath, J. E. J. R. J. E.; Winson, E.; Oh, J. J.; Liang, J.; Hong, S.; Heath, J. E. J. R. J. E. Allosteric Inhibitor of KRas Identified Using a Barcoded Assay Microchip Platform. Anal. Chem. 2018, 90 (15), 8824-8830.
93. Wang, W.; Sun, J.; Hartlep, M.; Deckwer, W.-D.; Zeng, A.-P. Combined Use of Proteomic Analysis and Enzyme Activity Assays for Metabolic Pathway Analysis of Glycerol Fermentation by *Klebsiella pneumoniae*. Biotechnol. Bioeng. 2003, 578, 525.
94. Lin, M.-H.; Hsu, T.-L.; Lin, S.-Y.; Pan, Y.-J.; Jan, J.-T.; Wang, J.; Khoo, K.-H.; Wu, S.-H. Phosphoproteomics of *Klebsiella pneumoniae* NTUH-K2044 Reveals a Tight Link between Tyrosine Phosphorylation and Virulence. Mol. Cell. Proteomics 2009, 8, 2613-2623.
95. Kurupati, P.; Teh, B. K.; Kumarasinghe, G.; Poh, C. L. Identification of Vaccine Candidate Antigens of an ESBL Producing *Klebsiella pneumoniae* Clinical Strain by Immunoproteome Analysis. Proteomics 2006, 6, 836-844.
96. Molina-Santiago, C.; Daddaoua, A.; Gómez-lozano, M.; Udaondo, Z.; Molin, S.; Ramos, J.-L. Differential Transcriptional Response to Antibiotics by *Pseudomonas putida* DOT-T1E. Environ. Microbiol. 2015, 17, 3251-3262.
97. Huang, T.; Lam, I.; Chang, H.; Tsai, S.; Palsson, B. O.; Charusanti, P. Capsule Deletion via a k-Red Knockout System Perturbs Biofilm Formation and Fimbriae Expression in *Klebsiella pneumoniae* MGH 78578. BMC Res. Notes 2014, 7 (13), 1-8.
98. Seo, J.; Hong, J. S.; Kim, D.; Cho, B.; Huang, T.; Tsai, S.; Palsson, B. O.; Charusanti, P. Multiple-Omic Data Analysis of *Klebsiella pneumoniae* MGH 78578 Reveals Its Transcriptional Architecture and Regulatory Features. BMC Genomics 2012, 13 (679), 1-12.
99. Deleo, F. R.; Chen, L.; Porcella, S. F.; Martens, C. A.; Kobayashi, S. D.; Porter, A. R.; Chavda, K. D.; Jacobs, M. R.; Mathema, B.; Olsen, R. J.; et al. Molecular Dissection of the Evolution of Carbapenem-Resistant Multilocus Sequence Type 258 *Klebsiella pneumoniae*. Proc. Natl. Acad. Sci. U.S.A 2014, 111 (13), 4988-4993.
100. Opal, S. M. Non-Antibiotic Treatments for Bacterial Diseases in an Era of Progressive Antibiotic Resistance. Crit. Care 2016, 20, 397.
101. Albertí, S.; Marqués, G.; Camprubí, S.; Merino, S.; Tomás, J. M.; Vivanco, F.; Benedí, V. J. C1q Binding and Activation of the Complement Classical Pathway by *Klebsiella pneumoniae* Outer Membrane Proteins. Infect. Immun. 1993, 61 (3), 852-860.

It is understood that the disclosed method and compositions are not limited to the particular methodology, protocols, and reagents described as these can vary. It is also to be understood that the terminology used herein is for the purpose of describing particular embodiments only, and is not intended to limit the scope of the present invention which will be limited only by the appended claims.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a ligand is disclosed and discussed and a number of modifications that can be made to a number of molecules including the ligand are discussed, each and every combination and permutation of ligand and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It must be noted that as used herein and in the appended claims, the singular forms "a," "an," and "the" include plural reference unless the context clearly dictates otherwise.

Thus, for example, reference to "a ligand" includes a plurality of such ligands, reference to "the ligand" is a reference to one or more ligands and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Unless the context clearly indicates otherwise, use of the word "can" indicates an option or capability of the object or condition referred to. Generally, use of "can" in this way is meant to positively state the option or capability while also leaving open that the option or capability could be absent in other forms or embodiments of the object or condition referred to. Unless the context clearly indicates otherwise, use of the word "may" indicates an option or capability of the object or condition referred to. Generally, use of "may" in this way is meant to positively state the option or capability while also leaving open that the option or capability could be absent in other forms or embodiments of the object or condition referred to. Unless the context clearly indicates otherwise, use of "may" herein does not refer to an unknown or doubtful feature of an object or condition.

Ranges can be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. can include numerous options and alternatives, this should not be construed as, and is not an admission that, such options and alternatives are equivalent to each other or, in particular, are obvious alternatives. Thus, for example, a list of different ARMs does not indicate that the listed ARMs are obvious one to the other, nor is it an admission of equivalence or obviousness.

Every ligand, ARM, EPI, compound, and composition disclosed herein is intended to be and should be considered to be specifically disclosed herein. Further, every subgroup that can be identified within this disclosure is intended to be and should be considered to be specifically disclosed herein. As a result, it is specifically contemplated that any ligand, ARM, EPI, compound, or composition, or subgroup of ligands, ARMs, EPIs, compounds, or compositions can be either specifically included for or excluded from use or included in or excluded from a list of ligands, ARMs, EPIs, compounds, and compositions.

Those skilled in the art will recognize, or be able to ascertain using no more than routine experimentation, many equivalents to the specific embodiments of the method and compositions described herein. Such equivalents are intended to be encompassed by the following claims.

We claim:

1. An epitope-targeted immunostimulant (EPI) comprising a cyclic synthetic peptide ligand conjugated or coupled to an antibody-recruiting moiety,
wherein the cyclic synthetic peptide ligand has affinity for MrkA protein exposed on a surface of a target,
wherein the cyclic synthetic peptide ligand comprises an amino acid sequence and a triazole residue, wherein the triazole residue is a 1,4-substituted-1,2,3-triazole residue (Tz4) or a 1,5-substituted-1,2,3-triazole residue (Tz5),
wherein the antibody-recruiting moiety is recognized by an antibody that mediates recognition and phagocytosis of the target by an immune cell, and
wherein the amino acid sequence of the cyclic synthetic peptide ligand is LLFFF (SEQ ID NO:5), ALFFF (SEQ ID NO:7), LAFFF (SEQ ID NO:8), LLAFF (SEQ ID NO:9), HLFFF (SEQ ID NO:13), LLFF(4-fluoro-phenylalanine) (SEQ ID NO:36), LFFF (SEQ ID NO:37), FYTKG (SEQ ID NO:42), EYEGK (SEQ ID NO:43), PWNKG (SEQ ID NO:44), SWTGE (SEQ ID NO:45), RHPGE (SEQ ID NO:46), NRTGP (SEQ ID NO:47), PREGP (SEQ ID NO:48), SNFGP (SEQ ID NO:49), EKTPG (SEQ ID NO:50), KGFPG (SEQ ID NO:51), GGFNA (SEQ ID NO:52), NGPVH (SEQ ID NO:53), WYKGP (SEQ ID NO:54), WDYKG (SEQ ID NO:55), YRHLG (SEQ ID NO:56), GVHRL (SEQ ID NO:57), GVVEK (SEQ ID NO:58), GLTHA (SEQ ID NO:59), SLGLT (SEQ ID NO:60), KPAG (SEQ ID NO:61), AKPEP (SEQ ID NO:62), EWVSA (SEQ ID NO:63), EFSGV (SEQ ID NO:64), DGTAL (SEQ ID NO:65), VVNLP (SEQ ID NO:66), TPNLP (SEQ ID NO:67), RPEGP (SEQ ID NO:68), or LLFF (SEQ ID NO:73).

2. The EPI of claim 1, wherein the amino acid sequence of the cyclic synthetic peptide ligand is LLFFF (SEQ ID NO:5).

3. An epitope-targeted immunostimulant (EPI) comprising a cyclic synthetic peptide ligand conjugated or coupled to an antibody-recruiting moiety,
wherein the cyclic synthetic peptide ligand has affinity for Staphylococcus aureus peptidoglycan exposed on a surface of a target,
wherein the cyclic synthetic peptide ligand comprises an amino acid sequence and a triazole residue, wherein the triazole residue is a 1,4-substituted-1,2,3-triazole residue (Tz4) or a 1,5-substituted-1,2,3-triazole residue (Tz5),
wherein the antibody-recruiting moiety is recognized by an antibody that mediates recognition and phagocytosis of the target by an immune cell, and
wherein the amino acid sequence of the cyclic synthetic peptide ligand is kpdew (SEQ ID NO:23), akkrp (SEQ ID NO:34), athsl (SEQ ID NO:19), GnGdv (SEQ ID NO:20), pkdew (SEQ ID NO:21), peeGt (SEQ ID NO:24), evetG (SEQ ID NO:25), kadhp (SEQ ID NO:26), kndp (SEQ ID NO:27), Glhtd (SEQ ID NO:28), sdlpr (SEQ ID NO:29), pdedw (SEQ ID NO:30), aGpve (SEQ ID NO:31), akGGp (SEQ ID NO:32), aGkGp (SEQ ID NO:33), fdeGe (SEQ ID NO:69), fdeGp (SEQ ID NO:70), or ldeGp (SEQ ID NO:71).

4. The EPI of claim 3, wherein the amino acid sequence of the cyclic synthetic peptide ligand is kpdew (SEQ ID NO:23) or akkrp (SEQ ID NO:34).

5. The EPI of claim 1 or 3, wherein the triazole residue is a 1,4-substituted-1,2,3-triazole residue (Tz4).

6. The EPI of claim 1 or 3, wherein the triazole residue is a 1,5-substituted-1,2,3-triazole residue (Tz5).

7. The EPI of claim 1 or 3, wherein the antibody-recruiting moiety is an immunogen endogenously recognized by a mammalian immune system.

8. The EPI claim 1 or 3, wherein the antibody-recruiting moiety is an immunogen endogenously recognized by a human immune system.

9. The EPI of claim 1 or 3, wherein the antibody-recruiting moiety is 2,4-dinitrophenyl (DNP), alpha-galactose, galactose(alpha1-3)galactose, beta-lactam, 1,3-diketone, avidin, fluorescein, fluorescein-DNP, or nitrophenol.

10. The EPI of claim 1 or 3, wherein the cyclic synthetic peptide ligand is comprised in a multi-ligand,
wherein the multi-ligand further comprises a second ligand covalently linked to the cyclic synthetic peptide ligand.

11. A pharmaceutical composition comprising the EPI of claim 1 or 3 and a pharmaceutically acceptable carrier.

12. The EPI of claim 1 or 3, wherein the cyclic synthetic peptide ligand has the structure:

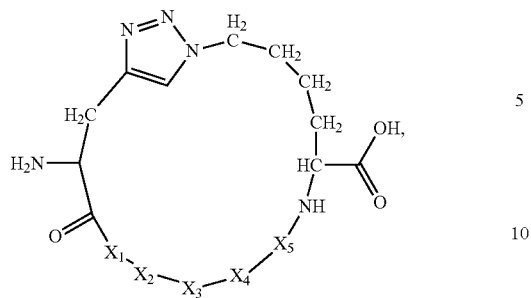
wherein $X_1$-$X_2$-$X_3$-$X_4$-$X_5$ represents the amino acid sequence of the cyclic synthetic peptide ligand, wherein $X_1$-$X_2$-$X_3$-$X_4$-$X_5$ is in the N-terminus to C-terminus direction.
* * * * *

UNITED STATES PATENT AND TRADEMARK OFFICE
CERTIFICATE OF CORRECTION

| | | |
|---|---|---|
| PATENT NO. | : 12,201,679 B2 | Page 1 of 1 |
| APPLICATION NO. | : 16/841635 | |
| DATED | : January 21, 2025 | |
| INVENTOR(S) | : Heath et al. | |

It is certified that error appears in the above-identified patent and that said Letters Patent is hereby corrected as shown below:

In the Claims

In Column 98, in Claim 8, Line 52, delete "EPI" and insert -- EPI of --, therefor.

Signed and Sealed this
Fifteenth Day of April, 2025

Coke Morgan Stewart
*Acting Director of the United States Patent and Trademark Office*